US006831154B1

(12) United States Patent
Bartel

(10) Patent No.: US 6,831,154 B1
(45) Date of Patent: Dec. 14, 2004

(54) MEMBRANE-ASSOCIATED PROTEIN 17KD (MAP17)-INTERACTING PROTEIN AND USE THEREOF

(75) Inventor: Paul Bartel, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 161 days.

(21) Appl. No.: 10/146,710

(22) Filed: May 14, 2002

Related U.S. Application Data

(60) Provisional application No. 60/291,221, filed on May 16, 2001.

(51) Int. Cl.$^7$ .............................................. C07K 14/00
(52) U.S. Cl. ....................................................... 530/350
(58) Field of Search ........................................ 530/350

(56) References Cited

U.S. PATENT DOCUMENTS

| | | |
|---|---|---|
| 5,223,409 A | 6/1993 | Ladner et al. |
| 5,283,173 A | 2/1994 | Fields et al. |
| 5,403,484 A | 4/1995 | Ladner et al. |
| 5,571,698 A | 11/1996 | Ladner et al. |
| 5,837,500 A | 11/1998 | Ladner et al. |

OTHER PUBLICATIONS

Tjian, Robert, et al., "Transcriptional Activation: A Complex Puzzle with Few Easy Pieces", *Cell,* Apr. 8, 1994; 77:5–8.
Kocher, Olivier, et al., "Identification of a Novel Gene, Selectively Up–Regulated in Human Carcinomas, Using the Differential Display Technique", *Clinical Cancer Research,* Oct. 1995; 1:1209–1215.
Kocher, Olivier, et al., "Identification and Partial Characterization of a Novel Membrane–Associated Protein (MAP17) Up–Regulated in Human Carcinomas and Modulating Cell Replication and Tumor Growth", *American Journal of Pathology,* Aug. 1996; 149(2):493–500.
Altschul, Stephen F., et al., "Gapped BLAST and PSI–BLAST: a new generation of protein database search programs", *Nucleic Acids Research,* 1997; 25(17):3389–3402.
Winter, Dirk, et al., "The complex containing actin–related proteins Arp2 and Arp3 is required for the motility and integrity of yeast actin patches", *Current Biology,* 1997; 7:519–529.
Fire, Andrew, et al., "Potent and specific genetic interference by double–stranded RNA in *Caenorhabditis elegans*", *Nature,* Feb. 19, 1998; 391:806–811.
Zambrowicz, Brian P., et al., "Disruption and sequence identification of 2,000genes in mouse embryonic stem cells", *Nature,* Apr. 9, 1998; 392:608–611.

De Beer, Tonny, et al., "Structure and Asn–Pro–Phe Binding Pocket of the Eps 15 Homology Domain", *Science,* Aug. 28, 1998; 281:1357–1360.
Dandekar,Thomas, et al., "Conservation of gene order: a fingerpirnt of proteins that physically interact", *TIBS,* Sep. 1998; 23:324–328.
Overbeek, Ross, et al., "The use of gene clusters to infer functional coupling", *Proc. Natl. Acad. Sci. USA,* Mar. 1999; 96:2896–2901.
Pellegrini, Matteo, et al., "Assigning protein functions by comparative genome analysis: Protein phylogenetic profiles", *Proc. Natl. Acas. Sci. USA,* Apr. 1999; 96:4285–4288.
Marcotte, Edward M., et al., "Detecting Protein Function and Protein–Protein Interactions from Genome Sequences", *Science,* Jul. 30, 1999; 285:751–753.
Winzeler, Elizabeth W., et al., "Functional Characterization of the *S. cerevisiae* Genome by Gene Deletion and Parallel Analysis", *Science,* Aug. 6, 1999; 285:901–906.
Enright, Anton J., et al., "Protein interaction maps for complete genomes based on gene fusion events", *Nature,* Nov. 4, 1999; 402:86–90.
Houry, Walid A., et al., "Identification of in vivo substrates of the chaperonin GroEL" *Nature,* Nov. 11, 1999; 402:147–154.
Jaeger, Claudia, et al., "The Membrane–Associated Protein pKe#192/MAP1 in Human Keratinocytes", *J. Invest. Dermatol.,* 2000; 115:375–380.
Rout, Michael P., et al., "The Yeast Nuclear Pore Complex: Composition, Architecture, and Transport Mechanism", *The Journal of Cell Biology,* Feb. 21, 2000; 148(4):635–651.
Eisenberg, David, et al., "Protein function in the post–genomic era", *Nature,* Jun. 15, 2000; 405:823–826.
Fernandez–Chacon, Rafael, et al., "Novel SCAMPs Lacking NPF Repeats: Ubiqultous and Synaptic Vesicle–Specific Forms Implicate SCAMPs in Multiple Membrane–Trafficking Functions", *The Journal of Neuroscience,* Nov. 1, 2000; 20(21):7941–7950.

*Primary Examiner*—Karen Cochrane Carlson
*Assistant Examiner*—Anand Desai
(74) *Attorney, Agent, or Firm*—Jonathan A. Baker; Jay Z. Zhang; Myriad IP Dept.

(57) ABSTRACT

Protein complexes are provided comprising MAP17 and SCAMP2. The protein complexes are useful in screening assays for identifying compounds effective in modulating the protein complexes and in treating and/or preventing diseases and disorders associated with MAP17 and SCAMP2. In addition, methods for detecting the protein complexes and modulating the functions and activities of the protein complexes or interacting members thereof are also provided.

12 Claims, No Drawings

MEMBRANE-ASSOCIATED PROTEIN 17KD (MAP17)-INTERACTING PROTEIN AND USE THEREOF

CROSS-REFERENCE TO RELATED APPLICATION

This application claim priority under 35 U.S.C. § 119(e) to provisional application Ser. No. 60/291,221, filed May 16, 2001, which is hereby incorporated by reference in its entirety.

FIELD OF THE INVENTION

The present invention generally relates to protein—protein interactions, particularly to protein complexes formed by protein—protein interactions and methods of use thereof.

BACKGROUND OF THE INVENTION

The prolific output from numerous genomic sequencing efforts, including the Human Genome Project, is creating an ever-expanding foundation for large-scale study of protein function. Indeed, this emerging field of proteomics can appropriately be viewed as a bridge that connects DNA sequence information to the physiology and pathology of intact organisms. As such, proteomics—the large-scale study of protein function—will likely be starting point for the development of many future pharmaceuticals. The efficiency of drug development will therefore depend on the diversity and robustness of the methods used to elucidate protein function, i.e., the proteomic tools that are available.

Several approaches are generally known in the art for studying protein function. One method is to analyze the DNA sequence of a particular gene and the amino acid sequence coded by the gene in the context of sequences of genes with known functions. Generally, similar functions can be predicted based on sequence homologies. This "homology method" has been widely used, and powerful computer programs have been designed to facilitate homology analysis. See, e.g., Altschul et al., *Nucleic Acids Res.*, 25.3389–3402 (1997). However, this method is useful only when the function of a homologous protein is known.

Another useful approach is to interfere with the expression of a particular gene in a cell or organism and examine the consequent phenotypic effects. For example, Fire et al., *Nature*, 391:806–811 (1998) disclose an "RNA interference" assay in which double-stranded RNA transcripts corresponding to a particular target gene are injected into cells or organisms to determine the phenotype associated with the disrupted expression of that gene. Alternatively, transgenic technologies can be utilized to delete or "knock out" a particular gene in an organism and the effect of the gene knockout is determined. See e.g., Winzeler et al., *Science*, 285:901–906 (1999); Zambrowicz et al., *Nature*, 392:608–611 (1998). The phenotypic effects resulting from the disruption of expression of a particular gene can shed some light on the functions of the gene. However, the techniques involved are complex and the time required for a phenotype to appear can be long, especially in mammals. In addition, in many cases disruption of a particular gene may not cause any detectable phenotypic effect.

Gene functions can also be uncovered by genetic linkage analysis. For example, genes responsible for certain diseases may be identified by positional cloning. Alternatively, gene function may be inferred by comparing genetic variations among individuals in a population and correlating particular phenotypes with the genetic variations. Such linkage analyses are powerful tools, particularly when genetic variations exist in a traceable population from which samples are readily obtainable. However, readily identifiable genetic diseases are rare and samples from a large population with genetic variations are not easily accessible. In addition, it is also possible that a gene identified in a linkage analysis does not contribute to the associated disease or symptom but rather is simply linked to unknown genetic variations that cause the phenotypic defects.

With the advance of bioinformatics and publication of the full genome sequence of many organisms, computational methods have also been developed to assign protein functions by comparative genome analysis. For example, Pellegrini et al., *Proc. Natl. Acad. Sci. USA* 96:4285–4288 (1999) discloses a method that constructs a "phylogenetic profile" that summarizes the presence or absence of a particular protein across a number of organisms as determined by analyzing the genome sequences of the organisms. A protein's function is predicted to be linked to another protein's function if the two proteins share the same phylogenetic profile. Another method, the Rosetta Stone method, is based on the theory that separate proteins in one organism are often expressed as separate domains of a fusion protein in another organism. Because the separate domains in the fusion protein are predictably associated with the same function, it can be reasonably predicted that the separate proteins are associated with same functions. Therefore, by discovering separate proteins corresponding to a fusion protein, i.e., the "Rosetta Stone sequence," functional linkage between proteins can be established. See Marcotte et al., *Science*, 285:751–753 (1999); Enright et al., *Nature*, 402:86–90 (1999). Another computational method is the "gene neighbor method." See Dandekar et al., *Trends Biochem. Sci.*, 23:324–328 (1998); Overbeek et al., *Proc. Natl. Acad. Sci. USA* 96:2896–2901 (1999). This method is based on the likelihood that if two genes are found to be neighbors in several different genomes, the proteins encoded by the genes share a common function.

While the methods described above are useful in analyzing protein functions, they are constrained by various practical limitations such as unavailability of suitable samples, inefficient assay procedures, and limited reliability. The computational methods are useful in linking proteins by function. However, they are only applicable to certain proteins, and the linkage maps established therewith are sketchy. That is, the maps lack specific information that describes how proteins function in relation to each other within the functional network. Indeed, none of the methods places the identified protein functions in the context of protein—protein interactions.

In contrast with the traditional view of protein function, which focuses on the action of a single protein molecule, a modern expanded view of protein function defines a protein as an element in an interaction network. See Eisenberg et al., *Nature*, 405:823–826 (2000). That is, a full understanding of the functions of a protein will require knowledge of not only the characteristics of the protein itself, but also its interactions or connections with other proteins in the same interacting network. In essence, protein—protein interactions form the basis of almost all biological processes, and each biological process is composed of a network of interacting proteins. For example, cellular structures such as cytoskeletons, nuclear pores, centrosomes, and kinetochores are formed by complex interactions among a multitude of proteins. Many enzymatic reactions are associated with large protein complexes formed by interactions among enzymes, protein substrates, and protein modulators. In addition, protein—protein interactions are also part of the mechanisms for signal transduction and other basic cellular functions such as DNA replication, transcription, and translation. For example, the complex transcription initiation process generally requires protein—protein interactions among numerous transcription factors, RNA polymerase, and other proteins. See e.g., Tjian and Maniatis, *Cell,* 77:5–8 (1994).

Because most proteins function through their interactions with other proteins, if a test protein interacts with a known protein, one can reasonably predict that the test protein is associated with the functions of the known protein, e.g., in the same cellular structure or same cellular process as the known protein. Thus, interaction partners can provide an immediate and reliable understanding towards the functions of the interacting proteins. By identifying interacting proteins, a better understanding of disease pathways and the cellular processes that result in diseases may be achieved, and important regulators and potential drug targets in disease pathways can be identified.

There has been much interest in protein—protein interactions in the field of proteomics. A number of biochemical approaches have been used to identify interacting proteins. These approaches generally employ the affinities between interacting proteins to isolate proteins in a bound state. Examples of such methods include coimmunoprecipitation and copurification, optionally combined with cross-linking to stabilize the binding. Identities of the isolated protein interacting partners can be characterized by, e.g., mass spectrometry. See e.g., Rout et al., *J. Cell. Biol.,* 148:635–651 (2000); Houry et al., *Nature,* 402:147–154 (1999); Winter et al., *Curr. Biol.,* 7:517–529 (1997). A popular approach useful in large-scale screening is the phage display method, in which filamentous bacteriophage particles are made by recombinant DNA technologies to express a peptide or protein of interest fused to a capsid or coat protein of the bacteriophage. A whole library of peptides or proteins of interest can be expressed and a bait protein can be used to screening the library to identify peptides or proteins capable of binding to the bait protein. See e.g., U.S. Pat. Nos. 5,223,409; 5,403,484, 5,571,698; and 5,837,500. Notably, the phage display method only identifies those proteins capable of interacting in an in vitro environment, while the coimmunoprecipitation and copurification methods are not amenable to high throughput screening.

The yeast two-hybrid system is a genetic method that overcomes certain shortcomings of the above approaches. The yeast two-hybrid system has proven to be a powerful method for the discovery of specific protein interactions in vivo. See generally Bartel and Fields, eds., *The Yeast Two-Hybrid System,* Oxford University Press, New York, N.Y., 1997. The yeast two-hybrid technique is based on the fact that the DNA-binding domain and the transcriptional activation domain of a transcriptional activator contained in different fusion proteins can still activate gene transcription when they are brought into proximity to each other. In a yeast two-hybrid system, two fusion proteins are expressed in yeast cells. One has a DNA-binding domain of a transcriptional activator fused to a test protein. The other, on the other hand, includes a transcriptional activating domain of the transcriptional activator fused to another test protein. If the two test proteins interact with each other in vivo, the two domains of the transcriptional activator are brought together reconstituting the transcriptional activator and activating a reporter gene controlled by the transcriptional activator. See, e.g., U.S. Pat. No. 5,283,173.

Because of its simplicity, efficiency and reliability, the yeast two-hybrid system has gained tremendous popularity in many areas of research. In addition, yeast cells are eukaryotic cells. The interactions between mammalian proteins detected in the yeast two-hybrid system typically are bona fide interactions that occur in mammalian cells under physiological conditions. As a matter of fact, numerous mammalian protein—protein interactions have been identified using the yeast two-hybrid system. The identified proteins have contributed significantly to the understanding of many signal transduction pathways and other biological processes. For example, the yeast two-hybrid system has been successfully employed in identifying a large number of novel mammalian cell cycle regulators that are important in complex cell cycle regulations. Using known proteins that are important in cell cycle regulation as baits, other proteins involved in cell cycle control were identified by virtue of their ability to interact with the baits. See generally, Hannon et al., in *The Yeast Two-Hybrid System,* Bartel and Fields, eds., pages 183–196, Oxford University Press, New York, N.Y., 1997. Examples of mammalian cell cycle regulators identified by the yeast two-hybrid system include CDK4/CDK6 inhibitors (e.g., p16, p15, p18 and p19), Rb family members (e.g., p130), Rb phosphatase (e.g., PP1-α2), Rb-binding transcription factors (e.g., E2F-4 and E2F-5), General CDK inhibitors (e.g., p21 and p27), CAK cyclin (e.g., cyclin H), and CDK Thr161 phosphatase (e.g., KAP and CDI1). See id at page 192. "[T]he two-hybrid approach promises to be a useful tool in our ongoing quest for new pieces of the cell cycle puzzle." See id at page 193.

The yeast two-hybrid system can be employed to identify proteins that interact with a specific known protein involved in a disease pathway, and thus provide valuable understandings of the disease mechanism. The identified proteins and the protein—protein interactions in which they participate are potential targets for use in identifying new drugs for treating the disease.

SUMMARY OF THE INVENTION

It has been discovered that membrane-associated protein 17 kD (MAP17) interacts with secretory carrier membrane protein 2 (SCAMP2). The specific interaction between such proteins suggests that MAP17 and SCAMP2 are involved in common biological processes. In addition, the interactions between MAP17 and SCAMP2 will result in the formation of protein complexes both in vitro and in vivo that contain MAP17 and SCAMP2. The protein complexes formed under physiological conditions can mediate the functions and biological activities of MAP17 and SCAMP2. For example, MAP17, SCAMP2, and protein complexes containing MAP17 and SCAMP2 are involved in biological processes such as regulating cell proliferation and membrane trafficking. In addition, the protein complexes as well as MAP17 and SCAMP2 can also be used in screening assays to identify compounds capable of modulating the functions and activities of MAP17, SCAMP2, and the protein complexes containing them. The identified compounds may be useful in modulating regulating cell proliferation and membrane trafficking, and in treating or preventing diseases and disorders associated with MAP17, SCAMP2, and protein complexes comprising MAP17 and SCAMP2.

In accordance with a first aspect of the present invention, isolated protein complexes are provided comprising MAP17 and SCAMP2. In addition, homologues, derivatives, and fragments of MAP17 and of SCAMP2 may also be used in forming protein complexes. In a specific embodiment, fragments of MAP17 and SCAMP2 containing the protein domains responsible for the interaction between MAP17 and SCAMP2 are used in forming a protein complex of the present invention. In another embodiment, an interacting protein member in the protein complexes of the present invention is a fusion protein containing MAP17 or a homologue, derivative, or fragment thereof. A fusion protein containing SCAMP2 or a homologue, derivative, or fragment thereof may also be used in the protein complexes. In yet another embodiment, a protein complex is provided from a hybrid protein, which comprises MAP17 or a homologue, derivative, or fragment thereof covalently linked, directly or through a linker, to SCAMP2 or a homologue, derivative, or fragment thereof. In addition, nucleic acids encoding the hybrid protein are also encompassed by the present invention.

In yet another aspect, the present invention also provides a method for making the protein complexes. The method includes the steps of providing the first protein and the second protein in the protein complexes of the present invention and contacting said first protein with said second protein. In addition, the protein complexes can be prepared by isolation or purification from tissues and cells or produced by recombinant expression of their protein members. The protein complexes can be incorporated into a protein microchip or microarray, which are useful in large-scale high throughput screening assays involving the protein complexes.

In accordance with another aspect of the invention, antibodies are provided that are immunoreactive with a protein complex of the present invention. In one embodiment, 2.5 an antibody is selectively immunoreactive with a protein complex of the present invention. In another embodiment, a bifunctional antibody is provided that has two different antigen binding sites, each being specific to a different interacting protein member in a protein complex of the present invention. The antibodies of the present invention can take various forms including polyclonal antibodies, monoclonal antibodies, chimeric antibodies, antibody fragments such as Fv fragments, single-chain Fv fragments (scFv), Fab' fragments, and F(ab)$_2$ fragments. Preferably, the antibodies are partially or fully humanized antibodies. The antibodies of the present invention can be readily prepared using procedures generally known in the art. For example, recombinant libraries such as phage display libraries and ribosome display libraries may be used to screen for antibodies with desirable specificities. In addition, various mutagenesis techniques such as site-directed mutagenesis and PCR diversification may be used in combination with the screening assays.

The present invention also provides detection methods for determining whether there is any aberration in a patient with respect to a protein complex including MAP17 and SCAMP2. In one embodiment, the method comprises detecting an aberrant concentration of the protein complexes of the present invention. Alternatively, the concentrations of one or more interacting protein members (at the protein or cDNA or mRNA level) of a protein complex of the present invention are measured. In addition, the cellular localization, or tissue or organ distribution of a protein complex of the present invention is determined to detect any aberrant localization or distribution of the protein complex. In another embodiment, mutations in one or more interacting protein members of a protein complex of the present invention can be detected. In particular, it is desirable to determine whether the interacting protein members have any mutations that will lead to, or are associated with, changes in the functional activity of the proteins or changes in their binding affinity to other interacting protein members in forming a protein complex of the present invention. In yet another embodiment, the binding constant of the interacting protein members of one or more protein complexes is determined. A kit may be used for conducting the detection methods of the present invention. Typically, the kit contains reagents useful in any of the above-described embodiments of the detection methods, including, e.g., antibodies specific to a protein complex of the present invention or interacting members thereof, and oligonucleotides selectively hybridizable to the cDNAs or mRNAs encoding one or more interacting protein members of a protein complex. The detection methods may be useful in diagnosing a disease or disorder such as kidney, colon, breast, and lung cancers, staging the disease or disorder, or identifying a predisposition to the disease or disorder.

The present invention also provides screening methods for selecting modulators of a protein complex formed between MAP17 or a homologue, derivative or fragment thereof and SCAMP2 or a homologue, derivative, or fragment thereof. Screening methods are also provided for selecting modulators of MAP17 or SCAMP2. The compounds identified in the screening methods of the present invention can be used in preventing or ameliorating diseases or disorders such as kidney, colon, breast, and lung cancers.

Thus, test compounds may be screened in in vitro binding assays to identify compounds capable of binding a protein complex of the present invention or MAP17 or SCAMP2 or homologues, derivatives or fragments thereof. The assays may include the steps of contacting the protein complex with a test compound and detecting the interaction between the interacting partners. In addition, in vitro dissociation assays may also be employed to select compounds capable of dissociating or destabilizing the protein complexes identified in accordance with the present invention. For example, the assays may entail (1) contacting the interacting members of the protein complex with each other in the presence of a test compound; and (2) detecting the interaction between the interacting members.

In preferred embodiments, in vivo assays such as yeast two-hybrid assays and various derivatives thereof, preferably reverse two-hybrid assays, are utilized in identifying compounds that interfere with or disrupt protein—protein interactions between MAP17 or a homologue, derivative or fragment thereof and SCAMP2 or a homologue, derivative or fragment thereof. In addition, systems such as yeast two-hybrid assays are also useful in selecting compounds capable of triggering or initiating, enhancing or stabilizing protein—protein interactions between MAP17 or a homologue, derivative or fragment thereof and SCAMP2 or a homologue, derivative or fragment thereof.

In a specific embodiment, the screening method includes: (a) providing in a host cell a first fusion protein having a first protein which is MAP17 or a homologue or derivative or fragment thereof, and a second fusion protein having a second protein which is SCAMP2 or a homologue or derivative or fragment thereof, wherein a DNA binding domain is fused to one of the first and second proteins while a transcription-activating domain is fused to the other of said first and second proteins; (b) providing in the host cell a reporter gene, wherein the transcription of the reporter gene is determined by the interaction between the first protein and the second protein; (c) allowing the first and second fusion proteins to interact with each other within the host cell in the presence of a test compound; and (d) determining the presence or absence of expression of the reporter gene.

In addition, the present invention also provides a method for selecting a compound capable of modulating a protein— protein interaction between MAP17 and SCAMP2, which comprises the steps of (1) contacting a test compound with a SCAMP2 or a homologue or derivative or fragment thereof, and (2) determining whether said test compound is capable of binding said protein. In a preferred embodiment, the method further includes testing a selected test compound capable of binding said protein for its ability to interfere with a protein—protein interaction between MAP17 and SCAMP2, and optionally further testing the selected test compound capable of binding said protein for its ability to modulate cellular activities associated with MAP17 and/or SCAMP2.

The present invention also relates to a virtual screen method for providing a compound capable of modulating an interaction between the interacting members in the protein complexes of the present invention. In one embodiment, the method comprises the steps of providing atomic coordinates defining a three-dimensional structure of a protein complex of the present invention, and designing or selecting compounds capable of interfering with the interaction between said first protein and said second protein based on said atomic coordinates. In another embodiment, the method comprises the steps of providing atomic coordinates defining a three-dimensional structure of MAP17 or SCAMP2 or a fragment thereof, and designing or selecting compounds capable of binding MAP17 or SCAMP2 based on the atomic coordinates. In preferred embodiments, the method further includes testing a selected test compound for its ability to interfere with a protein—protein interaction between MAP17 and SCAMP2, and optionally further testing the selected test compound for its ability to modulate cellular activities associated with MAP17 and/or —SCAMP2.

The present invention further provides a composition having two expression vectors. One vector contains a nucleic acid encoding MAP17 or a homologue, derivative or fragment thereof. Another vector contains SCAMP2 or a homologue, derivative or fragment thereof. In addition, an expression vector is also provided containing (1) a first nucleic acid encoding MAP17 or a homologue, derivative or fragment thereof; and (2) a second nucleic acid encoding SCAMP2 or a homologue, derivative or fragment thereof.

Host cells are also provided comprising the expression vector(s). In addition, the present invention also provides a host cell having two expression cassettes. One expression cassette includes a promoter operably linked to a nucleic acid encoding MAP17 or a homologue, derivative or fragment thereof. Another expression cassette includes a promoter operably linked to a nucleic acid encoding SCAMP2 or a homologue, derivative or fragment thereof. Preferably, the expression cassettes are chimeric expression cassettes with heterologous promoters included.

In specific embodiments of the host cells or expression vectors, one of the two nucleic acids is linked to a nucleic acid encoding a DNA binding domain, and the other is linked to a nucleic acid encoding a transcription-activation domain, whereby two fusion proteins can be encoded.

In accordance with yet another aspect of the present invention, methods are provided for modulating the functions and activities of a protein complex comprising MAP17 and SCAMP2 of the present invention, or interacting protein members thereof. The methods may be used in treating or preventing diseases and disorders such as kidney, colon, breast, and lung cancers. In one embodiment, the methods comprise reducing the protein complex concentration and/or inhibiting the functional activities of the protein complex. Alternatively, the concentration and/or activity of MAP17 or SCAMP2 may be reduced or inhibited. Thus, the methods may include administering to cells or tissue in vitro or to patients an antibody specific to a protein complex or MAP17 or SCAMP2, an antisense oligonucleotide or ribozyme selectively hybridizable to a gene or mRNA encoding MAP17 or SCAMP2, or a compound identified in a screening assay of the present invention. In addition, gene therapy methods may also be used in reducing the expression of the gene(s) encoding MAP17 and/or SCAMP2.

In another embodiment, the methods for modulating the functions and activities of a protein complex comprising MAP17 and SCAMP2 of the present invention comprise increasing the concentration and/or the functional activities of the complex itself. Alternatively, the concentration and/or activity of MAP17 or SCAMP2 may be increased. Thus, MAP17 or SCAMP2, or the protein complex comprising MAP17 and SCAMP2 of the present invention may be administered directly to cells or tissue in vitro or to patients. Or, exogenous genes encoding one or more protein members of the protein complex comprising MAP17 and SCAMP2 may be introduced into cells or tissue in vitro or into patients by gene therapy techniques. In addition, a patient needing treatment or prevention may also be administered with compounds identified in a screening assay of the present invention capable of triggering or initiating, enhancing or stabilizing protein—protein interactions between MAP17 or a homologue, derivative or fragment thereof and SCAMP2, or a homologue, derivative or fragment thereof.

The present invention also provides cell and animal models in which the protein complexes comprising MAP17 and SCAMP2 identified in the present invention are in an aberrant form, e.g., increased or decreased concentration of the protein complexes, altered interaction between interacting protein members of the protein complexes, and/or altered distribution or localization (e.g., in organs, tissues, cells, or cellular compartments) of the protein complexes. Such cell and animal models are useful tools for studying the disorders and diseases caused by the protein complex aberrations and for testing various methods for treating associated diseases and disorders.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

1. Definitions

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular cross-linking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

As used herein, the term "interacting" or "interaction" means that two protein domains, fragments or complete proteins exhibit sufficient physical affinity to each other so as to bring the two "interacting" protein domains, fragments or proteins physically close to each other. An extreme case of interaction is the formation of a chemical bond that results in continual and stable proximity of the two entities. Interactions that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, van der Waals force, ionic force, covalent linkages, and combinations thereof. The state of proximity between the interaction domains, fragments, proteins or entities may be transient or permanent, reversible or irreversible. In any event, it is in contrast to and distinguishable from contact caused by natural random movement of two entities. Typically, although not necessarily, an "interaction" is exhibited by the binding between the interaction domains, fragments, proteins, or entities. Examples of interactions include specific interactions between antigen and antibody, ligand and receptor, enzyme and substrate, and the like.

An "interaction" between two protein domains, fragments or complete proteins can be determined by a number of methods. For example, an interaction can be determined by functional assays such as the two-hybrid systems. Protein-protein interactions can also be determined by various biophysical and biochemical approaches based on the affinity binding between the two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, *Microbiol. Rev.,* 59:94–123 (1995).

As used herein, the term "protein complex" means a composite unit that is a combination of two or more proteins formed by interaction between the proteins. Typically, but not necessarily, a "protein complex" is formed by the binding of two or more proteins together through specific non-covalent binding interactions. However, covalent bonds may also be present between the interacting partners. For instance, the two interacting partners can be covalently crosslinked so that the protein complex becomes more stable.

The term "protein fragment" as used herein means a polypeptide that represents a portion of a protein. When a protein fragment exhibits interactions with another protein or protein fragment, the two entities are said to interact through interaction domains that are contained within the entities.

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

The term "isolated" when used in reference to nucleic acids (which include gene sequences) of this invention is intended to mean that a nucleic acid molecule is present in a form other than found in nature in its original environment with respect to its association with other molecules. For example, since a naturally existing chromosome includes a long nucleic acid sequence, an "isolated nucleic acid" as used herein means a nucleic acid molecule having only a portion of the nucleic acid sequence in the chromosome but not one or more other portions present on the same chromosome. Thus, for example, an isolated gene typically includes no more than 5 kb, preferably no more than 2.5 kb, more preferably no more than 1 kb naturally occurring nucleic acid sequence that immediately flanks the gene in the naturally existing chromosome or genomic DNA. However, it is noted that an "isolated nucleic acid" as used herein is distinct from a clone in a conventional library such as genomic DNA library and cDNA library in that the clones in a library is still in admixture with almost all the other nucleic acids in a chromosome or a cell. An isolated nucleic acid can be in a vector. An isolated nucleic acid can also be part of a composition so long as the composition is substantially different from the nucleic acid's original natural environment. In this respect, an isolated nucleic acid can be in a semi-purified state, i.e., in a composition having certain natural cellular components, while it is substantially separated from other naturally occurring nucleic acids and can be readily detected and/or assayed by standard molecular biology techniques. Preferably, an "isolated nucleic acid" is separated from at least 50%, more preferably at least 75%, most preferably at least 90% of other naturally occurring nucleic acids.

The term "isolated nucleic acid" embraces "purified nucleic acid" which means a specified nucleic acid is in a substantially homogenous preparation of nucleic acid substantially free of other cellular components, other nucleic acids, viral materials, or culture medium, or chemical precursors or by-products associated with chemical reactions for chemical synthesis of nucleic acids. Typically, a "purified nucleic acid" can be obtained by standard nucleic acid purification methods. In a purified nucleic acid, preferably the specified nucleic acid molecule constitutes at least 75%, preferably it least 85%, and more preferably at least 95% of the total nucleic acids in the preparation. The term "purified nucleic acid" also means nucleic acids prepared from a recombinant host cell (in which the nucleic acids have been recombinantly amplified and/or expressed) or chemically synthesized nucleic acids.

The term "isolated nucleic acid" also encompasses "recombinant nucleic acid" which is used herein to mean a hybrid nucleic acid produced by recombinant DNA technology having the specified nucleic acid molecule covalently linked to one or more nucleic acid molecules that are not the nucleic acids naturally flanking the specified nucleic acid. Typically, such one or more nucleic acid molecules flanking the specified nucleic acid are no more than 50 kb, preferably no more than 25 kb.

The term "isolated polypeptide" as used herein means a polypeptide molecule is present in a form other than found in nature in its original environment with respect to its association with other molecules. Typically, an "isolated polypeptide" is separated from at least 50%, more preferably at least 75%, most preferably at least 90% of other naturally co-existing polypeptides in a cell, tissue or organism.

The term "isolated polypeptide" encompasses a "purified polypeptide" which is used herein to mean a specified polypeptide that is in a substantially homogenous preparation substantially free of other cellular components, other polypeptides, viral materials, or culture medium, or when the polypeptide is chemically synthesized, chemical precursors or by-products associated with the chemical synthesis. For a purified polypeptide, preferably the specified polypeptide molecule constitutes at least 75%, preferably at least 85%, and more preferably at least 95% of the total polypeptide in the preparation. A "purified polypeptide" can be obtained from natural or recombinant host cells by standard purification techniques, or by chemically synthesis.

The term "isolated polypeptide" also encompasses a "recombinant polypeptide" which is used herein to mean a hybrid polypeptide produced by recombinant DNA technology or chemical synthesis having a specified polypeptide molecule covalently linked to one or more polypeptide molecules that do not naturally flank the specified polypeptide.

As used herein, the term "homologue," when used in connection with a first native protein or fragment thereof that is discovered, according to the present invention, to interact with a second native protein or fragment thereof, means a polypeptide that exhibits an amino acid sequence homology and/or structural resemblance to the first native interacting protein, or to one of the interacting domains of the first native protein such that it is capable of interacting with the second native protein. Typically, a protein homologue of a native protein may have an amino acid sequence that is at least 50%, preferably at least 75%, more preferably at least 80%, 85%, 86%, 87%, 88% or 89%, even more preferably at least 90%, 91%, 92%, 93% or 94%, and most preferably 95%, 96%, 97%, 98% or 99% identical to the native protein. Examples of homologues may be the ortholog proteins of other species including animals, plants, yeast, bacteria, and the like. Homologues may also be selected by, e.g., mutagenesis in a native protein. For example, homologues may be identified by site-specific mutagenesis in combination with assays for detecting protein—protein interactions, e.g., the yeast two-hybrid system described below, as will be apparent to skilled artisans apprised of the present invention. Other techniques for detecting protein—protein interactions include, e.g., protein affinity chromatography, affinity blotting, in vitro binding assays, and the like.

For the purpose of comparing two different nucleic acid or polypeptide sequences, one sequence (test sequence) may be described to be a specific "percent identical to" another sequence (reference sequence) in the present disclosure. In this respect, when the length of the test sequence is less than 90% of the length of the reference sequence, the percentage identity is determined by the algorithm of Myers and Miller, *Bull. Math. Biol.*, 51:5–37 (1989) and Myers and Miller, *Comput. Appl. Biosci.*, 4(1):11–7 (1988). Specifically, the identity is determined by the ALIGN program, which is available at a website maintained by IGH, Montpellier, FRANCE. The default parameters are used.

Where the length of the test sequence is at least 90% of the length of the reference sequence, the percentage identity is determined by the algorithm of Karlin and Altschul, *Proc. Natl. Acad. Sci. USA*, 90:5873–77 (1993), which is incorporated into various BLAST programs. Specifically, the percentage identity is determined by the "BLAST 2 Sequences" tool, which is available at the NCBI website (National Center for Biotechnology Information). See Tatusova and Madden, *FEMS Microbiol. Lett.*, 174(2):247–50 (1999). For pairwise DNA—DNA comparison, the BLASTN 2.1.2 program is used with default parameters (Match: 1; Mismatch: −2; Open gap: 5 penalties; extension gap: 2 penalties; gap x_dropoff: 50; expect: 10; and word size: 11, with filter). For pairwise protein—protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter).

The term "derivative," when used in connection with a first native protein (or fragment thereof) that is discovered, according to the present invention, to interact with a second native protein (or fragment thereof), means a modified form of the first native protein prepared by modifying the side chain groups of the first native protein without changing the amino acid sequence of the first native protein. The modified form, i.e., the derivative should be capable of interacting with the second native protein. Examples of modified forms include glycosylated forms, phosphorylated forms, myristylated forms, ribosylated forms, ubiquitinated forms, and the like. Derivatives also include hybrid or fusion proteins containing a native protein or a fragment thereof. Methods for preparing such derivative forms should be apparent to skilled artisans. The prepared derivatives can be easily tested for their ability to interact with the native interacting partner using techniques known in the art, e.g., protein affinity chromatography, affinity blotting, in vitro binding assays, yeast two-hybrid assays, and the like.

The term "isolated protein complex" means a protein complex present in a composition or environment that is different from that found in nature—in its native or original cellular or body environment. Preferably, an "isolated protein complex" is separated from at least 50%, more preferably at least 75%, most preferably at least 90% of other naturally co-existing cellular or tissue components. Thus, an "isolated protein complex" may also be a naturally existing protein complex in an artificial preparation or a non-native host cell. An "isolated protein complex" may also be a "purified protein complex", that is, a substantially purified form in a substantially homogenous preparation substantially free of other cellular components, other polypeptides, viral materials, or culture medium, or, when the protein components in the protein complex are chemically synthesized, free of chemical precursors or by-products associated with the chemical synthesis. A "purified protein complex" typically means a preparation containing preferably at least 75%, more preferably at least 85%, and most preferably at least 95% a particular protein complex. A "purified protein complex" may be obtained from natural or recombinant host cells or other body samples by standard purification techniques, or by chemical synthesis.

The terms "hybrid protein," "hybrid polypeptide," "hybrid peptide," "fusion protein," "fusion polypeptide," and "fusion peptide" are used herein interchangeably to mean a non-naturally occurring protein having a specified polypeptide molecule covalently linked to one or more polypeptide molecules that do not naturally link to the specified polypeptide. Th us, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

The term "antibody" as used herein encompasses both monoclonal and polyclonal antibodies that fall within any antibody classes, e.g., IgG, IgM, IgA, or derivatives thereof. The term "antibody" also includes antibody fragments including, but not limited to, Fab, F(ab')$_2$, and conjugates of such fragments, and single-chain antibodies comprising an antigen recognition epitope. In addition, the term "antibody" also means humanized antibodies, including partially or fully humanized antibodies. An antibody may be obtained from an animal, or from a hybridoma cell line producing a monoclonal antibody, or obtained from cells or libraries recombinantly expressing a gene encoding a particular antibody.

The term "selectively immunoreactive" as used herein means that an antibody is reactive thus binds to a specific protein or protein complex, but not other similar proteins or fragments or components thereof.

The term "activity" when used in connection with proteins or protein complexes means any physiological or biochemical activities displayed by or associated with a particular protein or protein complex including but not limited to activities exhibited in biological processes and cellular functions, ability to interact with or bind another molecule or a moiety thereof, binding affinity or specificity to certain molecules, in vitro or in vivo stability (e.g., protein degradation rate, or in the case of protein complexes ability to maintain the form of protein complex), antigenicity and immunogenecity, enzymatic activities, etc. Such activities may be detected or assayed by any of a variety of suitable methods as will be apparent to skilled artisans.

The term "compound" as used herein encompasses all types of organic or inorganic molecules, including but not limited to proteins, peptides, polysaccharides, lipids, nucleic acids, small organic molecules, inorganic compounds, and derivatives thereof.

As used herein, the term "interaction antagonist" means a compound that interferes with, blocks, disrupts or destabilizes a protein—protein interaction; blocks or interferes with the formation of a protein complex; or destabilizes, disrupts or dissociates an existing protein complex.

The term "interaction agonist" as used herein means a compound that triggers, initiates, propagates, nucleates, or otherwise enhances the formation of a protein—protein interaction; triggers, initiates, propagates, nucleates, or otherwise enhances the formation of a protein complex; or stabilizes an existing protein complex.

Unless otherwise specified, the term "MAP17" as used herein means the human MAP17 protein. Likewise, "SCAMP2" means the human SCAMP2 protein unless otherwise specified in the present disclosure.

2. Protein Complexes

Novel protein—protein interactions have been discovered and confirmed using yeast two-hybrid systems. In particular, it has been discovered that MAP17 specifically interacts with SCAMP2. The MAP17 and SCAMP2 amino acid sequences are given in SEQ ID NO:1 and SEQ ID NO:2, respectively. Specific fragments capable of conferring interacting properties on MAP17 and SCAMP2 have also been identified, which are summarized in Table 1. The GenBank Reference Numbers for the cDNA sequences encoding MAP17, and SCAMP2 are noted in Table 1 below.

TABLE 1

Binding Regions of MAP17 and Its Interacting Partner

| Bait Protein | | | Prey Proteins | | | |
|---|---|---|---|---|---|---|
| Name and GenBank Accession No. | Amino Acid Coordinates | | Names | GenBank Accession Nos. | Amino Acid Coordinates | |
| | Start | Stop | | | Start | Stop |
| MAP17 (GenBank Accession No. U21049) | 1 | 115 | SCAMP2 | NM_005697 | 23 | 280 |

2.1. Cellular Functions of MAP17 and Disease Involvement

We have demonstrated an interaction between membrane-associated protein 17 kD (MAP17) and secretory carrier membrane protein 2 (SCAMP2) in a yeast two-hybrid search of a skeletal muscle library. MAP17 was identified by Kocher et al. (*Clinical Cancer Research*, Vol 1:1209, 1995) by differential display which selected for genes upregulated in renal cell carcinoma, compared to normal renal parenchyma. It appears to have limited tissue distribution, and in normal tissue, is only found in the kidney epithelium in significant amounts. However, it appears to be expressed in such tissues as stomach, colon, and uterus, as well. In addition, it is overexpressed in various human carcinomas originating from the colon, breast, and lung, as well as in a number of cell lines derived from tumors of these organs. Based on its expression pattern, MAP17 is thought to play a role in malignant transformation. MAP17 may be an integral membrane protein, but at any rate, it does localize to the plasma membrane at areas of cell-cell contact (Kocher et al., *Am. J. Pathol.* 149:493, 1996). These authors also showed that transfection of a colon carcinoma cell line with full length wild-type MAP17, decreased cell proliferation in vitro, and tumor growth, in vivo. Thus, MAP17 appears to play a role in regulating adhesion- or cell-cell-mediated growth. In support of this, Jaeger et al. (*J. Invest. Dermatol.* 115:375, 2000) found that MAP17 is also upregulated in keratinocytes upon loss of cell/matrix contact.

SCAMP2 protein is a member of a family of related membrane proteins which are involved in membrane trafficking and are localized on secretory and recycling vesicles. SCAMP proteins have N- and C-terminal cytoplasmic tails separated by four central transmembrane domains. SCAMP1, 2, and 3 have N-terminal NPF (Asn-Pro-Phe) repeats that are postulated to mediate protein—protein interaction with EH (Esp15 homology) domain proteins (De Beer et al., *Science* 281:1357, 1998). Most currently known EH domain proteins function in clathrin-mediated vesicle budding from the plasma membrane or the trans-Golgi complex. SCAMP proteins are ubiquitously expressed, except SCAMP5 which is brain-specific (Fernandez-Chacon and S üdhof, *J. Neurosci.* 20:7941, 2000).

As both MAP17 and SCAMP2 contain transmembrane domains, and may interact at plasma membrane interfaces, it is possible that they interact and mediate each other's functions. The interaction between MAP17 and SCAMP2 may thus have implications in regulation of tumor growth, and/or cholesterol efflux and coronary heart disease.

The interactions between MAP17 and SCAMP2 suggests that these two proteins are involved in common biological processes including, but not limited to, regulating cell proliferation and membrane trafficking, and disease pathways involving such cellular functions.

2.2. Protein Complexes

Accordingly, the present invention provides protein complexes formed between MAP17 and SCAMP2. The present invention also provides protein complexes formed by the interaction between a homologue, derivative or fragment of MAP17 and SCAMP2 in accordance with the present invention. In addition, the present invention further encompasses protein complexes including MAP17 and a homologue, derivative or fragment of SCAMP2 in accordance with the present invention. In yet another embodiment, protein complexes are provided having a homologue, derivative or fragment of MAP17 and a homologue, derivative or fragment of SCAMP2 in accordance with the present invention. In other words, one or more of the interacting protein members of a protein complex of the present invention may be a native protein or a homologue, derivative or fragment of a native protein.

SCAMP2 fragments capable of interacting with MAP17 can be identified by the combination of molecular engineering of a SCAMP2-encoding nucleic acid and a method for testing protein—protein interaction. For example, the coordinates in Table 1 can be used as starting points and various SCAMP fragments falling within the coordinates can be generated by deletions from either or both ends of the coordinates. The resulting fragments can be tested for their ability to interact with MAP17 using any methods known in the art for detecting protein—protein interactions (e.g., yeast two-hybrid method). Alternatively, various SCAMP2 fragments can be made by chemical synthesis. The SCAMP2 fragments can then be tested for its ability to interact with MAP17 using any method known in the art for detecting protein—protein interactions. Examples of such methods include protein affinity chromatography, affinity blotting, in vitro binding assays, yeast two-hybrid assays, and the like. Likewise, MAP17 fragments capable of interacting with SCAMP2 can also be identified in a similar manner.

Thus, for example, one interacting partner in the protein complexes can be a complete native MAP17, a MAP17 homologue capable of interacting with the SCAMP2, a MAP17 derivative, a derivative of the MAP17 homologue, a MAP17 fragment capable of interacting with SCAMP2 (MAP17 fragment(s) containing the coordinates shown in Table 1), a derivative of the MAP17 fragment, or a fusion protein containing (1) complete native MAP17, (2) a MAP17 homologue capable of interacting with SCAMP2 or (3) a MAP17 fragment capable of interacting with SCAMP2.

Besides native SCAMP2, useful interacting partners for MAP17 or a homologue or derivative or fragment thereof also include homologues of SCAMP2 capable of interacting with MAP17, derivatives of the native or homologue SCAMP2 capable of interacting with MAP17, fragments of the SCAMP2 capable of interacting with MAP17 (e.g., a fragment containing the identified interacting regions shown in Table 1), derivatives of the SCAMP2 fragments, or fusion proteins containing (1) a complete SCAMP2, (2) a SCAMP2 homologue capable of interacting with MAP17 or (3) a SCAMP2 fragment capable of interacting with MAP17.

In a specific embodiment of the protein complex of the present invention, two or more interacting partners (MAP17 and SCAMP2, or homologues, derivatives or fragments thereof) are directly fused together, or covalently linked together through a peptide linker, forming a hybrid protein having a single unbranched polypeptide chain. Thus, the protein complex may be formed by "intramolecular" interactions between two portions of the hybrid protein. Again, one or both of the fused or linked interacting partners in this protein complex may be a native protein or a homologue, derivative or fragment of a native protein.

As will be apparent to skilled artisans, suitable interacting fragments of a protein capable of interacting with an interacting partner of the protein can be obtained using various techniques well known in the art. For example, since the binding regions of both MAP17 and SCAMP2 are provided in Table 1, various MAP17 fragments within the binding regions of MAP17 can be made by chemical synthesis or recombinant DNA technologies. The MAP17 fragments can then be tested for its ability to interact with SCAMP2 using any method known in the art for detecting protein—protein interactions. Examples of such methods include protein affinity chromatography, affinity blotting, in vitro binding assays, yeast two-hybrid assays, and the like.

The protein complexes of the present invention can also be in a modified form. For example, an antibody selectively immunoreactive with the protein complex can be bound to the protein complex. In another example, a non-antibody modulator capable of enhancing the interaction between the interacting partners in the protein complex may be included. Alternatively, the protein members in the protein complex may be cross-linked for purposes of stabilization. Various crosslinking methods may be used. For example, a bifunctional reagent in the form of R-S-S-R' may be used in which the R and R' groups can react with certain amino acid side chains in the protein complex forming covalent linkages. See e.g., Traut et al., in Creighton ed., *Protein Function: A Practical Approach*, IRL Press, Oxford, 1989; Baird et al., *J. Biol. Chem.*, 251:6953–6962 (1976). Other useful crosslinking agents include, e.g., Denny-Jaffee reagent, a heterbiofunctional photoactivable moiety cleavable through an azo linkage (See Denny et al., *Proc. Natl. Acad. Sci. USA*, 81:5286–5290 (1984)), and $^{125}$I-[S-[N-(3-iodo-4-azidosalicyl)cysteaminyl]-2-thiopyridine], a cysteine-specific photocrosslinking reagent (see Chen et al., *Science*. 265:90–92 (1994)).

The above-described protein complexes may further include any additional components, e.g., other proteins, nucleic acids, lipid molecules, monosaccharides or polysaccharides, ions, etc.

2.3. Methods of Preparing Protein Complexes

The protein complex of the present invention can be prepared by a variety of methods. Specifically, a protein complex can be isolated directly from an animal tissue sample, preferably a human tissue sample containing the protein complex. Alternatively, a protein complex can be purified from host cells that recombinantly express the members of the protein complex. As will be apparent to a skilled artisan, a protein complex can be prepared from a tissue sample or recombinant host cells by coimmunoprecipitation using an antibody immunoreactive with an interacting protein partner, or preferably an antibody selectively immunoreactive with the protein complex as will be discussed in detail below.

The antibodies can be monoclonal or polyclonal. Coimmunoprecipitation is a commonly used method in the art for isolating or detecting bound proteins. In this procedure, generally a serum sample or tissue or cell lysate is admixed with a suitable antibody. The protein complex bound to the antibody is precipitated and washed. The bound protein complexes are then eluted.

Alternatively, immunoaffinity chromatography and immunobloting techniques may also be used in isolating the protein complexes from native tissue samples or recombinant host cells using an antibody immunoreactive with an interacting protein partner, or preferably an antibody selectively immunoreactive with the protein complex. For example, in protein immunoaffinity chromatography, the antibody is covalently or non-covalently coupled to a matrix (e.g., Sepharose), which is then packed into a column. Extract from a tissue sample, or lysate from recombinant cells is passed through the column where it contacts the antibodies attached to the matrix. The column is then washed with a low-salt solution to wash away the unbound or loosely (non-specifically) bound components. The protein complexes that are retained in the column can be then eluted from the column using a high-salt solution, a competitive antigen of the antibody, a chaotropic solvent, or sodium dodecyl sulfate (SDS), or the like. In immunoblotting, crude proteins samples from a tissue sample extract or recombinant host cell lysate are fractionated by polyacrylamide gel electrophoresis (PAGE) and then transferred to a membrane, e.g., nitrocellulose. Components of the protein complex can then be located on the membrane and identified by a variety of techniques, e.g., probing with specific antibodies.

In another embodiment, individual interacting protein partners may be isolated or purified independently from tissue samples or recombinant host cells using similar methods as described above. The individual interacting protein partners are then combined under conditions conducive to their interaction thereby forming a protein complex of the present invention. It is noted that different protein—protein interactions may require different conditions. As a starting point, for example, a buffer having 20 mM Tris-HCl, pH 7.0 and 500 mM NaCl may be used. Several different parameters may be varied, including temperature, pH, salt concentration, reducing agent, and the like. Some minor degree of experimentation may be required to determine the optimum incubation condition, this being well within the capability of one skilled in the art once apprised of the present disclosure.

In yet another embodiment, the protein complex of the present invention may be prepared from tissue samples or recombinant host cells or other suitable sources by protein affinity chromatography or affinity blotting. That is, one of the interacting protein partners is used to isolate the other interacting protein partner(s) by binding affinity thus forming protein complexes. Thus, an interacting protein partner prepared by purification from tissue samples or by recombinant expression or chemical synthesis may be bound covalently or non-covalently to a matrix, e.g., Sepharose, which is then packed into a chromatography column. The tissue sample extract or cell lysate from the recombinant cells can then be contacted with the bound protein on the matrix. A low-salt solution is used to wash off the unbound or loosely bound components, and a high-salt solution is then employed to elute the bound protein complexes in the column. In affinity blotting, crude protein samples from a tissue sample or recombinant host cell lysate can be fractionated by polyacrylamide gel electrophoresis (PAGE) and then transferred to a membrane, e.g., nitrocellulose. The purified interacting protein member is then bound to its interacting protein partner(s) on the membrane forming protein complexes, which are then isolated from the membrane.

It will be apparent to skilled artisans that any recombinant expression methods may be used in the present invention for purposes of expressing the protein complexes or individual interacting proteins. Generally, a nucleic acid encoding an interacting protein member can be introduced into a suitable host cell. For purposes of forming a recombinant protein complex within a host cell, nucleic acids encoding two or more interacting protein members should be introduced into the host cell.

Typically, the nucleic acids, preferably in the form of DNA, are incorporated into a vector to form expression vectors capable of directing the production of the interacting protein member(s) once introduced into a host cell. Many types of vectors can be used for the present invention. Methods for the construction of an expression vector for purposes of this invention should be apparent to skilled artisans apprised of the present disclosure. See generally, *Current Protocols in Molecular Biology*, Vol 2, Ed. Ausubel, et al., Greene Publish. Assoc. & Wiley Interscience, Ch. 13, 1988; Glover, *DNA Cloning*. Vol. II, IRL Press, Wash., D.C., Ch. 3, 1986; Bitter, et al., in *Methods in Enzymology* 153:516–544 (1987); *The Molecular Biology of the Yeast Saccharomyces*, Eds. Strathern et al., Cold Spring Harbor Press, Vols. I and II, 1982; and Sambrook er al., *Molecular Cloning: A Laboratory Manual*, Cold Spring Harbor Press, 1989.

Generally, the expression vectors include an expression cassette having a promoter operably linked to a DNA encoding an interacting protein member. The promoter can be a native promoter, i.e., the promoter found in naturally occurring cells to be responsible for the expression of the interacting protein member in the cells. Alternatively, the expression cassette can be a chimeric one, i.e., having a heterologous promoter that is not the native promoter responsible for the expression of the interacting protein member in naturally occurring cells. The expression vector may further include an origin of DNA replication for the replication of the vectors in host cells. Preferably, the expression vectors also include a replication origin for the amplification of the vectors in, e.g., *E. coli*, and selection marker(s) for selecting and maintaining only those host cells harboring the expression vectors. Additionally, the expression cassettes preferably also contain inducible elements, which function to control the transcription from the DNA encoding an interacting protein member. Other regulatory sequences such as transcriptional enhancer sequences and translation regulation sequences (e.g., Shine-Dalgarno sequence) can also be operably included in the expression cassettes. Termination sequences such as the polyadenylation signals from bovine growth hormone, SV40, lacZ and AcMNPV polyhedral protein genes may also be operably linked to the DNA encoding an interacting protein member in the expression cassettes. An epitope tag coding sequence for detection and/or purification of the expressed protein can also be operably linked to the DNA encoding an interacting protein member such that a fusion protein is expressed. Examples of useful epitope tags include, but are not limited to, influenza virus hemagglutinin (HA), Simian Virus 5 (V5), polyhistidine (6xHis), c-myc, lacZ, GST, and the like. Proteins with polyhistidine tags can be easily detected and/or purified with Ni affinity columns, while specific antibodies immunoreactive with many epitope tags are generally commercially available. The expression vectors may also contain components that direct the expressed protein extracellularly or to a particular intracellular compartment. Signal peptides, nuclear localization sequences, endoplasmic reticulum retention signals, mitochondrial localization sequences, myristoylation signals, palmitoylation signals, and transmembrane sequences are example of optional vector components that can determine the destination of expressed proteins. When it is desirable to express two or more interacting protein members in a single host cell, the DNA fragments encoding the interacting protein members may be incorporated into a single vector or different vectors.

The thus constructed expression vectors can be introduced into the host cells by any techniques known in the art, e.g., by direct DNA transformation, microinjection, electroporation, viral infection, lipofection, gene gun, and the like. The expression of the interacting protein members may be transient or stable. The expression vectors can be maintained in host cells in an extrachromosomal state, i.e., as self-replicating plasmids or viruses. Alternatively, the expression vectors can be integrated into chromosomes of the host cells by conventional techniques such as selection of stable cell lines or site-specific recombination. In stable cell lines, at least the expression cassette portion of the expression vector is integrated into a chromosome of the host cells.

Homologues and fragments of the native interacting protein members can also be easily expressed using the recombinant methods described above. For example, to express a protein fragment, the DNA fragment incorporated into the expression vector can be selected such that it only encodes the protein fragment. Likewise, a specific hybrid protein can be expressed using a recombinant DNA encoding the hybrid protein. Similarly, a homologue protein may be expressed from a DNA sequence encoding the homologue protein. A homologue-encoding DNA sequence may be obtained by manipulating the native protein-encoding sequence using recombinant DNA techniques. For this purpose, random or site-directed mutagenesis can be conducted using techniques generally known in the art. To make protein derivatives, for example, the amino acid sequence of a native interacting protein member may be changed in predetermined manners by site-directed DNA mutagenesis to create or remove consensus sequences for, e.g., phosphorylation by protein kinases, glycosylation, ribosylation, myristolation, palmytoylation, ubiquitination, and the like. Alternatively, non-natural amino acids can be incorporated into an interacting protein member during the synthesis of the protein in recombinant host cells. For example, photoreactive lysine derivatives can be incorporated into an interacting protein member during translation by using a modified lysyl-tRNA. See, e.g., Wiedmann et al., *Nature,* 328:830–833 (1989); Musch et al., *Cell,* 69:343–352 (1992). Other photoreactive amino acid derivatives can also be incorporated in a similar manner. See, e.g., High et al., *J. Biol. Chem.,* 368:28745–28751 (1993). Indeed, the photoreactive amino acid derivatives thus incorporated into an interacting protein member can function to cross-link the protein to its interacting protein partner in a protein complex under predetermined conditions.

In addition, derivatives of the native interacting protein members of the present invention can also be prepared by chemically linking certain moieties to amino acid side chains of the native proteins.

If desired, the homologues and derivatives thus generated can be tested to determine whether they are capable of interacting with their intended partners to form protein complexes. Testing can be conducted by e.g., the yeast two-hybrid system or other methods known in the art for detecting protein—protein interaction.

A hybrid protein as described above having MAP17 or a homologue, derivative, or fragment thereof covalently linked by a peptide bond or a peptide linker to SCAMP2 or a homologue, derivative, or fragment thereof, can be expressed recombinantly from a chimeric nucleic acid, e.g., a DNA or mRNA fragment encoding the fusion protein. Accordingly, the present invention also provides a nucleic acid encoding the hybrid protein of the present invention. In addition, an expression vector having incorporated therein a nucleic acid encoding the hybrid protein of the present invention is also provided. The methods for making such chimeric nucleic acids and expression vectors containing them should be apparent to skilled artisans apprised of the present disclosure.

2.4. Protein Microchip

In accordance with another embodiment of the present invention, a protein microchip or microarray is provided having one or more of the protein complexes and/or antibodies selectively immunoreactive with the protein complexes of the present invention. Protein microarrays are becoming increasingly important in both proteomics research and protein-based detection and diagnosis of diseases. The protein microarrays in accordance with this embodiment of the present invention will be useful in a variety of applications including, e.g., large-scale or high-throughput screening for compounds capable of binding to the protein complexes or modulating the interactions between the interacting protein members in the protein complexes.

The protein microarray of the present invention can be prepared in a number of methods known in the art. An example of a suitable method is that disclosed in MacBeath and Schreiber, *Science,* 289:1760–1763 (2000). Essentially, glass microscope slides are treated with an aldehyde-containing silane reagent (SuperAldehyde Substrates purchased from TeleChem International, Cupertino, Calif.). Nanoliter volumes of protein samples in a phosphate-buffered saline with 40% glycerol are then spotted onto the treated slides using a high-precision contact-printing robot. After incubation, the slides are immersed in a bovine serum albumin (BSA)-containing buffer to quench the unreacted aldehydes and to form a BSA layer that functions to prevent non-specific protein binding in subsequent applications of the microchip. Alternatively, as disclosed in MacBeath and Schreiber, proteins or protein complexes of the present invention can be attached to a BSA-NHS slide by covalent linkages. BSA-NHS slides are fabricated by first attaching a molecular layer of BSA to the surface of glass slides and then activating the BSA with N,N'-disuccinimidyl carbonate. As a result, the amino groups of the lysine, aspartate, and glutamate residues on the BSA are activated and can form covalent urea or amide linkages with protein samples spotted on the slides. See MacBeath and Schreiber, *Science,* 289:1760–1763 (2( )00).

Another example of a useful method for preparing the protein microchip of the present invention is that disclosed in PCT Publication Nos. WO 00/4389A2 and WO 00/04382, both of which are assigned to Zyomyx and are incorporated herein by reference. First, a substrate or chip base is covered with one or more layers of thin organic film to eliminate any surface defects, insulate proteins from the base materials, and to ensure uniform protein array. Next, a plurality of protein-capturing agents (e.g. antibodies, peptides, etc.) are arrayed and attached to the base that is covered with the thin film. Proteins or protein complexes can then be bound to the capturing agents forming a protein microarray. The protein microchips are kept in flow chambers with an aqueous solution.

The protein microarray of the present invention can also be made by the method disclosed in PCT Publication No.

WO 99/36576 assigned to Packard Bioscience Company, which is incorporated herein by reference. For example, a three-dimensional hydrophilic polymer matrix, i.e., a gel, is first dispensed on a solid substrate such as a glass slide. The polymer matrix gel is capable of expanding or contracting and contains a coupling reagent that reacts with amine groups. Thus, proteins and protein complexes can be contacted with the matrix gel in an expanded aqueous and porous state to allow reactions between the amine groups on the protein or protein complexes with the coupling reagents thus immobilizing the proteins and protein complexes on the substrate. Thereafter, the gel is contracted to embed the attached proteins and protein complexes in the matrix gel.

Alternatively, the proteins and protein complexes of the present invention can be incorporated into a commercially available protein microchip, e.g., the ProteinChip System from Ciphergen Biosystems Inc., Palo Alto, Calif. The ProteinChip System comprises metal chips having a treated surface, which interact with proteins. Basically, a metal chip surface is coated with a silicon dioxide film. The molecules of interest such as proteins and protein complexes can then be attached covalently to the chip surface via a silane coupling agent.

The protein microchips of the present invention can also be prepared with other methods known in the art, e.g., those disclosed in U.S. Pat. Nos. 6,087,102, 6,139,831, 6,087,103; PCT Publication Nos. WO 99/60156, WO 99/39210, WO 00/54046, WO 00/53625, WO 99/51773, WO 99/35289, WO 97/42507, WO 01/01142, WO 00/63694, WO 00/61806, WO 99/61148, WO 99/40434, all of which are incorporated herein by reference.

3. Antibodies

In accordance with another aspect of the present invention, an antibody immunoreactive against a protein complex of the present invention is provided. In one embodiment, the antibody is selectively immunoreactive with a protein complex of the present invention. Specifically, the phrase "selectively immunoreactive with a protein complex" as used herein means that the immunoreactivity of the antibody of the present invention with the protein complex is substantially higher than that with the individual interacting members of the protein complex so that the binding of the antibody to the protein complex is readily distinguishable from the binding of the antibody to the individual interacting member proteins based on the strength of the binding affinities. Preferably, the binding constants differ by a magnitude of at least 2 fold, more preferably at least 5 fold, even more preferably at least 10 fold, and most preferably at least 100 fold. In a specific embodiment, the antibody is not substantially immunoreactive with the interacting protein members of the protein complex.

The antibody of the present invention can be readily prepared using procedures generally known in the art. See, e.g., Harlow and Lane, *Antibodies: A Laboratory Manual*, Cold Spring Harbor Press, 1988. Typically, the protein complex against which the antibody to be generated will be immunoreactive is used as the antigen for the purpose of producing immune response in a host animal. In one embodiment, the protein complex used consists the native proteins. Preferably, the protein complex includes only the interaction domains of MAP17 and SCAMP2 involved in forming the protein complex comprising MAP17 and SCAMP2. As a result, a greater portion of the total antibodies may be selectively immunoreactive with the protein complexes. The interaction domains can be selected from, e.g., those regions summarized in Table 1. In addition, various techniques known in the art for predicting epitopes may also be employed to design antigenic peptides based on the interacting protein members in a protein complex of the present invention to increase the possibility of producing an antibody selectively immunoreactive with the protein complex. Suitable epitope-prediction computer programs include, e.g., MacVector from International Biotechnologies, Inc. and Protean from DNAStar.

In a specific embodiment, a hybrid protein as described above in Section 2.1 is used as an antigen which has MAP17 or a homologue, derivative, or fragment thereof covalently linked by a peptide bond or a peptide linker to SCAMP2 or a homologue, derivative, or fragment thereof. In a preferred embodiment, the hybrid protein consists of two interacting domains selected from the regions identified in Table 1, or homologues or derivatives thereof, covalently linked together by a peptide bond or a linker molecule.

The antibody of the present invention can be a polyclonal antibody to a protein complex of the present invention. To produce the polyclonal antibody, various animal hosts can be employed, including, e.g., mice, rats, rabbits, goats, guinea pigs, hamsters, etc. A suitable antigen which is a protein complex of the present invention or a derivative thereof as described above can be administered directly to a host animal to illicit immune reactions. Alternatively, it can be administered together with a carrier such as keyhole limpet hemocyanin (KLH), bovine serum albumin (BSA), ovalbumin, and Tetanus toxoid. Optionally, the antigen is conjugated to a carrier by a coupling agent such as carbodiimide, glutaraldehyde, and MBS. Any conventional adjuvants may be used to boost the immune response of the host animal to the protein complex antigen. Suitable adjuvants known in the art include but are not limited to Complete Freund's Adjuvant (which contains killed mycobacterial cells and mineral oil), incomplete Freund's Adjuvant (which lacks the cellular components), aluminum salts, MF59 from Biocine, monophospholipid, synthetic trehalose dicorynomycolate (TDM) and cell wall skeleton (CWS) both from Corixa Corp., Seattle, Wash., non-ionic surfactant vesicles (NISV) from Proteus International PLC, Cheshire, U.K., and saponins. The antigen preparation can be administered to a host animal by subcutaneous, intramuscular, intravenous, intradermal, or intraperitoneal injection, or by injection into a lymphoid organ.

The antibodies of the present invention may also be monoclonal. Such monoclonal antibodies may be developed using any conventional techniques known in the art. For example, the popular hybridoma method disclosed in Kohler and Milstein, *Nature*, 256:495–497 (1975) is now a well-developed technique that can be used in the present invention. See U.S. Pat. No. 4,376,110, which is incorporated herein by reference. Essentially, B-lymphocytes producing a polyclonal antibody against a protein complex of the present invention can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See generally, Harlow and Lane, *Antibodies: A Laboratory Manual*, Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In addition, antibodies selectively immunoreactive with a protein complex of the present invention may also be recombinantly produced. For example, cDNAs prepared by PCR amplification from activated B-lymphocytes or hybridomas may be cloned into an expression vector to form a cDNA library, which is then introduced into a host cell for recombinant expression. The cDNA encoding a specific desired protein may then be isolated from the library. The isolated cDNA can be introduced into a suitable host cell for the expression of the protein. Thus, recombinant techniques can be used to produce specific native antibodies, hybrid antibodies capable of simultaneous reaction with more than one antigen, chimeric antibodies (e.g., the constant and variable regions are derived from different sources), univalent antibodies that comprise one heavy and light chain pair coupled with the Fc region of a third (heavy) chain, Fab proteins, and the like. See U.S. Pat. No. 4,816,567; European Patent Publication No. 0088994; Munro, *Nature,* 312:597 (1984); Morrison, *Science,* 229:1202 (1985); Oi et al., *BioTechniques,* 4:214 (1986); and Wood et al., *Nature,* 314:446–449 (1985), all of which are incorporated herein by reference. Antibody fragments such as Fv fragments, single-chain Fv fragments (scFv), Fab' fragments, and F(ab)$_2$ fragments can also be recombinantly produced by methods disclosed in, e.g., U.S. Pat. No. 4,946,778; Skerra & Plückthun, *Science,* 240:1038–1041(1988); Better et al., *Science,* 240:1041–1043 (1988); and Bird, et al., *Science,* 242:423–426 (1988), all of which are incorporated herein by reference.

In a preferred embodiment, the antibodies provided in accordance with the present invention are partially or fully humanized antibodies. For this purpose, any methods known in the art may be used. For example, partially humanized chimeric antibodies having V regions derived from the tumor-specific mouse monoclonal antibody, but human C regions are disclosed in Morrison and Oi, *Adv. Immunol.,* 44:65–92 (1989). In addition, fully humanized antibodies can be made using transgenic non-human animals. For example, transgenic non-human animals such as transgenic mice can be produced in which endogenous immunoglobulin genes are suppressed or deleted, while heterologous antibodies are encoded entirely by exogenous immunoglobulin genes, preferably human immunoglobulin genes, recombinantly introduced into the genome. See e.g., U.S. Pat. Nos. 5,530,101; 5,545,806; 6,075,181; PCT Publication No. WO 94/02602; Green et. al., *Nat. Genetics,* 7: 13–21 (1994); and Lonberg et al., *Nature* 368: 856–859 (1994), all of which are incorporated herein by reference. The transgenic non-human host animal may be immunized with suitable antigens such as a protein complex of the present invention or one or more of the interacting protein members thereof to illicit specific immune response thus producing humanized antibodies. In addition, cell lines producing specific humanized antibodies can also be derived from the immunized transgenic non-human animals. For example, mature B-lymphocytes obtained from a transgenic animal producing humanized antibodies can be fused to myeloma cells and the resulting hybridoma clones may be selected for specific humanized antibodies with desired binding specificities. Alternatively, cDNAs may be extracted from mature B-lymphocytes and used in establishing a library that is subsequently screened for clones encoding humanized antibodies with desired binding specificities.

In yet another embodiment, a bifunctional antibody is provided that has two different antigen binding sites, each being specific to a different interacting protein member in a protein complex of the present invention. The bifunctional antibody may be produced using a variety of methods known in the art. For example, two different monoclonal antibody-producing hybridomas can be fused together. One of the two hybridomas may produce a monoclonal antibody specific against an interacting protein member of a protein complex of the present invention, while the other hybridoma generates a monoclonal antibody immunoreactive with another interacting protein member of the protein complex. The thus formed new hybridoma produces different antibodies including a desired bifunctional antibody, i.e., an antibody immunoreactive with both of the interacting protein members. The bifunctional antibody can be readily purified. See Milstein and Cuello, *Nature,* 305:537–540 (1983).

Alternatively, a bifunctional antibody may also be produced using heterobifunctional crosslinkers to chemically link two different monoclonal antibodies, each being immunoreactive with a different interacting protein member of a protein complex. Therefore, the aggregate will bind to two interacting protein members of the protein complex. See Staerz et al, *Nature,* 314:628–631(1985); Perez el at, *Nature,* 316:354–356 (1985).

In addition, bifunctional antibodies can also be produced by recombinantly expressing light and heavy chain genes in a hybridoma that itself produces a monoclonal antibody. As a result, a mixture of antibodies including a bifunctional antibody is produced. See DeMonte et al, *Proc. Natl. Acad. Sci., USA,* 87:2941–2945 (1990); Lenz and Weidle, *Gene,* 87:213–218 (1990).

Preferably, a bifunctional antibody in accordance with the present invention is produced by the method disclosed in U.S. Pat. No. 5,582,996, which is incorporated herein by reference. For example, two different Fabs can be provided and mixed together. The first Fab can bind to an interacting protein member of a protein complex, and has a heavy chain constant region having a first complementary domain not naturally present in the Fab but capable of binding a second complementary domain. The second Fab is capable of binding another interacting protein member of the protein complex, and has a heavy chain constant region comprising a second complementary domain not naturally present in the Fab but capable of binding to the first complementary domain. Each of the two complementary domains is capable of stably binding to the other but not to itself. For example, the leucine zipper regions of c-fos and c-jun oncogenes may be used as the first and second complementary domains. As a result, the first and second complementary domains interact with each other to form a leucine zipper thus associating the two different Fabs into a single antibody construct capable of binding to two antigenic sites.

Other suitable methods known in the art for producing bifunctional antibodies may also be used, which include those disclosed in Holliger et al., *Proc. Nat'l Acad. Sci. USA,* 90:6444–6448 (1993); de Kruif et al., *J. Biol. Chem.,* 271:7630–7634 (1996); Coloma and Morrison, *Nat. Biotechnol.,* 15:159–163 (1997); Muller et al., *FEBS Lett.,* 422:259–264 (1998); and Muller et al., *FEBS Lett.,* 432:45–49 (1998), all of which are incorporated herein by reference.

4. Methods of Detecting Protein Complexes

Another aspect of the present invention relates to methods for detecting the protein complexes of the present invention, particularly for determining the concentration of a specific protein complex in a patient sample.

In one embodiment, the concentration of a protein complex having MAP17 and SCAMP2 is determined in cells, tissue, or an organ of a patient. For example, the protein complex can be isolated or purified from a patient sample obtained from cells, tissue, or an organ of the patient and the amount thereof is determined. As described above, the protein complex can be prepared from a cells, tissue or an organ sample by coimmunoprecipitation using an antibody immunoreactive with an interacting protein member, a bifunctional antibody that is immunoreactive with two or more interacting protein members of the protein complex, or preferably an antibody selectively immunoreactive with the protein complex. When bifunctional antibodies or antibodies immunoreactive with only free interacting protein members are used, individual interacting protein members not complexed with other proteins may also be isolated along with the protein complex containing such individual proteins. However, they can be readily separated from the protein complex using methods known in the art, e.g., size-based separation methods such as gel filtration, or by subtracting the protein complex from the mixture using an antibody specific against another individual interacting protein member. Additionally, proteins in a sample can be separated in a gel such as polyacrylamide gel and subsequently immunoblotted using an antibody immunoreactive with the protein complex.

Alternatively, the concentration of the protein complex can be determined in a sample without separation, isolation or purification. For this purpose, it is preferred that an antibody selectively immunoreactive with the specific protein complex is used in an immunoassay. For example, immunocytochemical methods can be used. Other well known antibody-based techniques can also be used including, e.g., enzyme-linked immunosorbent assay (ELISA), radioimmunoassay (RIA), immunoradiometric assays (IRMA), fluorescent immunoassays, protein A immunoassays, and immunoenzymatic assays (EMA). See e.g., U.S. Pat. Nos. 4,376,110 and 4,486,530, both of which are incorporated herein by reference.

In addition, since a specific protein complex is formed from its interacting protein members, if one of the interacting protein members is at a relatively low concentration in a patient, it may be reasonably expected that the concentration of the protein complex in the patient may also be low. Therefore, the concentration of an individual interacting protein member of a specific protein complex can be determined in a patient sample which can then be used as a reasonably accurate indicator of the concentration of the protein complex in the sample. For this purpose, antibodies against an individual interacting protein member of a specific complex can be used in any one of the methods described above. In a preferred embodiment, the concentration of each of the interacting protein members of a protein complex is determined in a patient sample and the relative concentration of the protein complex is then deduced.

In addition, the relative protein complex concentration in a patient can also be determined by determining the concentration of the mRNA encoding an interacting protein member of the protein complex. Preferably, each interacting protein member's mRNA concentration in a patient sample is determined. For this purpose, methods for determining mRNA concentration generally known in the art may all be used. Examples of such methods include, e.g., Northern blot assay, dot blot assay, PCR assay (preferably quantitative PCR assay), in situ hybridization assay, and the like.

As discussed above, the interactions between MAP17 and SCAMP2 suggests that these proteins and/or the protein complexes formed by such proteins may be involved in common biological processes and disease pathways. In addition, the interactions between MAP17 and SCAMP2 under physiological conditions may lead to the formation of protein complexes in vivo that contain MAP17 and SCAMP2. The protein complexes are expected to mediate the functions and biological activities of MAP17 and SCAMP2. For example, MAP17 and SCAMP2 maybe involved in regulating cell proliferation and membrane trafficking and associated with diseases and disorders such as kidney, colon, breast, and lung cancers. Thus, aberrations in the concentration and/or activity of the protein complexes comprising MAP17 and SCAMP2, and/or the individual proteins, MAP17 and SCAMP2, may result in diseases or disorders such as kidney, colon, breast, and lung cancers. Thus, the aberration in the protein complexes or the individual proteins and the degree of the aberration may be indicators for the diseases or disorders. These aberrations may be used as parameters for classifying and/or staging one of the above-described diseases. In addition, they may also be indicators for patients' response to a drug therapy.

Association between a physiological state (e.g., physiological disorder, predisposition to the disorder, a disease state, response to a drug therapy, or other physiological phenomena or phenotypes) and a specific aberration in a protein complex of the present invention or an individual interacting member thereof can be readily determined by comparative analysis of the protein complex and/or the interacting members thereof in a normal population and an abnormal or affected population. Thus, for example, one can study the concentration, localization and distribution of a particular protein complex, mutations in the interacting protein members of the protein complex, and/or the binding affinity between the interacting protein members in both a normal population and a population affected with a particular physiological disorder described above. The study results can be compared and analyzed by statistical means. Any detected statistically significant difference in the two populations would indicate an association. For example, if the concentration of the protein complex is statistically significantly higher in the affected population than in the normal population, then it can be reasonably concluded that higher concentration of the protein complex is associated with the physiological disorder.

Thus, once an association is established between a particular type of aberration in a particular protein complex of the present invention or in an interacting protein member thereof and a physiological disorder or disease or predisposition to the physiological disorder or disease, then the particular physiological disorder or disease or predisposition to the physiological disorder or disease can be diagnosed or detected by determining whether a patient has the particular aberration.

Accordingly, the present invention also provides a method for diagnosing in a patient a disease or physiological disorder, or a predisposition to the disease or disorder, such as kidney, colon, breast, and lung cancers by determining whether there is any aberration in the patient with respect to a protein complex having a first protein which is MAP17 interacting with a second protein which is SCAMP2. The same protein complex is analyzed in a normal individual and is compared with the results obtained in the patient. In this manner, any protein complex aberration in the patient can be detected. As used herein, the term "aberration" when used in the context of protein complexes of the present invention means any alterations of a protein complex including increased or decreased concentration of the protein complex in a particular cell or tissue or organ or the total body, altered localization of the protein complex in cellular compartments or in locations of a tissue or organ, changes in binding affinity of an interacting protein member of the protein complex, mutations in an interacting protein member or the gene encoding the protein, and the like. As will be apparent to a skilled artisan, the term "aberration" is used in a relative sense. That is, an aberration is relative to a normal condition.

As used herein, the term "diagnosis" means detecting a disease or disorder or determining the stage or degree of a disease or disorder. The term "diagnosis" also encompasses detecting a predisposition to a disease or disorder, determining the therapeutic effect of a drug therapy, or predicting the pattern of response to a drug therapy or xenobiotics. The diagnosis methods of the present invention may be used independently, or in combination with other diagnosing and/or staging methods known in the medical art for a particular disease or disorder.

Thus, in one embodiment, the method of diagnosis is conducted by detecting, in a patient, the concentrations of one or more protein complexes of the present invention using any one of the methods described above, and determining whether the patient has an aberrant concentration of the protein complexes.

The diagnosis may also be based on the determination of the concentrations of one or more interacting protein members (at the protein, cDNA or mRNA level) of a protein complex of the present invention. An aberrant concentration of an interacting protein member may indicate a physiological disorder or a predisposition to a physiological disorder.

In another embodiment, the method of diagnosis comprises determining, in a patient, the cellular localization, or tissue or organ distribution of a protein complex of the present invention and determining whether the patient has an aberrant localization or distribution of the protein complex. For example, immunocytochemical or immunohistochemical assays can be performed on a cell, tissue or organ sample from a patient using an antibody selectively immunoreactive with a protein complex of the present invention. Antibodies immunoreactive with both an individual interacting protein member and a protein complex containing the protein member may also be used, in which case it is preferred that antibodies immunoreactive with other interacting protein members are also used in the assay. In addition, nucleic acid probes may also be used in in situ hybridization assays to detect the localization or distribution of the mRNAs encoding the interacting protein members of a protein complex. Preferably, the mRNA encoding each interacting protein member of a protein complex is detected concurrently.

In yet another embodiment, the method of diagnosis of the present invention comprises detecting any mutations in one or more interacting protein members of a protein complex of the present invention. In particular, it is desirable to determine whether the interacting protein members have any mutations that will lead to, or are associated with, changes in the functional activity of the proteins or changes in their binding affinity to other interacting protein members in forming a protein complex of the present invention. Examples of such mutations include but are not limited to, e.g., deletions, insertions and rearrangements in the genes encoding the protein members, and nucleotide or amino acid substitutions and the like. In a preferred embodiment, the domains of the interacting protein members that are responsible for the protein—protein interactions, and lead to protein complex formation, are screened to detect any mutations therein. For example, genomic DNA or cDNA encoding an interacting protein member can be prepared from a patient sample, and sequenced. The thus obtained sequence may be compared with known wild-type sequences to identify any mutations. Alternatively, an interacting protein member may be purified from a patient sample and analyzed by protein sequencing or mass spectrometry to detect any amino acid sequence changes. Any methods known in the art for detecting mutations may be used, as will be apparent to skilled artisans apprised of the present disclosure.

In another embodiment, the method of diagnosis includes determining the binding constant of the interacting protein members of one or more protein complexes. For example, the interacting protein members can be obtained from a patient by direct purification or by recombinant expression from genomic DNAs or cDNAs prepared from a patient sample encoding the interacting protein members. Binding constants represent the strength of the protein—protein interaction between the interacting protein members in a protein complex. Thus, by measuring binding constant, subtle aberration in binding affinity may be detected.

A number of methods known in the art for estimating and determining binding constants in protein—protein interactions are reviewed in Phizicky and Fields, et al., *Microbiol. Rev.,* 59:94–123 (1995), which is incorporated herein by reference. For example, protein affinity chromatography may be used. First, columns are prepared with different concentrations of an interacting protein member which is covalently bound to the columns. Then a preparation of an interacting protein partner is run through the column and washed with buffer. The interacting protein partner bound to the interacting protein member linked to the column is then eluted. Binding constant is then estimated based on the concentrations of the bound protein and the eluted protein. Alternatively, the method of sedimentation through gradients monitors the rate of sedimentation of a mixture of proteins through gradients of glycerol or sucrose. At concentrations above the binding constant, proteins can sediment as a protein complex. Thus, binding constant can be calculated based on the concentrations. Other suitable methods known in the art for estimating binding constant include but are not limited to gel filtration column such as nonequilibrium "small-zone" gel filtration columns (See e.g., Gill et al., *J. Mol. Biol.,* 220:307–324 (1991)), the Hummel-Dreyer method of equilibrium gel filtration (See e.g., Hummel and Dreyer, *Biochim. Biophys. Acta,* 63:530–532 (1962)) and large-zone equilibrium gel filtration (See e.g., Gilbert and Kellett, *J. Biol. Chem.,* 246:6079–6086 (1971)), sedimentation equilibrium (See e.g., Rivas and Minton, *Trends Biochem.,* 18:284–287 (1993)), fluorescence methods such as fluorescence spectrum (See e.g., Otto-Bruc et al, *Biochemistry,* 32:8632–8645 (1993)) and fluorescence polarization or anisotropy with tagged molecules (See e.g., Weiel and Hershey, *Biochemistry,* 20:5859–5865 (1981)), solution equilibrium measured with immobilized binding protein (See e.g., Nelson and Long, *Biochemistry,* 30:2384–2390 (1991)), and surface plasmon resonance (See e.g., Panayotou et al., *Mol. Cell. Biol.,* 13:3567–3576 (1993)).

In another embodiment, the diagnosis method of the present invention comprises detecting protein—protein interactions in functional assay systems such as the yeast two-hybrid system. Accordingly, to determine the protein—protein interaction between two interacting protein members that normally form a protein complex in normal individuals, cDNAs encoding the interacting protein members can be isolated from a patient to be diagnosed. The thus cloned cDNAs or fragments thereof can be subcloned into vectors for use in yeast two-hybrid system. Preferably a reverse yeast two-hybrid system is used such that failure of interaction between the proteins may be positively detected. The use of yeast two-hybrid system or other systems for detecting protein—protein interactions is known in the art and is described below in Section 5.3.1.

A kit may be used for conducting the diagnosis methods of the present invention. Typically, the kit should contain, in a carrier or compartmentalized container, reagents useful in any of the above-described embodiments of the diagnosis method. The carrier can be a container or support, in the form of, e.g., bag, box, tube, rack, and is optionally compartmentalized. The cannier may define an enclosed confinement for safety purposes during shipment and storage. In one embodiment, the kit includes an antibody selectively immunoreactive with a protein complex of the present invention. In addition, antibodies against individual interacting protein members of the protein complexes may also be included. The antibodies may be labeled with a detectable marker such as radioactive isotopes, or enzymatic or fluorescence markers. Alternatively secondary antibodies such as labeled anti-IgG and the like may be included for detection purposes. Optionally, the kit can include one or more of the protein complexes of the present invention prepared or purified from a normal individual or an individual afflicted with a physiological disorder associated with an aberration in the protein complexes or an interacting protein member thereof. In addition, the kit may further include one or more of the interacting protein members of the protein complexes of the present invention prepared or purified from a normal individual or an individual afflicted with a physiological disorder associated with an aberration in the protein complexes or an interacting protein member thereof. Suitable oligonucleotide primers useful in the amplification of the genes or cDNAs for the interacting protein members may also be provided in the kit. In particular, in a preferred embodiment, the kit includes a first oligonucleotide selectively hybridizable to the mRNA or cDNA encoding MAP17 and a second oligonucleotide selectively hybridizable to the mRNA or cDNA encoding SCAMP2. Additional oligonucleotides hybridizing to a region of the gene encoding MAP17 and/or a region of the gene encoding its interaction partner, SCAMP2, as identified in the present invention, may also be included. Such oligonucleotides may be used as PCR primers for, e.g., quantitative PCR amplification of mRNAs encoding MAP17 and an interacting partner thereof, or as hybridizing probes for detecting the mRNAs. The oligonucleotides may have a length of from about 8 nucleotides to about 100 nucleotides, preferably from about 12 to about 50 nucleotides, and more preferably from about 15 to about 30 nucleotides. In addition, the kit may also contain oligonucleotides that can be used as hybridization probes for detecting the cDNAs or mRNAs encoding the interacting protein members. Preferably, instructions for using the kit or reagents contained therein are also included in the kit.

5. Use of Protein Complexes or Interacting Protein Members Thereof in Screening Assays for Modulators Protein complexes comprising MAP17 and SCAMP2, or MAP17 separately and/or SCAMP2 separately, can be used in screening assays to identify modulators of protein complexes comprising MAP17, or MAP17 separately and/or SCAMP2 separately. In addition, homologues, derivatives and fragments of MAP17, homologues, derivatives and fragments of SCAMP2, and protein complexes containing such homologues, derivatives and fragments may also be used in such screening assays. As used herein, the term "modulator" encompasses any compounds that can cause any forms of alteration of the biological activities or functions of the proteins or protein complexes, including, e.g., enhancing or reducing their biological activities, increasing or decreasing their stability, altering their affinity or specificity to certain other biological molecules, etc. In addition, the term "modulator" as used herein also includes any compounds that simply bind MAP17, SCAMP2, and/or the proteins complexes of the present invention. For example, a modulator can be an "interaction antagonist" capable of interfering with or disrupting or dissociating protein—protein interaction between MAP17 or a homologue, fragment or derivative thereof and SCAMP2 or a homologue, fragment or derivative thereof. A modulator can also be an "interaction agonist" that initiates or strengthens the interaction between the protein members of the protein complex of the present invention, or homologues, fragments or derivatives thereof.

Accordingly, the present invention provides screening methods for selecting modulators of MAP17 or a mutant form thereof, or SCAMP2 or a mutant form thereof, or protein complexes formed between MAP17 or a mutant form thereof and SCAMP2 or a mutant form thereof. The protein complex targets suitable in the screening assays of the present invention can be any embodiments of the protein complexes of the present invention as described in Section 2. Preferably, protein fragments are used in forming the protein complexes. In specific embodiments, fusion proteins are used in which a detectable epitope tag is fused to an interacting protein or a homologue or derivative or fragment thereof. Suitable examples of such epitope tags include sequences derived from, e.g., influenza virus hemagglutinin (HA), Simian Virus 5 (V5), polyhistidine (6×His), c-myc, lacZ, GST, and the like. In addition, an interacting protein alone or a homologue or derivative or fragment thereof can also be used as a protein target in screening assays. Preferably, a detectable epitope tag is fused to the protein target. For example, compounds capable of binding to MAP17 protein or a homologue or derivative or fragment thereof selected by the screening assays can be tested for their ability to inhibit or interfere with the interactions between MAP17 and SCAMP2.

The selected compounds can be tested for their ability to modulate (interfere with or strengthen) the interaction between the interacting partners within the protein complexes of the present invention. In addition, the compounds can also be further tested for their ability to modulate (inhibit or enhance) cellular functions such as regulating cell proliferation and membrane trafficking in cells as well as their effectiveness in treating diseases such as kidney, colon, breast, and lung cancers.

The modulators selected in accordance with the screening methods of the present invention can be effective in modulating the functions or activities of MAP17 alone, SCAMP2 alone, or the protein complexes of the present invention comprising MAP17 and SCAMP2. For example, compounds capable of binding the protein complexes may be capable of modulating the functions of the protein complexes. Additionally, compounds that interfere with, weaken, dissociate or disrupt, or alternatively, initiate, facilitate or stabilize the protein-protein interaction between the interacting protein members of the protein complexes can also be effective in modulating the functions or activities of the protein complexes. Thus, the compounds identified in the screening methods of the present invention can be made into therapeutically or prophylactically effective drugs for preventing or ameliorating diseases, disorders or symptoms caused by or associated with protein complexes comprising MAP17 and SCAMP2, or MAP17 separately or SCAMP2 separately. Alternatively, they may be used as leads to aid the design and identification of therapeutically or prophylactically effective compounds for diseases, disorders or symptoms caused by or associated with protein complexes comprising MAP17 and SCAMP2, or MAP17 separately or SCAMP2 separately. The protein complexes and/or interacting protein members thereof in accordance with the present invention can be used in any of a variety of drug screening techniques. Drug screening can be performed as described herein or using well-known techniques, such as those described in U.S. Pat. Nos. 5,800,998 and 5,891,628, both of which are incorporated herein by reference.

5.1. Test Compounds

Any test compounds may be screened in the screening assays of the present invention to select modulators of protein complexes of the present invention comprising MAP17 and SCAMP2, and/or MAP17 separately, and/or SCAMP2 separately. By the term "selecting" or "select" modulators it is intended to encompass both (a) choosing compounds from a group previously unknown to be modulators of MAP17, and/or SCAMP2 and/or protein complexes of the present invention comprising MAP17 and SCAMP2, and (b) testing compounds that are known to be capable of binding, or modulating the functions and activities of MAP17, and/or SCAMP2 and/or protein complexes of the present invention comprising MAP17 and SCAMP2. Both types of compounds are generally referred to herein as "test compounds." The test compounds may include, by way of example, proteins (e.g., antibodies, small peptides, artificial or natural proteins), nucleic acids, and derivatives, mimetics and analogs thereof, and small organic molecules having a molecular weight of no greater than 10,000 daltons, more preferably less than 5,000 daltons. Preferably, the test compounds are provided in library formats known in the art, e.g., in chemically synthesized libraries, recombinantly expressed libraries (e.g., phage display libraries), and in vitro translation-based libraries (e.g., ribosome display libraries).

For example, the screening assays of the present invention can be used in the antibody production processes described in Section 3 to select antibodies with desirable specificities. Various forms antibodies or derivatives thereof may be screened, including but not limited to, polyclonal antibodies, monoclonal antibodies, bifunctional antibodies, chimeric antibodies, single chain antibodies, antibody fragments such as Fv fragments, single-chain Fv fragments (scFv), Fab' fragments, and F(ab')$_2$ fragments, and various modified forms of antibodies such as catalytic antibodies, and antibodies conjugated to toxins or drugs, and the like. The antibodies can be of any types such as IgG, IgE, IgA, or IgM. Humanized antibodies are particularly preferred. Preferably, the various antibodies and antibody fragments may be provided in libraries to allow large-scale high throughput screening. For example, expression libraries expressing antibodies or antibody fragments may be constructed by a method disclosed, e.g., in Huse et al., Science, 246:1275–1281 (1989), which is incorporated herein by reference. Single-chain Fv (scFv) antibodies are of particular interest in diagnostic and therapeutic applications. Methods for providing antibody libraries are also provided in U.S. Pat. Nos. 6,096,551; 5,844,093; 5,837,460; 5,789,208; and 5,667,988, all of which are incorporated herein by reference.

Peptidic test compounds may be peptides having L-amino acids and/or D-amino acids, phosphopeptides, and other types of peptides. The screened peptides can be of any size, but preferably have less than about 50 amino acids. Smaller peptides are easier to deliver into a patient's body. Various forms of modified peptides may also be screened. Like antibodies, peptides can also be provided in, e.g., combinatorial libraries. See generally, Gallop et al., J. Med. Chem., 37:1233–1251 (1994). Methods for making random peptide libraries are disclosed in, e.g., Devlin et al., Science, 249:404–406 (1990). Other suitable methods for constructing peptide libraries and screening peptides therefrom are disclosed in, e.g., Scott and Smith, Science, 249:386–390 (1990); Moran et al., J. Am. Chem. Soc., 117:10787–10788 (1995) (a library of electronically tagged synthetic peptides); Stachelhaus et al., Science, 269:69–72 (1995); U.S. Pat. Nos. 6,156,511; 6,107,059; 6,015,561; 5,750,344; 5,834,318; 5,750,344, all of which are incorporated herein by reference. For example, random-sequence peptide phage display libraries may be generated by cloning synthetic oligonucleotides into the gene III or gene VIII of an E. coli. filamentous phage. The thus generated phage can propagate in E. coli and express peptides encoded by the oligonucleotides as fusion proteins on the surface of the phage. Scott and Smith, Science, 249:368–390 (1990). Alternatively, the "peptides on plasmids" method may also be used to form peptide libraries. In this method, random peptides may be fused to the C-terminus of the E. coli. Lac repressor by recombinant technologies and expressed from a plasmid that also contains Lac repressor-binding sites. As a result, the peptide fusions bind to the same plasmid that encodes them.

Small organic or inorganic non-peptide non-nucleotide compounds are preferred test compounds for the screening assays of the present invention. They too can be provided in a library format. See generally, Gordan et al. J. Med. Chem., 37:1385–1401 (1994). For example, benzodiazepine libraries are provided in Bunin and Ellman, J. Am. Chem. Soc., 114: 10997–10998 (1992), which is incorporated herein by reference. A method for constructing and screening peptoid libraries are disclosed in Simon et al., Proc. Natl. Acad. Sci. USA. 89:9367–9371 (1992). Methods for the biosynthesis of novel polyketides in a library format are described in McDaniel et at, Science, 262:1546–1550 (1993) and Kao et al., Science, 265:509–512 (1994). Various libraries of small organic molecules and methods of construction thereof are disclosed in U.S. Pat. No. 6,162,926 (multiply-substituted fullerene derivatives); U.S. Pat. No. 6,093,798 (hydroxamic acid derivatives); U.S. Pat. No. 5,962,337 (combinatorial 1,4-benzodiazepin-2,5-dione library); U.S. Pat. No. 5,877, 278 (Synthesis of N-substituted oligomers); U.S. Pat. No. 5,866,341 (compositions and methods for screening drug libraries); U.S. Pat. No. 5,792,821 (polymerizable cyclodextrin derivatives); U.S. Pat. No. 5,766,963 (hydroxypropylamine library); and U.S. Pat. No. 5,698,685 (morpholino-subunit combinatorial library), all of which are incorporated herein by reference.

Other compounds such as oligonucleotides and peptide nucleic acids (PNA), and analogs and derivatives thereof may also be screened to identify clinically useful compounds. Combinatorial libraries of oligonucleotides are also known in the art. See Gold et al., J. Biol. Chem., 270:13581–13584 (1995).

5.2. In Vitro Screening Assays

The test compounds may be screened in an in vitro assay to identify compounds capable of binding the protein complexes or interacting protein members thereof in accordance with the present invention. For this purpose, a test compound is contacted with a protein complex or an interacting protein member thereof under conditions and for a time sufficient to allow specific interaction between the test compound and the target components to occur and thus binding of the compound to the target forming a complex. Subsequently, the binding event is detected.

Various screening techniques known in the art may be used in the present invention. The protein complexes and the interacting protein members thereof may be prepared by any suitable methods, e.g., by recombinant expression and purification. The protein complexes and/or interacting protein members thereof (both are referred to as "target" hereinafter in this section) may be free in solution. A test compound may be mixed with a target forming a liquid mixture. The compound may be labeled with a detectable marker. Upon mixing under suitable conditions, the binding complex having the compound and the target may be co-immunoprecipitated and washed. The compound in the precipitated complex may be detected based on the marker on the compound.

In a preferred embodiment, the target is immobilized on a solid support or on a cell surface. Preferably, the target can be arrayed into a protein microchip in a method described in Section 2.3. For example, a target may be immobilized directly onto a microchip substrate such as glass slides or onto a multi-well plates using non-neutralizing antibodies, i.e., antibodies capable of binding to the target but do not substantially affect its biological activities. To affect the screening, test compounds can be contacted with the immobilized target to allow binding to occur to form complexes under standard binding assay conditions. Either the targets or test compounds are labeled with a detectable marker using well-known labeling techniques. For example, U.S. Pat. No. 5,741,713 discloses combinatorial libraries of biochemical compounds labeled with NMR active isotopes. To identify binding compounds, one may measure the formation of the target-test compound complexes or kinetics for the formation thereof. When combinatorial libraries of organic non-peptide non-nucleic acid compound are screened, it is preferred that labeled or encoded (or "tagged") combinatorial libraries are used to allow rapid decoding of lead structures. This is especially important because, unlike biological libraries, individual compounds found in chemical libraries cannot be amplified by self-amplification. Tagged combinatorial libraries are provided in, e.g., Borchardt and Still, *J. Am. Chem. Soc.*, 116:373–374 (1994) and Moran et al., *J. Am. Chem. Soc.*, 117:10787–10788 (1995), both of which are incorporated herein by reference.

Alternatively, the test compounds can be immobilized on a solid support, e.g., forming a microarray of test compounds. The target protein or protein complex is then contacted with the test compounds. The target may be labeled with any suitable detection marker. For example, the target may be labeled with radioactive isotopes or fluorescence marker before binding reaction occurs. Alternatively, after the binding reactions, antibodies that are immunoreactive with the target and are labeled with radioactive materials, fluorescence markers, enzymes, or labeled secondary anti-Ig antibodies may be used to detect any bound target thus identifying the binding compound. One example of this embodiment is the protein probing method. That is, the target provided in accordance with the present invention is used as a probe to screen expression libraries of proteins or random peptides. The expression libraries can be phage display libraries, in vitro translation-based libraries, or ordinary expression cDNA libraries. The libraries may be immobilized on a solid support such as nitrocellulose filters. See e g, Sikela and Hahn, *Proc. Natl. Acad. Sci. USA*, 84:3038–3042 (1987). The probe may be labeled with a radioactive isotope or a fluorescence marker. Alternatively, the probe can be biotinylated and detected with a streptavidin-alkaline phosphatase conjugate. More conveniently, the bound probe may be detected with an antibody.

In yet another embodiment, a known ligand capable of binding to the target can be used in competitive binding assays. Complexes between the known ligand and the target can be formed and then contacted with test compounds. The ability of a test compound to interfere with the interaction between the target and the known ligand is measured. One exemplary ligand is an antibody capable of specifically binding the target. Particularly, such an antibody is especially useful for identifying peptides that share one or more antigenic determinants of the target protein complex or interacting protein members thereof.

In a specific embodiment, a protein complex used in the screening assay includes a hybrid protein as described in Section 2.1, which is formed by fusion of two interacting protein members or fragments or interaction domains thereof. The hybrid protein may also be designed such that it contains a detectable epitope tag fused thereto. Suitable examples of such epitope tags include sequences derived from, e.g., influenza virus hemagglutinin (HA), Simian Virus 5 (V5), polyhistidine (6×His), c-myc, lacZ, GST, and the like.

Test compounds may also be screened in in vitro assays to identify compounds capable of dissociating the protein complexes identified in accordance with the present invention. Thus, for example, dissociation of a protein complex comprising MAP17 and SCAMP2 following treatment with a test compound can be detected. Conversely, test compounds may also be screened to identify compounds capable of enhancing the interaction between MAP17 and SCAMP2 or stabilizing the protein complex formed by the two proteins.

The assay can be conducted in similar manners as the binding assays described above. For example, the presence or absence of a particular protein complex can be detected by an antibody selectively immunoreactive with the protein complex. Thus, after incubation of the protein complex with a test compound, an immunoprecipitation assay can be conducted with the antibody. If the test compound disrupts the protein complex, then the amount of immunoprecipitated protein complex in this assay will be significantly less than that in a control assay in which the same protein complex is not contacted with the test compound. Similarly, two proteins the interaction between which is to be enhanced may be incubated together with a test compound. Thereafter, a protein complex may be detected by the selectively immunoreactive antibody. The amount of protein complex may be compared to that formed in the absence of the test compound. Various other detection methods may be suitable in the dissociation assay, as will be apparent to skilled artisan apprised of the present disclosure.

5.3. In Vivo Screening Assays

Test compounds can also be screened in any in vivo assays to select modulators of the protein complexes or interacting protein members thereof in accordance with the present invention. For example, any in vivo assays known in the art to be useful in identifying compounds capable of strengthening or interfering with the stability of the protein complexes of the present invention may be used.

5.3.1. Two-Hybrid Assays

In a preferred embodiment, one of the yeast two hybrid systems or their analogous or derivative forms is used.

Examples of suitable two-hybrid systems known in the art include, but are not limited to, those disclosed in U.S. Pat. Nos. 5,283,173; 5,525,490; 5,585,245; 5,637,463; 5,695,941; 5,733,726; 5,776,689; 5,885,779, 5,905,025; 6,037,136; 6.057, 101; 6,114,111; and Bartel and Fields, eds., *The Yeast Two-Hybrid system*, Oxford University Press, New York, N.Y., 1997, all of which are incorporated herein by reference.

Typically, in a classic transcription-based two-hybrid assay, two chimeric genes are prepared encoding two fusion proteins: one contains a transcription activation domain fused to an interacting protein member of a protein complex of the present invention or an interaction domain or fragment of the interacting protein member, while the other fusion protein includes a DNA binding domain fused to another interacting protein member of the protein complex or a fragment or interaction domain thereof. For the purpose of convenience, the two interacting protein members, fragments or interaction domains thereof are referred to as "bait fusion protein" and "prey fusion protein," respectively. The chimeric genes encoding the fusion proteins are termed "bait chimeric gene" and "prey chimeric gene," respectively. Typically, a "bait vector" and a "prey vector" are provided for the expression of a bait chimeric gene and a prey chimeric gene, respectively.

5.3.1.1. Vectors

Many types of vectors can be used in a transcription-based two-hybrid assay. Methods for the construction of bait vectors and prey vectors should be apparent to skilled artisans in the art apprised of the present disclosure. See generally, *Current Protocols in Molecular Biology*, Vol. 2, Ed. Ausubel, et at., Greene Publish. Assoc. & Wiley Interscience, Ch. 13, 1988; Glover, *DNA Cloning, Vol. II, IRL Press, Wash., D.C., Ch.* 3, 1986; Bitter, et al., in *Methods in Enzymology* 153:516–544 (1987); *The Molecular Biology of the Yeast Saccharomyces*, Eds. Strathern et al., Cold Spring Harbor Press, Vols. I and II, 1982; and Rothstein in *DNA Cloning: A Practical Approach*, Vol. 11, Ed. D M Glover, IRL Press, Wash., D.C., 1986.

Generally, the bait and prey vectors include an expression cassette having a promoter operably linked to a chimeric gene for the transcription of the chimeric gene. The vectors may also include an origin of DNA replication for the replication of the vectors in host cells and a replication origin for the amplification of the vectors in, e.g., *E. coli*, and selection marker(s) for selecting and maintaining only those host cells harboring the vectors. Additionally, the expression cassette preferably also contains inducible elements, which function to control the expression of a chimeric gene. Making the expression of the chimeric genes inducible and controllable is especially important in the event that the fusion proteins or components thereof are toxic to the host cells. Other regulatory sequences such as transcriptional enhancer sequences and translation regulation sequences (e.g., Shine-Dalgarno sequence) can also be included in the expression cassette. Termination sequences such as the bovine growth hormone, SV40, lacZ and AcMNPV polyhedral polyadenylation signals may also be operably linked to a chimeric gene in the expression cassette. An epitope tag coding sequence for detection and/or purification of the fusion proteins can also be operably linked to the chimeric gene in the expression cassette. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. The vectors can be introduced into the host cells by any techniques known in the art, e.g., by direct DNA transformation, microinjection, electroporation, viral infection, lipofection, gene gun, and the like. The bait and prey vectors can be maintained in host cells in an extrachromosomal state, i.e., as self-replicating plasmids or viruses. Alternatively, one or both vectors can be integrated into chromosomes of the host cells by conventional techniques such as selection of stable cell lines or site-specific recombination.

The in vivo assays of the present invention can be conducted in many different host cells, including but not limited to bacteria, yeast cells, plant cells, insect cells, and mammalian cells. A skilled artisan will recognize that the designs of the vectors can vary with the host cells used. In one embodiment, the assay is conducted in prokaryotic cells such as *Escherichia coli, Salmonella, Klebsiella, Pseudomonas, Caulobacter*, and *Rhizobium*. Suitable origins of replication for the expression vectors useful in this embodiment of the present invention include, e.g., the ColE1, pSC101, and M13 origins of replication. Examples of suitable promoters include, for example, the T7 promoter, the lacZ promoter, and the like. In addition, inducible promoters are also useful in modulating the expression of the chimeric genes. For example, the lac operon from bacteriophage lambda plac5 is well known in the art and is inducible by the addition of IPTG to the growth medium. Other known inducible promoters useful in a bacteria expression system include pL of bacteriophage λ, the trp promoter, and hybrid promoters such as the tac promoter, and the like.

In addition, selection marker sequences for selecting and maintaining only those prokaryotic cells expressing the desirable fusion proteins should also be incorporated into the expression vectors. Numerous selection markers including auxotrophic markers and antibiotic resistance markers are known in the art and can all be useful for purposes of this invention. For example, the bla gene, which confers ampicillin resistance, is the most commonly used selection marker in prokaryotic expression vectors. Other suitable markers include genes that confer neomycin, kanamycin, or hygromycin resistance to the host cells. In fact, many vectors are commercially available from vendors such as Invitrogen Corp. of Carlsbad, Calif., Clontech Corp. of Palo Alto, Calif., and Stratagene Corp. of La Jolla, Calif., and Promega Corp. of Madison, Wis. These commercially available vectors, e.g., pBR322, pSPORT, pBluescriptIISK, pcDNAI, and pcDNAII all have a multiple cloning site into which the chimeric genes of the present invention can be conveniently inserted using conventional recombinant techniques. The constructed expression vectors can be introduced into host cells by various transformation or transfection techniques generally known in the art.

In another embodiment, mammalian cells are used as host cells for the expression of the fusion proteins and detection of protein—protein interactions. For this purpose, virtually any mammalian cells can be used including normal tissue cells, stable cell lines, and transformed tumor cells. Conveniently, mammalian cell lines such as CHO cells, Jurkat T cells, NIH 3T3 cells, HEK-293 cells, CV-1 cells, COS-1 cells, HeLa cells, VERO cells, MDCK cells, W138 cells, and the like are used. Mammalian expression vectors are well known in the art and many are commercially available. Examples of suitable promoters for the transcription of the chimeric genes in mammalian cells include viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Inducible promoters can also be used. Suitable inducible promoters include, for example, the tetracycline responsive element (TRE) (See Gossen et al., *Proc. Natl. Acad. Sci. USA*, 89:5547–5551 (1992)), metallothionein HA promoter, ecdysone-responsive promoter, and heat shock promoters. Suitable origins of replication for the replication and maintenance of the expression vectors in mammalian cells include, e.g., the Epstein Barr origin of replication in the presence of the Epstein Barr nuclear antigen (see Sugden et al., *Mole. Cell. Biol.*, 5:410–413 (1985)) and the SV40 origin of replication in the presence of the SV40 T antigen (which is present in COS-1 and COS-7 cells) (see Margolskee et al., *Mole. Cell. Biol.*, 8:2837 (1988)). Suitable selection markers include, but are not limited to, genes conferring resistance to neomycin, hygromycin, zeocin, and the like. Many commercially available mammalian expression vectors may be useful for the present invention, including, e.g., pCEP4, pcDNAI, pIND, pSecTag2, pVAX1, pcDNA3.1, and pBI-EGFP, and pDisplay. The vectors can be introduced into mammalian cells using any known techniques such as calcium phosphate precipitation, lipofection, electroporation, and the like. The bait vector and prey vector can be co-transformed into the same cell or, alternatively, introduced into two different cells which are subsequently fused together by cell fusion or other suitable techniques.

Viral expression vectors, which permit introduction of recombinant genes into cells by viral infection, can also be used for the expression of the fusion proteins. Viral expression vectors generally known in the art include viral vectors based on adenovirus, bovine papilloma virus, murine stem cell virus (MSCV), MFG virus, and retrovirus. See Sarver, et al., *Mol. Cell. Biol.*, 1: 486 (1981); Logan & Shenk, *Proc. Natl. Acad. Sci. USA*, 81:3655–3659 (1984); Mackett, et al., *Proc. Natl. Acad. Sci. USA*, 79:7415–7419 (1982); Mackett, et al., *J. Virol.*, 49:857–864 (1984); Panicali, et al., *Proc. Natl. Acad. Sci. USA*, 79:4927–4931 (1982); Cone & Mulligan, *Proc. Natl. Acad. Sci. USA*, 81:6349–6353 (1984); Mann et al., *Cell*, 33:153–159 (1993); Pear et al., *Proc. Natl. Acad. Sci. USA*, 90:8392–8396 (1993); Kitamura et al., *Proc. Natl. Acad. Sci, USA*, 92:9146–9150 (1995); Kinsella et al., *Human Gene Therapy*, 7:1405–1413 (1996); Hofmann et al., *Proc. Natl. Acad. Sci. USA*, 93:5185–5190 (1996); Choate et al., *Human Gene Therapy*, 7:2247 (1996); WO 94/19478; Hawley et al., *Gene Therapy*, 1:136 (1994) and Rivere et al., *Genetics*, 92:6733 (1995), all of which are incorporated by reference.

Generally, to construct a viral vector, a chimeric gene according to the present invention can be operably linked to a suitable promoter. The promoter-chimeric gene construct is then inserted into a non-essential region of the viral vector, typically a modified viral genome. This results in a viable recombinant virus capable of expressing the fusion protein encoded by the chimeric gene in infected host cells. Once in the host cell, the recombinant virus typically is integrated into the genome of the host cell. However, recombinant bovine papilloma viruses typically replicate and remain as extrachromosomal elements.

In another embodiment, the detection assays of the present invention are conducted in plant cell systems. Methods for expressing exogenous proteins in plant cells are well known in the art. See generally, Weissbach & Weissbach. *Methods for Plant Molecular Biology*, Academic Press, NY, 1988; Grierson & Corey, *Plant Molecular Biology*, 2d Ed., Blackie, London, 1988. Recombinant virus expression vectors based on, e.g., cauliflower mosaic virus (CaMV) or tobacco mosaic virus (TMV) can all be used. Alternatively, recombinant plasmid expression vectors such as Ti plasmid vectors and Ri plasmid vectors are also useful. The chimeric genes encoding the fusion proteins of the present invention can be conveniently cloned into the expression vectors and placed under control of a viral promoter such as the 35S RNA and 19S RNA promoters of CaMV or the coat protein promoter of TMV, or of a plant promoter, e.g., the promoter of the small subunit of RUBISCO and heat shock promoters (e.g., soybean hsp 17.5-E or hsp 17.3-B promoters).

In addition, the in vivo assay of the present invention can also be conducted in insect cells, e.g., *Spodoptera frugiperda* cells, using a baculovirus expression system. Expression vectors and host cells useful in this system are well known in the art and are generally available from various commercial vendors. For example, the chimeric genes of the present invention can be conveniently cloned into a non-essential region (e.g., the polyhedrin gene) of an *Autographa californica* nuclear polyhedrosis virus (AcNPV) vector and placed under control of an AcNPV promoter (e.g., the polyhedrin promoter). The non-occluded recombinant viruses thus generated can be used to infect host cells such as *Spodoptera frugiperda* cells in which the chimeric genes are expressed. See U.S. Pat. No. 4,215,051.

In a preferred embodiment of the present invention, the fusion proteins are expressed in a yeast expression system using yeasts such as *Saccharomyces cerevisiae*, *Hansenula polymorpha*, *Pichia pastoris*, and *Schizosaccharomyces pombe* as host cells. The expression of recombinant proteins in yeasts is a well-developed field, and the techniques useful in this respect are disclosed in detail in *The Molecular Biology of the Yeast Saccharomyces*, Eds. Strathern et al., Vols. I and II, Cold Spring Harbor Press, 1982; Ausubel et al., *Current Protocols in Molecular Biology*, New York, Wiley, 1994; and Guthrie and Fink, *Guide to Yeast Genetics and Molecular Biology*, in *Methods in Enzymology*, Vol. 194, 1991, all of which are incorporated herein by reference. Sudbery, *Curr. Opin. Biotech.*, 7:517–524 (1996) reviews the success in the art in expressing recombinant proteins in various yeast species; the entire content and references cited therein are incorporated herein by reference. In addition, Bartel and Fields, eds., *The Yeast Two-Hybrid System*, Oxford University Press, New York, N.Y., 1997 contains extensive discussions of recombinant expression of fusion proteins in yeasts in the context of various yeast two-hybrid systems, and cites numerous relevant references. These and other methods known in the art can all be used for purposes of the present invention. The application of such methods to the present invention should be apparent to a skilled artisan apprised of the present disclosure.

Generally, each of the two chimeric genes is included in a separate expression vector (bait vector and prey vector). Both vectors can be co-transformed into a single yeast host cell. As will be apparent to a skilled artisan, it is also possible to express both chimeric genes from a single vector. In a preferred embodiment, the bait vector and prey vector are introduced into two haploid yeast cells of opposite mating types, e.g., a-type and α-type, respectively. The two haploid cells can be mated at a desired time to form a diploid cell expressing both chimeric genes.

Generally, the bait and prey vectors for recombinant expression in yeast include a yeast replication origin such as the 2 µl origin or the ARSH4 sequence for the replication and maintenance of the vectors in yeast cells. Preferably, the vectors also have a bacteria origin of replication (e.g., ColE1) and a bacteria selection marker (e.g., amp$^R$ marker, i.e., bla gene). Optionally, the CEN6 centromeric sequence is included to control the replication of the vectors in yeast cells. Any constitutive or inducible promoters capable of driving gene transcription in yeast cells may be employed to control the expression of the chimeric genes. Such promoters are operably linked to the chimeric genes. Examples of suitable constitutive promoters include but are not limited to the yeast ADH1, PGK1 TEF2, GPD1, HIS3, and CYC1 promoters. Example of suitable inducible promoters include but are not limited to the yeast GAL1 (inducible by galactose). CUP1 (inducible by $Cu^{++}$), and FUS1 (inducible by pheromone) promoters; the AOX/MOX promoter from H. polymorpha and P. Pastoris (repressed by glucose or ethanol and induced by methanol); chimeric promoters such as those that contain LexA operators (inducible by LexA-containing transcription factors); and the like. Inducible promoters are preferred when the fusion proteins encoded by the chimeric genes are toxic to the host cells. If it is, desirable, certain transcription repressing sequences such as the upstream repressing sequence (URS) from SPO13 promoter can be operably linked to the promoter sequence, e.g., to the 5' end of the promoter region. Such upstream repressing sequences function to fine-tune the expression level of the chimeric genes.

Preferably, a transcriptional termination signal is operably linked to the chimeric genes in the vectors. Generally, transcriptional termination signal sequences derived from, e.g., the CYC1 and ADH1 genes can be used.

Additionally, it is preferred that the bait vector and prey vector contain one or more selectable markers for the selection and maintenance of only those yeast cells that harbor one or both chimeric genes. Any selectable markers known in the art can be used for purposes of this invention so long as yeast cells expressing the chimeric gene(s) can be positively identified or negatively selected. Examples of markers that can be positively identified are those based on color assays, including the lacZ gene (which encodes β-galactosidase), the firefly luciferase gene, secreted alkaline phosphatase, horseradish peroxidase, the blue fluorescent protein (BFP), and the green fluorescent protein (GFP) gene (see Cubitt et al., Trends Biochem. Sci., 20:448–455 (1995)). Other markers allowing detection by fluorescence, chemiluminescence, UV absorption, infrared radiation, and the like can also be used. Among the markers that can be selected are auxotrophic markers including, but not limited to, URA3, HIS3, TRP1, LEU2, LYS2. ADE2, and the like. Typically, for purposes of auxotrophic selection, the yeast host cells transformed with bait vector and/or prey vector are cultured in a medium lacking a particular nutrient. Other selectable markers are not based on auxotrophies, but rather on resistance or sensitivity to an antibiotic or other xenobiotic. Examples of such markers include but are not limited to chloramphenicol acetyl transferase (CAT) gene, which confers resistance to chloramphenicol; CAN1 gene, which encodes an arginine permease and thereby renders cells sensitive to canavanine (see Sikorski et al., Meth. Enzymol., 194:302–318 (1991)); the bacterial kanamycin resistance gene (kan$^R$), which renders eukaryotic cells resistant to the aminoglycoside G418 (see Wach et al., Yeast, 10: 1793–1808 (1994)); and CYH2 gene, which confers sensitivity to cycloheximide (see Sikorski et al., Meth. Enzymol., 194:302–318 (1991)). In addition, the CUP1 gene, which encodes metallothionein and thereby confers resistance to copper, is also a suitable selection marker. Each of the above selection markers may be used alone or in combination. One or more selection markers can be included in a particular bait or prey vector. The bait vector and prey vector may have the same or different selection markers. In addition, the selection pressure can be placed on the transformed host cells either before or after mating the haploid yeast cells.

As will be apparent, the selection markers used should complement the host strains in which the bait and/or prey vectors are expressed. In other words, when a gene is used as a selection marker gene, a yeast strain lacking the selection marker gene (or having mutation in the corresponding gene) should be used as host cells. Numerous yeast strains or derivative strains corresponding to various selection markers are known in the art. Many of them have been developed specifically for certain yeast two-hybrid systems. The application and optional modification of such strains with respect to the present invention should be apparent to a skilled artisan apprised of the present disclosure. Methods for genetically manipulating yeast strains using genetic crossing or recombinant mutagenesis are well known in the art. See e.g., Rothstein, Meth. Enzymol., 101:202–211 (1983). By way of example, the following yeast strains are well known in the art, and can be used in the present invention upon necessary modifications and adjustment:

L40 strain which has the genotype MATα his3Δ200 trp1-901 leu2-3,112 ade2 LYS2::(lexAop)4-HIS3 URA3:: (lexAop)8-lacZ;

EGY48 strain which has the genotype MATα trp1 his3 ura3 6ops-LEU2; and

MaV103 strain which has the genotype MATα ura3-52 leu2-3,112 trp1-901 his3Δ200 ade2-101 gal4Δ gal80Δ SPAL10::URA3 GAL1::HIS3::lys2 (see Kumar et al., J. Biol. Chem. 272:13548–13554 (1997); Vidal et al., Proc. Natl. Acad. Sci. USA, 93:10315–10320 (1996)). Such strains are generally available in the research community, and can also be obtained by simple yeast genetic manipulation. See, e.g., The Yeast Two-Hybrid System, Bartel and Fields, eds., pages 173–182, Oxford University Press, New York, N.Y., 1997.

In addition, the following yeast strains are commercially available:

Y190 strain which is available from Clontech, Palo Alto, Calif. and has the genotype MATα gal4 gal80 his3Δ200 trp1-901 ade2-101 ura3-52 leu2-3, 112 URA3::GAL1-lacZ LYS2::GAL1-HIS3 cyh$^r$; and YRG-2 Strain which is available from Stratagene, La Jolla, Calif. and has the genotype MATα ura3-52 his3-200 ade2-101 lys2-801 Trp1-901 leu2-3, 112 gal4-542 gal80-538 LYS2::GAL1-HIS3 URA3::GAL1/CYC1-lacZ.

In fact, different versions of vectors and host strains specially designed for yeast two-hybrid system analysis are available in kits from commercial vendors such as Clontech, Palo Alto, Calif. and Stratagene, La Jolla, Calif., all of which can be modified for use in the present invention.

5.3.1.2. Reporters

Generally, in a transcription-based two-hybrid assay, the interaction between a bait fusion protein and a prey fusion protein brings the DNA-binding domain and the transcription-activation domain into proximity forming a functional transcriptional factor that acts on a specific promoter to drive the expression of a reporter protein. The transcription activation domain and the DNA-binding domain may be selected from various known transcriptional activators, e.g., GAL4, GCN4, ARD1, the human estrogen receptor, *E. coli* LexA protein, herpes simplex virus VP16 (Triezenberg et al., *Genes Dev.* 2:718–729 (1988)), the *E. coli* B42 protein (acid blob, see Gyuris et al., *Cell*, 75:791–803 (1993)), NF-kB p65, and the like. The reporter gene and the promoter driving its transcription typically are incorporated into a separate reporter vector. Alternatively, the host cells are engineered to contain such a promoter-reporter gene sequence in their chromosomes. Thus, the interaction or lack of interaction between two interacting protein members of a protein complex can be determined by detecting or measuring changes in the reporter in the assay system. Although the reporters and selection markers can be of similar types and used in a similar manner in the present invention, the reporters and selection markers should be carefully selected in a particular detection assay such that they are distinguishable from each other and do not interfere with each other's function.

Many different types reporters are useful in the screening assays. For example, a reporter protein may be a fusion protein having an epitope tag fused to a protein. Commonly used and commercially available epitope tags include sequences derived from, e.g., influenza virus hemagglutinin (HA), Simian Virus 5 (V5), polyhistidine (6xHis), c-myc, lacZ, GST, and the like. Antibodies specific to these epitope tags are generally commercially available. Thus, the expressed reporter can be detected using an epitope-specific antibody in an immunoassay.

In another embodiment, the reporter is selected such that it can be detected by a color-based assay. Examples of such reporters include, e.g., the lacZ protein (β-galactosidase), the green fluorescent protein (GFP), which can be detected by fluorescence assay and sorted by flow-activated cell sorting (FACS) (See Cubitt et al., *Trends Biochem. Sci.,* 20:448–455 (1995)), secreted alkaline phosphatase, horseradish peroxidase, the blue fluorescent protein (BFP), and luciferase photoproteins such as aequorin, obelin, mnemiopsin, and berovin (See U.S. Pat. No. 6,087,476, which is incorporated herein by reference).

Alternatively, an auxotrophic factor is used as a reporter in a host strain deficient in the auxotrophic factor. Thus, suitable auxotrophic reporter genes include, but are not limited to, URA3, HIS3, TRP1, LEU2, LYS2, ADE2, and the like. For example, yeast cells containing a mutant URA3 gene can be used as host cells (Ura$^-$ phenotype). Such cells lack URA3-encoded functional orotidine-5'-phosphate decarboxylase, an enzyme required by yeast cells for the biosynthesis of uracil. As a result, the cells are unable to grow on a medium lacking uracil. However, wild-type orotidine-5'-phosphate decarboxylase catalyzes the conversion of a non-toxic compound 5-fluoroorotic acid (5-FOA) to a toxic product, 5-fluorouracil. Thus, yeast cells containing a wild-type URA3 gene are sensitive to 5-FOA and cannot grow on a medium containing 5-FOA. Therefore, when the interaction between the interacting protein members in the fusion proteins results in the expression of active orotidine-5'-phosphate decarboxylase, the URa (Foa$^R$) yeast cells will be able to grow on a uracil deficient medium (SC-Ura plates). However, such cells will not survive on a medium containing 5-FOA. Thus, protein—protein interactions can be detected based on cell growth.

Additionally, antibiotic resistance reporters can also be employed in a similar manner. In this respect, host cells sensitive to a particular antibiotic are used. Antibiotics resistance reporters include, for example, the chloramphenicol acetyl transferase (CAT) gene and the kan$^R$ gene, which confer resistance to G418 in eukaryotes, and kanamycin in prokaryotes, respectively.

5.3.1.3. Screening Assays for Interaction Antagonists

The screening assays of the present invention are useful in identifying compounds capable of interfering with or disrupting or dissociating protein—protein interactions between MAP17 or a mutant form thereof and SCAMP2 or a mutant form thereof. For example, MAP17 and SCAMP2 are believed to play a role in regulating cell proliferation and membrane trafficking, and thus are involved in kidney, colon, breast, and lung cancers. It may be possible to ameliorate or alleviate the diseases or disorders in a patient by interfering with or dissociating normal interactions between MAP17 and SCAMP2. Alternatively, if the disease or disorder is associated with increased expression of MAP17 and/or SCAMP2 in accordance with the present invention, then the disease may be treated or prevented by weakening or dissociating the interaction between MAP17 and SCAMP2 in patients. In addition, if a disease or disorder is associated with a mutant form of MAP17 and/or a mutant form of SCAMP2 that exhibit strengthened protein—protein interaction therebetween, then the disease or disorder may be treated with a compound that weakens or interferes with the interaction between the particular forms of MAP17 and SCAMP2.

In a screening assay for an interaction antagonist, MAP17 (or homologues, derivatives, or fragments thereof) or a mutant form of MAP17 (or homologues, derivatives, or fragments thereof), and SCAMP2, (or homologues, derivatives, or fragments thereof) or a mutant form of SCAMP2 (or homologues, derivatives, or fragments thereof), are used as test proteins expressed in the form of fusion proteins as described above for purposes of a two-hybrid assay. The fusion proteins are expressed in a host cell and allowed to interact with each other in the presence of one or more test compounds.

In a preferred embodiment, a counterselectable marker is used as a reporter such that a detectable signal (e.g., appearance of color or fluorescence, or cell survival) is present only when the test compound is capable of interfering with the interaction between the two test proteins. In this respect, the reporters used in various "reverse two-hybrid systems" known in the art may be employed. Reverse two-hybrid systems are disclosed in, e.g., U.S. Pat. Nos. 5,525,490; 5,733,726; 5,885,779; Vidal et al., *Proc. Natl. Acad. Sci. USA*, 93:10315–10320 (1996); and Vidal et al., *Proc. Natl. Acad. Sci. USA*, 93:10321–10326 (1996), all of which are incorporated herein by reference.

Examples of suitable counterselectable reporters useful in a yeast system include the URA3 gene (encoding orotidine-5'-decarboxylase, which converts 5-fluroorotic acid (5-FOA) to the toxic metabolite 5-fluorouracil), the CAN1 gene (encoding arginine permease, which transports toxic arginine analog canavanine into yeast cells), the GAL1 gene (encoding galactokinase, which catalyzes the conversion of 2-deoxygalactose to toxic 2-deoxygalactose-1-phosphate), the LYS2 gene (encoding α-aminoadipate reductase, which renders yeast cells unable to grow on a medium containing α-aminoadipate as the sole nitrogen source), the MET15 gene (encoding O-acetylhomoserine sulfhydrylase, which confers on yeast cells sensitivity to methyl mercury), and the CYH2 gene (encoding L29 ribosomal protein, which confers sensitivity to cycloheximide). In addition, any known cytotoxic agents including cytotoxic proteins such as the diphtheria toxin (DTA) catalytic domain can also be used as counterselectable reporters. See U.S. Pat. No. 5,733,726. DTA causes the ADP-ribosylation of elongation factor-2 and thus inhibits protein synthesis and causes cell death. Other examples of cytotoxic agents include ricin, Shiga toxin, and exotoxin A of *Pseudormonas aeruginosa*.

For example, when the URA3 gene is used as a counterselectable reporter gene, yeast cells containing a mutant URA3 gene can be used as host cells (Ura Foa$^R$ phenotype) for the in vivo assay. Such cells lack URA3-encoded functional orotidine-5'-phosphate decarboxylase, an enzyme required for the biosynthesis of uracil. As a result, the cells are unable to grow on media lacking uracil. However, because of the absence of a wild-type orotidine-5'-phosphate decarboxylase, the yeast cells cannot convert non-toxic 5-fluoroorotic acid (5-FOA) to a toxic product, 5-fluorouracil. Thus, such yeast cells are resistant to 5-FOA and can grow on a medium containing 5-FOA. Therefore, for example, to screen for a compound capable of disrupting interactions between MAP17 and SCAMP2, MAP17 (or a homologue, derivative, or fragment thereof) can be expressed as a fusion protein with a DNA-binding domain of a suitable transcription activator while SCAMP2 (or a homologue, derivative, or fragment thereof) is expressed as a fusion protein with a transcription activation domain of a suitable transcription activator. In the host strain, the reporter URA3 gene may be operably linked to a promoter specifically responsive to the association of the transcription activation domain and the DNA-binding domain. After the fusion proteins are expressed in the Ura Foa$^R$ yeast cells, an in vivo screening assay can be conducted in the presence of a test compound with the yeast cells being cultured on a medium containing uracil and 5-FOA. If the test compound does not disrupt the interaction between MAP17 and SCAMP2, active URA3 gene product, i.e., orotidine-5'-decarboxylase, which converts 5-FOA to toxic 5-fluorouracil, is expressed. As a result, the yeast cells cannot grow. On the other hand, when the test compound disrupts the interaction between MAP17 and SCAMP2, no active orotidine-5'-decarboxylase is produced in the host yeast cells. Consequently, the yeast cells will survive and grow on the 5-FOA-containing medium. Therefore, compounds capable of interfering with or dissociating the interaction between MAP17 and SCAMP2 can thus be identified based on colony formation.

As will be apparent, the screening assay of the present invention can be applied in a format appropriate for large-scale screening. For example, combinatorial technologies can be employed to construct combinatorial libraries of small organic molecules or small peptides. See generally, e.g., Kenan et al., *Trends Biochem. Sc.,* 19:57–64 (1994); Gallop et al., *J. Med. Chem.,* 37:1233–1251 (1994); Gordon et al., *J. Med. Chem.,* 37:1385–1401 (1994); Ecker et al., *Biotechnology,* 13:351–360 (1995). Such combinatorial libraries of compounds can be applied to the screening assay of the present invention to isolate specific modulators of particular protein—protein interactions. In the case of random peptide libraries, the random peptides can be co-expressed with the fusion proteins of the present invention in host cells and assayed in vivo. See e.g., Yang et al., *Nucl. Acids Res.,* 23: 1152–1156 (1995). Alternatively, they can be added to the culture medium for uptake by the host cells.

Conveniently, yeast mating is used in an in vivo screening assay. For example, haploid cells of a-mating type expressing one fusion protein as described above are mated with haploid cells of a-mating type expressing the other fusion protein. Upon mating, the diploid cells are spread on a suitable medium to form a lawn. Drops of test compounds can be deposited onto different areas of the lawn. After culturing the lawn for an appropriate period of time, drops containing a compound capable of modulating the interaction between the particular test proteins in the fusion proteins can be identified by stimulation or inhibition of growth in the vicinity of the drops.

The screening assays of the present invention for identifying compounds capable of modulating protein—protein interactions can also be fine-tuned by various techniques to adjust the thresholds or sensitivity of the positive and negative selections. Mutations can be introduced into the reporter proteins to adjust their activities. The uptake of test compounds by the host cells can also be adjusted. For example, yeast high uptake mutants such as the erg6 mutant strains can facilitate yeast uptake of the test compounds. See Gaber et al., *Mol. Cell. Biol.,* 9:3447–3456 (1989). Likewise, the uptake of the selection compounds such as 5-FOA, 2-deoxygalactose, cycloheximide, α-aminoadipate, and the like can also be fine-tuned.

5.3.1.4. Screening Assays for Interaction Agonists

The screening assays of the present invention can also be used in identifying compounds that trigger or initiate, enhance or stabilize protein—protein interactions between MAP17 or a mutant form thereof and SCAMP2 or a mutant form thereof. For example, if a disease or disorder is associated with decreased expression of MAP17 and/or SCAMP2, then the disease or disorder may be treated or prevented by strengthening or stabilizing the interaction between MAP17 and SCAMP2 in a patient. Alternatively, if a disease or disorder is associated with a mutant form of MAP17 and/or a mutant form of SCAMP2 that exhibit weakened or abolished protein—protein interaction therebetween, then the disease or disorder may be treated with a compound that initiates or stabilizes the interaction between the particular forms of MAP17 and/or SCAMP2.

Thus, a screening assay can be performed in the same manner as described above, except that a positively selectable marker is used. For example, MAP17 (or homologues, derivatives, or fragments thereof) or a mutant form of MAP17 (or homologues, derivatives, or fragments thereof), and SCAMP2, (or homologues, derivatives, or fragments thereof) or a mutant form of SCAMP2 (or homologues, derivatives, or fragments thereof), are used as test proteins expressed in the form of fusion proteins as described above for purposes of a two-hybrid assay. The fusion proteins are expressed in host cells and are allowed to interact with each other in the presence of one or more test compounds.

A gene encoding a positively selectable marker such as the lacZ protein may be used as a reporter gene such that when a test compound enables or enhances the interaction between MAP17 (or homologues, derivatives, or fragments thereof), or a mutant form of MAP17 (or homologues, derivatives, or fragments thereof), and SCAMP2 (or homologues, derivatives, or fragments thereof), or a mutant form of SCAMP2 (or homologues, derivatives, or fragments thereof), the lacZ protein, i.e., β-galatosidase, is expressed. As a result, the compound may be identified based on the appearance of a blue color when the host cells are cultured in a medium containing X-Gal.

Generally, a control assay is performed in which the above screening assay is conducted in the absence of the test compound. The result is then compared with that obtained in the presence of the test compound.

5.4. Optimization of the Identified Compounds

Once the test compounds capable of modulating the interaction between MAP17 and SCAMP2 or modulating MAP17 or SCAMP2 are selected, a data set including data defining the identity or characteristics of the test compounds can be generated. The data set may include information relating to the properties of a selected test compound, e.g., chemical structure, chirality, molecular weight, melting point, etc. Alternatively, the data set may simply include assigned identification numbers understood by the researchers conducting the screening assay and/or researchers receiving the data set as representing specific test compounds. The data or information can be cast in a transmittable form that can be communicated or transmitted to other researchers, particularly researchers in a different country. Such a transmittable form can vary and can be tangible or intangible. For example, the data set defining one or more selected test compounds can be embodied in texts, tables, diagrams, molecular structures, photographs, charts, images or any other visual forms. The data or information can be recorded on a tangible media such as paper or embodied in computer-readable forms (e.g., electronic, electromagnetic, optical or other signals). The data in a computer-readable form can be stored in a computer usable storage medium (e.g., floppy disks, magnetic tapes, optical disks, and the like) or transmitted directly through a communication infrastructure. In particular, the data embodied in electronic signals can be transmitted in the form of email or posted on a website on the Internet or Intranet. In addition, the information or data on a selected test compound can also be recorded in an audio form and transmitted through any suitable media, e.g., analog or digital cable lines, fiber optic cables, etc., via telephone, facsimile, wireless mobile phone. Internet phone and the like.

Thus, the information and data on a test compound selected in a screening assay described above or by virtual screening as discussed below can be produced anywhere in the world and transmitted to a different location. For example, when a screening assay is conducted offshore, the information and data on a selected test compound can be generated and cast in a transmittable form as described above. The data and information in a transmittable form thus can be imported into the U.S. or transmitted to any other countries, where the data and information may be used in further testing the selected test compound and/or in modifying and optimizing the selected test compound to develop lead compounds for testing in clinical trials.

Compounds can also be selected based on structural models of the target protein or protein complex and/or test compounds. In addition, once an effective compound is identified, structural analogs or mimetics thereof can be produced based on rational drug design with the aim of improving drug efficacy and stability, and reducing side effects. Methods known in the art for rational drug design can be used in the present invention. See, e.g., Hodgson et al., *Bio/Technology,* 9:19–21 (1991); U.S. Pat. Nos. 5,800, 998 and 5,891,628, all of which are incorporated herein by reference. An example of rational drug design is the development of HIV protease inhibitors. See Erickson et al., *Science,* 249:527–533 (1990).

In this respect, structural information on the target protein or protein complex is obtained. Preferably, atomic coordinates defining a three-dimensional structure of the target protein or protein complex can be obtained. For example, each of the interacting pair can be expressed and purified. The purified interacting protein pairs are then allowed to interact with each other in vitro under appropriate conditions. Optionally, the interacting protein complex can be stabilized by crosslinking or other techniques. The interacting complex can be studied using various biophysical techniques including, e.g., X-ray crystallography, NMR, computer modeling, mass spectrometry, and the like. Likewise, structural information can also be obtained from protein complexes formed by interacting proteins and a compound that initiates or stabilizes the interaction of the proteins. Methods for obtaining such atomic coordinates by X-ray crystallography, NMR, and the like are known in the art and the application thereof to the target protein or protein complex of the present invention should be apparent to skilled persons in the art of structural biology. See Smyth and Martin, *Mol. Pathol.,* 53:8–14 (2000); Oakley and Wilce, *Clin. Exp. Pharmacol. Physiol.,* 27(3):145–151 (2000); Ferentz and Wagner, *Q. Rev. Biophys.,* 33:29–65 (2000); Hicks, *Curr. Med. Chem.,* 8(6):627–650 (2001); and Roberts, *Curr. Opin. Biotechnol.,* 10:42–47 (1999).

In addition, understanding of the interaction between the proteins of interest in the presence or absence of a modulator compound can also be derived from mutagenesis analysis using yeast two-hybrid system or other methods for detection protein—protein interaction. In this respect, various mutations can be introduced into the interacting proteins and the effect of the mutations on protein—protein interaction examined by a suitable method such as the yeast two-hybrid system.

Various mutations including amino acid substitutions, deletions and insertions can be introduced into a protein sequence using conventional recombinant DNA technologies. Generally, it is particularly desirable to decipher the protein binding sites. Thus, it is important that the mutations introduced only affect protein—protein interaction and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein—protein interactions. Alternatively, the "alanine scanning mutagenesis" technique is used. See Wells, et al., *Methods Enzymol.,* 202:301–306 (1991); Bass et al., *Proc. Natl. Acad. Sci. USA,* 88:4498–4502 (1991); Bennet et al., *J. Biol. Chem.,* 266:5191–5201 (1991); Diamond et al., *J. Virol.,* 68:863–876 (1994). Using this technique, charged or hydrophobic amino acid residues of the interacting proteins are replaced by alanine, and the effect on the interaction between the proteins is analyzed using e.g., the yeast two-hybrid system. For example, the entire protein sequence can be scanned in a window of five amino acids. When two or more charged or hydrophobic amino acids appear in a window, the charged or hydrophobic amino acids are changed to alanine using standard recombinant DNA techniques. The thus mutated proteins are used as "test proteins" in the above-described two-hybrid assays to examine the effect of the mutations on protein—protein interaction. Preferably, the mutagenesis analysis is conducted both in the presence and in the absence of an identified modulator compound. In this manner, the domains or residues of the proteins important to protein—protein interaction and/or the interaction between the modulator compound and the interacting proteins can be identified.

Based on the information obtained, structural relationships between the interacting proteins, as well as between the identified modulators and the interacting proteins are elucidated. For example, for the identified modulators (i.e., lead compounds), the three-dimensional structure and chemical moieties critical to their modulating effect on the interacting proteins are revealed. Using this information and various techniques know in the art of molecular modeling (i.e., simulated annealing), medicinal chemists can then design analog compounds that might be more effective modulators of the protein—protein interactions of the present invention. For example, the analog compounds might show more specific or tighter binding to their targets, and thereby might exhibit fewer side effects, or might have more desirable pharmacological characteristics (e.g., greater solubility).

In addition, if the lead compound is a peptide, it can also be analyzed by the alanine scanning technique and/or the two-hybrid assay to determine the domains or residues of the peptide important to its modulating effect on particular protein—protein interactions. The peptide compound can be used as a lead molecule for rational design of small organic molecules or peptide mimetics. See Huber et al., *Curr. Med. Chem.*, 1:13–34 (1994).

The domains, residues or moieties critical to the modulating effect of the identified compound constitute the active region of the compound known as its "pharmacophore." Once the pharmacophore has been elucidated, a structural model can be established by a modeling process that may incorporate data from NMR analysis, X-ray diffraction data, alanine scanning, spectroscopic techniques and the like. Various techniques including computational analysis (e.g., molecular modeling and simulated annealing), similarity mapping and the like can all be used in this modeling process. See e.g., Perry et al., in *OSAR: Quantitative Structure-Activity Relationships in Drug Design* pp. 189–193, Alan R. Liss, Inc., 1989; Rotivinen et al., *Acta Pharmaceutica Fennica*, 97:159–166 (1988); Lewis et al., *Proc. R. Soc. Lond.*, 236:125–140 (1989); McKinaly et al., *Annu. Rev. Pharmacol. Toxiciol.*, 29:111–122 (1989). Commercial molecular modeling systems available from Polygen Corporation, Waltham, Mass., include the CHARMm program, which performs energy minimization and molecular dynamics functions, and the QUANTA program which performs construction, graphic modeling and analysis of molecular structure. Such programs allow interactive construction, modification and visualization of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed. The compounds identified in accordance with the present invention can be incorporated into a pharmaceutical formulation suitable for administration to an individual.

In addition, the structural models or atomic coordinates defining a three-dimensional structure of the target protein or protein complex can also be used in virtual screen to select compounds capable of modulating the target protein or protein complex. Various methods of computer-based virtual screen using atomic coordinates are generally known in the art. For example, U.S. Pat. No. 5,798,247 (which is incorporated herein by reference) discloses a method of identifying a compound (specifically, an interleukin converting enzyme inhibitor) by determining binding interactions between an organic compound and binding sites of a binding cavity within the target protein. The binding sites are defined by atomic coordinates.

The compounds designed or selected based on rational drug design or virtual screen can be tested for their ability to modulate (interfere with or strengthen) the interaction between the interacting partners within the protein complexes of the present invention. In addition, the compounds can also be further tested for their ability to modulate (inhibit or enhance) cellular functions such as regulating cell proliferation and membrane trafficking in cells as well as their effectiveness in treating diseases such as kidney, colon, breast, and lung cancers.

6. Therapeutic Applications

As described above, the interactions between MAP17 and SCAMP2 suggest that these proteins and/or the protein complexes formed by them are involved in common biological processes and disease pathways. The protein complexes mediate the functions of MAP17 and SCAMP2 in biological processes or disease pathways. Thus, one may modulate such biological processes or treat diseases by modulating the functions and activities of MAP17, SCAMP2, and/or protein complexes comprising MAP17 and SCAMP2. As used herein, modulating the functions or activities of MAP17, or SCAMP2, or protein complexes comprising MAP17 and SCAMP2 means altering (enhancing or reducing) the concentrations or activities of the proteins or protein complexes, e.g., increasing the concentrations of MAP17, or SCAMP2 or protein complexes formed by them, enhancing or reducing their biological activities, increasing or decreasing their stability, altering their affinity or specificity to certain other biological molecules, etc. For example, MAP17 and SCAMP2, and the protein complexes of the present invention may be involved in regulating cell proliferation and membrane trafficking. Thus, assays such as those described in Section 4 may be used in determining the effect of an aberration in a particular MAP17-SCAMP2 complex, or an interacting member thereof, on regulating cell proliferation and membrane trafficking. In addition, it is also possible to determine, using the same assay methods, the presence or absence of an association between a MAP17-SCAMP2 complex, or an interacting member thereof, and a physiological disorder or disease such as kidney, colon, breast, and lung cancers or predisposition to a physiological disorder or disease.

Once such associations are established, the diagnostic methods as described in Section 4 can be used in diagnosing the disease or disorder, or a patient's predisposition to it. In addition, various in vitro and in vivo assays may be employed to test the therapeutic or prophylactic efficacies of the various therapeutic approaches described in Sections 6.2 and 6.3 which are aimed at modulating the functions and activities of the MAP17-SCAMP2 complex of the present invention, or an interacting member thereof. Similar assays can also be used to test whether the therapeutic approaches described in Sections 6.2 and 6.3 result in the modulation of regulating cell proliferation and membrane trafficking. The cell model or transgenic animal model described in Section 7 may be employed in the in vitro and in vivo assays.

In accordance with this aspect of the present invention, methods are provided for modulating (promoting or inhibiting) MAP17 or SCAMP2 or a protein complex comprising MAP17 and SCAMP2 in human cells. The human cells can be in in vitro cell or tissue cultures. The methods are also applicable to human cells in a patient.

In one embodiment, the concentration of a protein complex having MAP17 interacting with SCAMP2 is reduced in the cells. Various methods call be employed to reduce the concentration of the protein complex. The protein complex concentration can be reduced by interfering with the interactions between MAP17 and SCAMP2. For example, compounds capable of interfering with interactions between MAP17 and SCAMP2 can be administered to the cells in vitro or in vivo in a patient. Such compounds can be compounds capable of binding MAP17 or SCAMP2. They can also be antibodies immunoreactive with the MAP17 or SCAMP2. Also, the compounds can be small peptides derived from the SCAMP2 protein or mimetics thereof capable of binding MAP17, or small peptides derived from MAP17 protein or mimetics thereof capable of binding SCAMP2.

In another embodiment, the method of modulating the protein complex includes inhibiting the expression of MAP17 protein and/or SCAMP2 protein. The inhibition can be at the transcriptional, translational, or post-translational level. For example, antisense compounds and ribozyme compounds can be administered to human cells in cultures or in human bodies. In addition, RNA interference technologies may also be employed to administer to cells double-stranded RNA or RNA hairpins capable of "knocking down" the expression of MAP17 protein and/or SCAMP2 protein.

In the various embodiments described above, preferably the concentrations or activities of both MAP17 protein and SCAMP2 are reduced or inhibited.

In yet another embodiment, an antibody selectively immunoreactive with a protein complex having MAP17 interacting with SCAMP2 is administered to cells in vitro or in human bodies to inhibit the protein complex activities and/or reduce the concentration of the protein complex in the cells or patient.

6.1. Applicable Diseases

The methods for modulating the functions and activities of MAP17 or SCAMP2, or the functions and activities of protein complexes comprising MAP17 and SCAMP2, may be employed to modulate regulating cell proliferation and membrane trafficking. In addition, the methods may also be used in the treatment or prevention of diseases and disorders such as kidney, colon, breast, and lung cancers.

6.2. Inhibiting Protein Complex or Interacting Protein Members Thereof

In one aspect of the present invention, methods are provided for reducing in cells or tissue in vitro or in patients the concentration and/or activity of a protein complex identified in accordance with the present invention that comprises MAP17 and SCAMP2. In addition, methods are also provided for reducing in cells or tissue in vitro or in patients the concentration and/or activity of MAP17 and/or SCAMP2. By reducing the concentration and/or inhibiting the functional activities of the protein complex, and/or MAP17, and/or SCAMP2, the diseases involving said protein complex or MAP17 or SCAMP2 may be treated or prevented.

6.2.1. Antibody Therapy

In one embodiment, an antibody may be administered to cells or tissue in vitro or to patients. The antibody administered may be immunoreactive with MAP17, SCAMP2, or protein complexes comprising MAP17 and SCAMP2. Suitable antibodies may be monoclonal or polyclonal that fall within any antibody class, e.g., IgG, IgM, IgA, etc. The antibody suitable for this invention may also take a form of various antibody fragments including, but not limited to, Fab and F(ab')$_2$, single-chain fragments (scFv), and the like. In another embodiment, an antibody selectively immunoreactive with the protein complex comprised of MAP17 and SCAMP2, in accordance with the present invention, is administered to cells or tissue in vitro or to patients. In yet another embodiment, an antibody specific to MAP17 or to SCAMP2 is administered to cells or tissue in vitro or to patients. Methods for making the antibodies of the present invention should be apparent to a person of skill in the art, especially in view of the discussions in Section 3 above. The antibodies can be administered in any suitable form and route as described in Section 8 below. Preferably, the antibodies are administered in a pharmaceutical composition together with a pharmaceutically acceptable carrier.

Alternatively, the antibodies may be delivered by a gene-therapy approach. That is, nucleic acids encoding the antibodies, particularly single-chain fragments (scFv), may be introduced into cells or tissue in vitro or into patients such that desirable antibodies may be produced recombinantly in vivo from the nucleic acids. For this purpose, the nucleic acids with appropriate transcriptional and translation regulatory sequences can be directly administered into the patient. Alternatively, the nucleic acids can be incorporated into a suitable vector as described in Sections 2.2 and 5.3.1.1 and delivered into cells or tissue in vitro or into patients along with the vector. The expression vector containing the nucleic acids can be administered directly to a patient. It can also be introduced into cells, preferably cells derived from a patient to be treated, and subsequently delivered into the patient by cell transplantation. See Section 6.3.2 below.

6.2.2. Antisense Therapy

In another embodiment, antisense compounds specific to nucleic acids encoding one or more interacting protein members of a protein complex identified in the present invention are administered to cells or tissue in vitro or to patients to be therapeutically or prophylactically treated. The antisense compounds should specifically inhibit the expression of the one or more interacting protein members. As is known in the art, antisense drugs generally act by hybridizing to a particular target nucleic acid thus blocking gene expression. Methods for designing antisense compounds and using such compounds in treating diseases are well known and well developed in the art. For example, the antisense drug Vitravene® (fomivirsen), a 21-base long oligonucleotide, has been successfully developed and marketed by Isis Pharmaceuticals, Inc. for treating cytomegalovirus (CMV)-induced retinitis.

Any methods for designing and making antisense compounds may be used for purpose of the present invention. See generally, Sanghvi et al., eds., *Antisense Research and Applications*, CRC Press, Boca Raton, 1993. Typically, antisense compounds are oligonucleotides designed based on the nucleotide sequence of the rRNA or gene of one or more of the interacting protein members of a particular protein complex of the present invention. In particular, antisense compounds can be designed to specifically hybridize to a particular region of the gene sequence or mRNA of one or more target proteins, e.g., the interacting proteins of the present invention. In particular, antisense compounds can be designed to specifically hybridize to a particular region of the gene seqence or mRNA of one or more of the interacting proteins, in order to modulate (increase or decrease), replication, transcription, or translation. As used herein, the term "specifically hybridize" or paraphrases thereof means a sufficient degree of complementarity or pairing between an antisense oligo and a target DNA or mRNA such that stable and specific binding occurs therebetween. In particular, 100% complementary or pairing is not required. Specific hybridization takes place when sufficient hybridization occurs between the antisense compound and its intended target nucleic acids in the substantial absence of non-specific binding of the antisense compound to non-target sequences under predetermined conditions, e.g., for purposes of in vivo treatment, under physiological conditions. Preferably, specific hybridization results in the interference with normal expression of the target DNA or mRNA.

For example, an antisense oligonucleotides can be designed to specifically hybridize to target genes, in regions critical for regulation of transcription; to pre-mRNAs, in regions critical for correct splicing of nascent transcripts; and to mature mRNAs, in regions critical for translation initiation or mRNA stability and localization.

As is generally known in the art, commonly used oligonucleotides are oligomers or polymers of ribonucleotides or deoxyribonucleotides, that are composed of a naturally occurring nitrogenous base, a sugar (ribose or deoxyribose) and a phosphate group. In nature, the nucleotides are linked together by phosphodiesterbonds between the 3' and 5' positions of neighboring sugar moieties. However, it is noted that the term "oligonucleotides" also encompasses various non-naturally occurring mimetics and derivatives, i.e., modified forms, of naturally-occurring oligonucleotides as described below. Typically an antisense compound of the present invention is an oligonucleotide having from about 6 to about 200, and preferably from about 8 to about 30 nucleoside bases.

The antisense compounds preferably contain modified backbones or non-natural internucleoside linkages, including but not limited to, modified phosphorous-containing backbones and non-phosphorous backbones such as morpholino backbones: siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See e.g., U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Examples of the non-phosphorous containing backbones described above are disclosed in, e.g., U.S. Pat. Nos. 5,034,506; 5,185,444; 5,214,134; 5,216,141; 5,235,033; 5,264,562; 5,264,564; 5,405,938; 5,434,257; 5,470,967; 5,489,677; 5,541,307; 5,561,225; 5,596,086; 5,610,289; 5,602,240; 5,608,046; 5,610,289; 5,618,704; 5,623,070; 5,663,312; 5,677,437; and 5,677,439, each of which is herein incorporated by reference.

Another useful modified oligonucleotide is peptide nucleic acid (PNA), in which the sugar-backbone of an oligonucleotide is replaced with an amide containing backbone, e.g., an aminoethylglycine backbone. See U.S. Pat. Nos. 5,539,082 and 5,714,331; and Nielsen et al., *Science*, 254, 1497–1500 (1991), all of which are incorporated herein by reference. PNA antisense compounds are resistant to RNase H digestion and thus exhibit longer half-life. In addition, various modifications may be made in PNA backbones to impart desirable drug profiles such as better stability, increased drug uptake, higher affinity to target nucleic acid, etc.

Alternatively, the antisense compounds are oligonucleotides containing modified nucleosides, i.e., modified purine or pyrimidine bases, e.g., 5-substituted pyrimidines, 6-azapyrimidines, and N-2, N-6 and O-substituted purines, and the like. See e.g., U.S. Pat. Nos. 3,687,808; 4,845,205; 5,130,302; 5,175,273; 5,367,066; 5,432,272; 5,459,255; 5,484,908; 5,502,177; 5,525,711; 5,587,469; 5,594,121; 5,596,091; 5,681,941; and 5,750,692, each of which is incorporated herein by reference in its entirety.

In addition, oligonucleotides with substituted or modified sugar moieties may also be used. For example, an antisense compound may have one or more 2'-O-methoxyethyl sugar moieties. See e.g. U.S. Pat. Nos. 4,981,957; 5,118,800; 5,319,080; 5,393,878; 5,446,137; 5,466,786; 5,514,785; 5,567,811; 5,576,427; 5,591,722; 5,610,300; 5,627,053; 5,639,873; 5,646,265; 5,658,873; 5,670,633; and 5,700,920, each of which is herein incorporated by reference.

Other types of oligonucleotide modifications are also useful including linking an oligonucleotide to a lipid, phospholipid or cholesterol moiety, cholic acid, thioether, aliphatic chain, polyamine, polyethylene glycol (PEG), or a protein or peptide. The modified oligonucleotides may exhibit increased uptake into cells, and improved stability, i.e., resistance to nuclease digestion and other biodegradations. See e.g. U.S. Pat. No. 4,522,811; Burnham, *Am. J. Hosp. Pharm.*, 15:210–218 (1994).

Antisense compounds can be synthesized using any suitable methods known in the art. In fact, antisense compounds may be custom made by commercial suppliers. Alternatively, antisense compounds may be prepared using DNA synthesizers available commercially from various vendors, e.g., Applied Biosystems Group of Norwalk, Conn.

The antisense compounds can be formulated into a pharmaceutical composition with suitable carriers and administered into cells or tissue in vitro or into patients using any suitable route of administration. Alternatively, the antisense compounds may also be used in a "gene-therapy" approach. That is, the oligonucleotide is subcloned into a suitable vector and transformed into human cells. The antisense oligonucleotide is then produced in vivo through transcription. Methods for gene therapy are disclosed in Section 6.3.2 below.

6.2.3. Ribozyme Therapy

In another embodiment, an enzymatic RNA or ribozyme is designed to target the nucleic acids encoding one or more of the interacting protein members of the protein complex of the present invention. Ribozymes are RNA molecules possessing enzymatic activity. One class of ribozymes is capable of repeatedly cleaving other separate RNA molecules into two or more pieces in a nucleotide base sequence specific manner. See Kim et al., *Proc. Natl. Acad. of Sci. USA*, 84:8788 (1987); Haseloff and Gerlach, *Nature*, 334:585 (1988); and Jefferies et al., *Nucleic Acid Res.*, 17:1371 (1989). Such ribozymes typically have two functional domains: a catalytic domain and a binding sequence that guides the binding of ribozymes to a target RNA through complementary base-pairing. Once a specifically designed ribozyme is bound to a target mRNA, it enzymatically cleaves the target mRNA, typically reducing its stability and destroying its ability to direct translation of an encoded protein. After a ribozyme has cleaved its RNA target, it is released from that target RNA and thereafter can bind and cleave another target. That is, a single ribozyme molecule can repeatedly bind and cleave new targets. Therefore, one advantage of ribozyme treatment is that a lower amount of exogenous RNA is required as compared to conventional antisense therapies. In addition, ribozymes exhibit less affinity to mRNA targets than DNA-based antisense oligonucleotides, and therefore are less prone to bind to wrong targets.

In accordance with the present invention, a ribozyme may target any portions of the mRNA of one or more interacting protein members including MAP17 and SCAMP2. Methods for selecting a ribozyme target sequence and designing and making ribozymes are generally known in the art. See e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable ribozymes may be designed in various configurations such as hammerhead motifs, hairpin motifs, hepatitis delta virus motifs, group I intron motifs, or RNase P RNA motifs. See e.g., U.S. Pat. Nos. 4,987,071; 5,496,698; 5,525,468; 5,631,359; 5,646,020; 5,672,511; and 6,140,491; Rossi et al., *AIDS Res. Human Retroviruses* 8:183 (1992); Hampel and Tritz, *Biochemistry* 28:4929 (1989); Hampel et al., *Nucleic Acids Res.*, 18:299 (1990); Perrotta and Been, *Biochemistry* 31:16 (1992); and Guerrier-Takada et al., *Cell,* 35:849 (1983).

Ribozymes can be synthesized by the same methods used for normal RNA synthesis. For example, such methods are disclosed in Usman et al., *J. Am. Chem. Soc.,* 109:7845–7854 (1987) and Scaringe et al., *Nucleic Acids Res.,* 18:5433–5441 (1990). Modified ribozymes may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature,* 344:565 (1990); Pieken et al., *Science,* 253:314 (1991); and Usman and Cedergren, *Trends in Biochem. Sci.,* 17:334 (1992).

Ribozymes of the present invention may be administered to cells by any known methods, e.g., disclosed in International Publication No. WO 94/02595. For example, they can be administered directly to cells or tissue in vitro or to patients through any suitable route, e.g., intravenous injection. Alternatively, they may be delivered encapsulated in liposomes, by iontophoresis, or by incorporation into other vehicles such as hydrogels, cyclodextrins, biodegradable nanocapsules, and bioadhesive microspheres. In addition, they may also be delivered by gene therapy approach, using a DNA vector from which the ribozyme RNA can be transcribed directly. Gene therapy methods are disclosed in detail below in Section 6.3.2.

6.2.4. Other Methods

The in-patient concentrations and activities of the protein complexes and interacting proteins of the present invention may also be altered by other methods. For example, compounds identified in accordance with the methods described in Section 5 that are capable of interfering with or dissociating protein—protein interactions between the interacting protein members of a protein complex may be administered to cells or tissue in vitro or to patients. Compounds identified in in vitro binding assays described in Section 5.2 that bind to the protein complex comprising MAP17 and SCAMP2, or the interacting members thereof, may also be used in the treatment.

In addition, potentially useful agents also include incomplete proteins, i.e., fragments of the interacting protein members that are capable of binding to their respective binding partners in a protein complex but are defective with respect to their normal cellular functions. For example, binding domains of the interacting member proteins of a protein complex may be used as competitive inhibitors of the activities of the protein complex. As will be apparent to skilled artisans, derivatives or homologues of the binding domains may also be used. Binding domains can be easily identified using molecular biology techniques, e.g., mutagenesis in combination with yeast two-hybrid assays. Preferably, the protein fragment used is a fragment of an interacting protein member having a length of less than 90%, 80%, more preferably less than 75%, 65%, 50%, or less than 40% of the full length of the protein member. In one embodiment, a SCAMP2 protein fragment is administered. In a specific embodiment, one or more of the interaction domains of SCAMP2 within the regions listed in Table 1 are administered to cells or tissue in vitro, or are administered to a patient in need of such treatment. For example, suitable protein fragments can include polypeptides having a contiguous span of 4, 5, 6, 7, 8, 9, 10, 11, 12, 13, 14, 15, 18, 20 or 25 or more, preferably from 4 to 30, 40 or 50 amino acids or more of the sequence of SCAMP2 that are capable of interacting with MAP17. Also, suitable protein fragments can also include peptides capable of binding MAP17 and having an amino acid sequence of from 4 to 30, 40, 50 or more amino acids that is at least 75%, 80%, 82%, 85%, 87%, 90%, 95% or more identical to a contiguous span of amino acids of SCAMP2 of the same length. Alternatively, a polypeptide capable of interacting with SCAMP2 and having a contiguous span of 4, 5, 6, 7, 8, 9, 10, 11, 12, 13, 14, 15, 18, 20 or 25 or more, preferably from 4 to 30, 40 or 50 or more amino acids of the amino acid sequence of MAP17 may be administered. Also, other examples of suitable compounds include a peptide capable of binding SCAMP2 and having an amino acid sequence of from 4 to 30, 40, 50 or more amino acids that is at least 75%, 80%, 82%, 85%, 87%, 90%, 95% or more identical to a contiguous span of amino acids of the same length from MAP17. In addition, the administered compounds can also be an antibody or antibody fragment, preferably single-chain antibody immunoreactive with MAP17 or SCAMP2 or a protein complex of the present invention.

The protein fragments suitable as competitive inhibitors can be delivered into cells by direct cell internalization, receptor mediated endocytosis, or via a "transporter." It is noted that when the target proteins or protein complexes to be modulated reside inside cells, the compound administered to cells in vitro or in vivo in the method of the present invention preferably is delivered into the cells in order to achieve optimal results. Thus, preferably, the compound to be delivered is associated with a transporter capable of increasing the uptake of the compound by cells harboring the target protein or protein complex. As used herein, the term "transporter" refers to an entity (e.g., a compound or a composition or a physical structure formed from multiple copies of a compound or multiple different compounds) that is capable of facilitating the uptake of a compound of the present invention by animal cells, particularly human cells. Typically, the cell uptake of a compound of the present invention in the presence of a "transporter" is at least 20% higher, preferably at least 40%, 50%, 75%, and more preferably at least 100% higher than the cell uptake of the compound in the absence of the "transporter."

Many molecules and structures known in the art can be used as "transporters." In one embodiment, a penetratin is used as a transporter. For example, the homeodomain of Antennapedia, a *Drosophila* transcription factor, can be used as a transporter to deliver a compound of the present invention. Indeed, any suitable member of the penetratin class of peptides can be used to carry a compound of the present invention into cells. Penetratins are disclosed in, e.g., Derossi et al., *Trends Cell Biol.*, 8:84–87 (1998), which is incorporated herein by reference. Penetratins transport molecules attached thereto across cytoplasmic membranes or nuclear membranes efficiently, in a receptor-independent, energy-independent, and cell type-independent manner. Methods for using a penetratin as a carrier to deliver oligonucleotides and polypeptides are also disclosed in U.S. Pat. No. 6,080,724; Pooga et al., *Nat. Biotech.*, 16:857 (1998); and Schutze et al., *J. Immunol.*, 157:650 (1996), all of which are incorporated herein by reference. U.S. Pat. No. 6,080,724 defines the minimal requirements for a penetratin peptide as a peptide of 16 amino acids with 6 to 10 of which being hydrophobic. The amino acid at position 6 counting from either the N- or C-terminus is tryptophan, while the amino acids at positions 3 and 5 counting from either the N- or C-terminus are not both valine. Preferably, the helix 3 of the homeodomain of *Drosophila* Antennapedia is used as a transporter. More preferably, a peptide having a sequence of amino acid residues 43–58 of the homeodomain Antp is employed as a transporter. In addition, other naturally occurring homologs of the helix 3 of the homeodomain of *Drosophila* Antennapedia can be used. For example, homeodomains of Fushi-tarazu and Engrailed have been shown to be capable of transporting peptides into cells. See Han et al., *Mol. Cells*, 10:728–32 (2000). As used herein, the term "penetratin" also encompasses peptoid analogs of the penetratin peptides. Typically, the penetratin peptides and peptoid analogs thereof are covalently linked to a compound to be delivered into cells thus increasing the cellular uptake of the compound.

In another embodiment; the HIV-1 tat protein or a derivative thereof is used as a "transporter" covalently linked to a compound according to the present invention. The use of HIV-1 tat protein and derivatives thereof to deliver macromolecules into cells has been known in the art. See Green and Loewenstein, *Cell*, 55:1179 (1988); Frankel and Pabo, *Cell*, 55:1189 (1988); Vives et al., *J. Biol. Chem.*, 272:16010–16017 (1997); Schwarze et al., *Science*, 285:1569–1572 (1999). It is known that the sequence responsible for cellular uptake consists of the highly basic region, amino acid residues 49–57. See e.g., Vives et al., *J. Biol. Chem.*, 272:16010–16017 (1997); Wender et al., *Proc. Natl. Acad. Sci. USA*, 97:13003–13008 (2000). The basic domain is believed to target the lipid bilayer component of cell membranes. It causes a covalently linked protein or nucleic acid to cross cell membrane rapidly in a cell type-independent manner. Proteins ranging in size from 15 to 120 kD have been delivered with this technology into a variety of cell types both in vitro and in vivo. See Schwarze et al., *Science*, 285:1569–1572 (1999). Any HIV tat-derived peptides or peptoid analogs thereof capable of transporting macromolecules such as peptides can be used for purposes of the present invention. For example, any native tat peptides having the highly basic region, amino acid residues 49–57 can be used as a transporter by covalently linking it to the compound to be delivered. In addition, various analogs of the tat peptide of amino acid residues 49–57 can also be useful transporters for purposes of this invention. Examples of various such analogs are disclosed in Wender et al., *Proc. Nat'l Acad. Sci. USA*, 97:13003–13008 (2000) (which is incorporated herein by reference) including, e.g., d-$Tat_{49-57}$, retro-inverso isomers of l- or d-$Tat_{49-57}$ (i.e., l-$Tat_{57-49}$ and d-$Tat_{57-49}$), L-arginine oligomers, D-arginine oligomers, L-lysine oligomers, D-lysine oligomers, L-histine oligomers, D-histine oligomers, L-ornithine oligomers, D-ornithine oligomers, and various homologues, derivatives (e.g., modified forms with conjugates linked to the small peptides) and peptoid analogs thereof.

Other useful transporters known in the art include, but are not limited to, short peptide sequences derived from fibroblast growth factor (See Lin et al., *J. Biol. Chem.*, 270:14255–14258 (1998)), Galparan (See Pooga et al., *FASEB J.* 12:67–77 (1998)), and HSV-1 structural protein VP22 (See Elliott and O'Hare, *Cell*, 88:223–233 (1997)).

As the above-described various transporters are generally peptides, fusion proteins can be conveniently made by recombinant expression to contain a transporter peptide covalently linked by a peptide bond to a competitive protein fragment. Alternatively, conventional methods can be used to chemically synthesize a transporter peptide or a peptide of the present invention or both.

The hybrid peptide can be administered to cells or tissue in vitro or to patients in a suitable pharmaceutical composition as provided in Section 8.

In addition to peptide-based transporters, various other types of transporters can also be used, including but not limited to cationic liposomes (see Rui et al., *J. Am. Chem. Soc.*, 120:11213–11218 (1998)), dendrimers (Kono et al., *Bioconjugate Chem.*, 10:1115–1121 (1999)), siderophores (Ghosh et al., *Chem. Biol.*, 3:1011–1019 (1996)), etc. In a specific embodiment, the compound according to the present invention is encapsulated into liposomes for delivery into cells.

Additionally, when a compound according to the present invention is a peptide, it can be administered to cells by a gene therapy method. That is, a nucleic acid encoding the peptide can be administered to cells in vitro or to cells in a human or animal body. Any suitable gene therapy methods may be used for purposes of the present invention. Various gene therapy methods are well known in the art and are described in Section 6.3.2. below. Successes in gene therapy have been reported recently. See e.g., Kay et al., *Nature Genet.*, 24:257–61 (2000); Cavazzana-Calvo et al., *Science*, 288:669 (2000); and Blaese et al., *Science*, 270: 475 (1995); Kantoff, et al., *J. Exp. Med.*, 166:219 (1987).

In yet another embodiment, the gene therapy methods discussed in Section 6.3.2 below are used to "knock out" the gene encoding an interacting protein member of a protein complex, or to reduce the gene expression level. For example, the gene may be replaced with a different gene sequence or a non-functional sequence or simply deleted by homologous recombination. In another gene therapy embodiment, the method disclosed in U.S. Pat. No. 5,641,670, which is incorporated herein by reference, may be used to reduce the expression of the genes for the interacting protein members. Essentially, an exogenous DNA having at least a regulatory sequence, an exon and a splice donor site can be introduced into an endogenous gene encoding an interacting protein member by homologous recombination such that the regulatory sequence, the exon and the splice donor site present in the DNA construct become operatively linked to the endogenous gene. As a result, the expression of the endogenous gene is controlled by the newly introduced exogenous regulatory sequence. Therefore, when the exogenous regulatory sequence is a strong gene expression repressor, the expression of the endogenous gene encoding the interacting protein member is reduced or blocked. See U.S. Pat. No. 5,641,670.

6.3. Activating the Protein Complex or the Interacting Protein Members Thereof The present invention also provides methods for increasing in cells or tissue in vitro or in patients the concentration and/or activity of a protein complex, or of an individual protein member thereof, identified in accordance with the present invention. Such methods can be particularly useful in instances where a reduced concentration and/or activity of a protein complex, or a protein member thereof, is associated with a particular disease or disorder to be treated, or where an increased concentration and/or activity of a protein complex, or a protein member thereof, would be beneficial to the improvement of a cellular function or disease state. By increasing the concentration of the protein complex, or a protein member thereof, and/or stimulating the functional activities of the protein complex or a protein member thereof, the disease or disorder may be treated or prevented.

6.3.1. Administration of Protein Complex or Protein Members Thereof

Where the concentration or activity of a protein complex comprising MAP17 and SCAMP2 of the present invention, or MAP17 or SCAMP2, in cells or tissue in vitro or in patients is determined to be low or is desired to be increased, the protein complex comprising MAP17 and SCAMP2 of the present invention, or separately, MAP17 and/or SCAMP2 may be administered directly to the patient to increase the concentration and/or activity of the protein complex comprising MAP17 and SCAMP2: For this purpose, protein complexes prepared by any one of the methods described in Section 2.2 may be administered to the patient, preferably in a pharmaceutical composition as described below. Alternatively, one or more individual interacting protein members of the protein complex may also be administered to the patient in need of treatment. For example, one or more proteins such as MAP17 or SCAMP2 may be given to cells or tissue in vitro or to patients. Proteins or complexes isolated or purified from normal individuals or recombinantly produced can all be used in this respect. Preferably, two or more interacting protein members of a protein complex are administered. The proteins or protein complexes may be administered to a patient needing treatment using any of the methods described in Section 8.

6.3.2. Gene Therapy

In another embodiment, the concentration and/or activity of a protein complex comprising MAP17 and SCAMP2, or separately, MAP17 and/or SCAMP2, is increased or restored in patients, tissues or cells by a gene therapy approach. For example, nucleic acids encoding MAP17 (or fragments, homologues or derivatives thereof), and/or SCAMP2 (or fragments, homologues or derivatives thereof), are introduced into patients, tissues or cells such that one or more proteins are expressed from the introduced nucleic acids. For these purposes, nucleic acids encoding one or both of MAP17 (or fragments, homologues or derivatives thereof), or SCAMP2 (or fragments, homologues or derivatives thereof), can be used in the gene therapy in accordance with the present invention. For example, if a disease-causing mutation exists in one of the interacting proteins in cells or tissue in vitro or in patients, then a nucleic acid encoding a wild-type protein can be introduced into the patient, tissue or cells. The exogenous nucleic acid can be used to replace the corresponding endogenous defective gene by, e.g., homologous recombination. See U.S. Pat. No. 6,010,908, which is incorporated herein by reference. Alternatively, if the disease-causing mutation is a recessive mutation, the exogenous nucleic acid is simply used to express a wild-type protein in addition to the endogenous mutant protein. In another approach, the method disclosed in U.S. Pat. No. 6,077,705 may be employed in gene therapy. That is, the patient is administered both a nucleic acid construct encoding a ribozyme and a nucleic acid construct comprising a ribozyme resistant gene encoding a wild type form of the gene product. As a result, undesirable expression of the endogenous gene is inhibited and a desirable wild-type exogenous gene is introduced. In yet another embodiment, if the endogenous gene is of wild-type and the level of expression of the protein encoded thereby is desired to be increased, additional copies of wild-type exogenous genes may be introduced into the patient by gene therapy, or alternatively, a gene activation method such as that disclosed in U.S. Pat. No. 5,641,670 may be used.

Various gene therapy methods are well known in the art. Successes in gene therapy have been reported recently. See e.g. Kay et al. *Nature Genet.,* 24:257–61 (2000); Cavazzana-Calvo et al., *Science,* 288:669 (2000); and Blaese et al., *Science,* 270: 475 (1995); Kantoff, et al., *J. Exp. Med.* 166:219 (1987).

Any suitable gene therapy methods may be used for the purposes of the present invention. Generally, a nucleic acid encoding a desirable protein (i.e., MAP17 or SCAMP2) is incorporated into a suitable expression vector and is operably linked to a promoter in the vector. Suitable promoters include but are not limited to viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Where tissue-specific expression of the exogenous gene is desirable, tissue-specific promoters may be operably linked to the exogenous gene. In addition, selection markers may also be included in the vector for purposes of selecting, in vitro, those cells that contain the exogenous gene. Various selection markers known in the art may be used including, but not limited to, e.g., genes conferring resistance to neomycin, hygromycin, zeocin, and the like.

In one embodiment, the exogenous nucleic acid (gene) is incorporated into a plasmid DNA vector. Many commercially available expression vectors may be useful for the present invention, including, e.g., pCEP4, pcDNAI, pIND, pSecTag2, pVAX1, pcDNA3.1, and pBI-EGFP, and pDisplay.

Various viral vectors may also be used. Typically, in a viral vector, the viral genome is engineered to eliminate the disease-causing capability of the virus, e.g., the ability to replicate in the host cells. The exogenous nucleic acid to be introduced into cells or tissue in vitro or into patients may be incorporated into the engineered viral genome, e.g., by inserting it into a viral gene that is non-essential to the viral infectivity. Viral vectors are convenient to use as they can be easily introduced into cells, tissues and patients by way of infection. Once in the host cell, the recombinant virus typically is integrated into the genome of the host cell. In rare instances, the recombinant virus may also replicate and remain as extrachromosomal elements.

A large number of retroviral vectors have been developed for gene therapy. These include vectors derived from oncoretroviruses (e.g., MLV), lentiviruses (e.g., HIV and SIV) and other retroviruses. For example, gene therapy vectors have been developed based on murine leukemia virus (See, Cepko, et al., Cell, 37:1053–1062 (1984), Cone and Mulligan, Proc. Natl. Acad. Sci. U.S.A., 81:6349–6353 (1984)), mouse mammary tumor virus (See, Salmons et al., Biochem. Biophys. Res. Commun. 159:1191–1198 (1984)), gibbon ape leukemia virus (See, Miller et al., J. Virology, 65:2220–2224 (1991)), HIV, (See Shimada et al., J. Clin. Invest., 88:1043–1047 (1991)), and avian retroviruses (See Cosset et al., J. Virology, 64:1070–1078 (1990)). In addition, various retroviral vectors are also described in U.S. Pat. Nos. 6,168,916; 6,140,111; 6,096,534; 5,985,655; 5,911,983; 4,980,286; and 4,868,116, all of which are incorporated herein by reference.

Adeno-associated virus (AAV) vectors have been successfully tested in clinical trials. See e.g., Kay et at., Nature Genet. 24:257–61 (2000). AAV is a naturally occurring defective virus that requires other viruses such as adenoviruses or herpes viruses as helper viruses. See Muzyczka, Curr. Top. Microbiol. Immun., 158:97 (1992). A recombinant AAV virus useful as a gene therapy vector is disclosed in U.S. Pat. No. 6,153,436, which is incorporated herein by reference.

Adenoviral vectors can also be useful for purposes of gene therapy in accordance with the present invention. For example, U.S. Pat. No. 6,001,816 discloses an adenoviral, which is used to deliver a leptin gene intravenously to a mammal to treat obesity. Other recombinant adenoviral vectors may also be used, which include those disclosed in U.S. Pat. Nos. 6,171,855; 6,140,087; 6,063,622; 6,033,908; and 5,932,210, and Rosenfeld et al., Science, 252:431–434 (1991); and Rosenfeld et al., Cell, 68:143–155 (1992).

Other useful viral vectors include recombinant hepatitis viral vectors (See, e.g., U.S. Pat. No. 5,981,274), and recombinant entomopox vectors (See, e.g., U.S. Pat. Nos. 5,721,352 and 5,753,258).

Other non-traditional vectors may also be used for purposes of this invention. For example, International Publication No. WO 94/18834 discloses a method of delivering DNA into mammalian cells by conjugating the DNA to be delivered with a polyelectrolyte to form a complex. The complex may be microinjected into or taken up by cells.

The exogenous gene fragment or plasmid DNA vector containing the exogenous gene may also be introduced into cells by way of receptor-mediated endocytosis. See e.g., U.S. Pat. No. 6,090,619; Wu and Wu, J. Biol. Chem., 263:14621 (1988); Curiel et al., Proc. Natl. Acad. Sci. USA, 88:8850 (1991). For example, U.S. Pat. No. 6,083,741 discloses introducing an exogenous nucleic acid into mammalian cells by associating the nucleic acid to a polycation moiety (e.g., poly-L-lysine having 3–100 lysine residues), which is itself coupled to an integrin receptor binding moiety (e.g., a cyclic peptide having the sequence Arg-Gly-Asp).

Alternatively, the exogenous nucleic acid or vectors containing it can also be delivered into cells via amphiphiles. See e.g., U.S. Pat. No. 6,071,890. Typically, the exogenous nucleic acid or a vector containing the nucleic acid forms a complex with the cationic amphiphile. Mammalian cells contacted with the complex can readily take it up.

The exogenous gene can be introduced into a patient for purposes of gene therapy by various methods known in the art. For example, the exogenous gene sequences alone or in a conjugated or complex form described above, or incorporated into viral or DNA vectors, may be administered directly by injection into an appropriate tissue or organ of a patient. Alternatively, catheters or like devices may be used to deliver exogenous gene sequences, complexes, or vectors into a target organ or tissue. Suitable catheters are disclosed in, e.g., U.S. Pat. Nos. 4,186,745; 5,397,307; 5,547,472; 5,674,192; and 6,129,705, all of which are incorporated herein by reference.

In addition, the exogenous gene or vectors containing the gene can be introduced into isolated cells using any known techniques such as calcium phosphate precipitation, microinjection, lipofection, electroporation, biolystics, receptor-mediated endocytosis, and the like. Cells expressing the exogenous gene may be selected and redelivered back to the patient by, e.g., injection or cell transplantation. The appropriate amount of cells delivered to a patient will vary with patient conditions, and desired effect, which can be determined by a skilled artisan. See e.g., U.S. Pat. Nos. 6,054,288; 6,048,524; and 6,048,729. Preferably, the cells used are autologous, i.e., cells obtained from the patient being treated.

6.3.3. Small Organic Compounds

Defective conditions in cells or tissue in vitro or in patients associated with decreased concentration or activity of a protein complex comprising MAP17 and SCAMP2, identified in accordance with the present invention, or separately, MAP 17 or SCAMP2, can also be ameliorated by administering to the patient a compound identified by the methods described in Sections 5.3.1.4, 5.2, and Section 5.4, which is capable of modulating the functions of the protein complex, e.g., by triggering or initiating, enhancing or stabilizing protein—protein interaction between the interacting protein members thereof, or the mutant forms of such interacting protein members found in the patient.

7. Cell and Animal Models

In another aspect of the present invention, cell and animal models are provided in which protein complexes comprising MAP17 and SCAMP2, or one or both of MAP17 and SCAMP2 exhibit aberrant function, activity, or concentration when compared with wildtype cells and animals, e.g., increased or decreased concentration, altered interactions between protein complex constituents due to mutations in interaction domains, and/or altered distribution or localization of the protein complexes or constituents thereof (e.g., in organs, tissues, cells, or cellular compartments). Such cell and animal models ale useful tools for studying cellular functions and biological processes associated with the protein complex of the present invention comprising MAP17 and SCAMP2, for studying disorders and diseases associated with the protein complex comprising MAP17 and SCAMP2, and for testing various methods for modulating the cellular functions, and for treating the diseases and disorders, associated with the protein complex comprising MAP17 and SCAMP2.

7.1. Cell Models

Cell models having an aberrant form of one or more of the protein complexes of the present invention are provided in accordance with the present invention.

The cell models may be established by isolating, from a patient, cells having an aberrant form of one or more of the protein complexes of the present invention. The isolated cells may be cultured in vitro as a primary cell culture. Alternatively, the cells obtained from the primary cell culture or directly from the patient may be immortalized to establish a human cell line. Any methods for constructing immortalized human cell lines may be used in this respect. See generally Yeager and Reddel, *Curr. Opini. Biotech.*, 10:465–469 (1999). For example, the human cells may be immortalized by transfection of plasmids expressing the SV40 early region genes (See e.g., Jha et al., *Exp. Cell Res.*, 245:1–7 (1998)), introduction of the HPV E6 and E7 oncogenes (See e.g., Reznikoff et al., *Genes Dev.*, 8:2227–2240 (1994)), and infection with Epstein-Barr virus (See e.g., Tahara et al., *Oncogene*, 15:1911–1920 (1997)). Alternatively, the human cells may be immortalized by recombinantly expressing the gene for the human telomerase catalytic subunit hTERT in the human cells. See Bodnar et al., *Science*, 279:349–352 (1998).

In alternative embodiments, cell models are provided by recombinantly manipulating appropriate host cells. The host cells may be bacteria cells, yeast cells, insect cells, plant cells, animal cells, and the like. Preferably, the cells are derived from mammals, most preferably humans. The host cells may be obtained directly from an individual, or a primary cell culture, or preferably an immortal stable human cell line. In a preferred embodiment, human embryonic stem cells or pluripotent cell lines derived from human stem cells are used as host cells. Methods for obtaining such cells are disclosed in, e.g., Shamblott, et al., *Proc. Natl. Acad. Sci. USA*, 95:13726–13731 (1998) and Thomson et al., *Science*, 282:1145–1147 (1998).

In one embodiment, a cell model is provided by recombinantly expressing one or more of the protein complexes of the present invention in cells that do not normally express such protein complexes. For example, cells that do not contain a particular protein complex may be engineered to express the protein complex. In a specific embodiment, a particular human protein complex is expressed in non-human cells. The cell model may be prepared by introducing into host cells nucleic acids encoding all interacting protein members required for the formation of a particular protein complex, and expressing the protein members in the host cells. For this purpose, the recombinant expression methods described in Section 2.2 may be used. In addition, the methods for introducing nucleic acids into host cells disclosed in the context of gene therapy in Section 6.2.2 may also be used.

In another embodiment, a cell model over-expressing one or more of the protein complexes of the present invention is provided. The cell model may be established by increasing the expression level of one or more of the interacting protein members of the protein complexes. In a specific embodiment, all interacting protein members of a particular protein complex are over-expressed. The over-expression may be achieved by introducing into host cells exogenous nucleic acids encoding the proteins to be over-expressed, and selecting those cells that over-express the proteins. The expression of the exogenous nucleic acids may be transient or, preferably stable. The recombinant expression methods described in Section 2.2, and the methods for introducing nucleic acids into host cells disclosed in the context of gene therapy in Section 6.2.2 may be used. Alternatively, the gene activation method disclosed in U.S. Pat. No. 5,641,670 can be used. Any host cells may be employed for establishing the cell model. Preferably, human cells lacking a protein complex to be over-expressed, or having a normal concentration of the protein complex, are used as host cells. The host cells may be obtained directly from an individual, or a primary cell culture, or preferably a stable immortal human cell line. In a preferred embodiment, human embryonic stem cells or pluripotent cell lines derived from human stem cells are used as host cells. Methods for obtaining such cells are disclosed in, e.g., Shamblott, et al., *Proc. Natl. Acad. Sci. USA*, 95:13726–13731 (1998), and Thomson et al., *Science*, 282:1145–1147 (1998).

In yet another embodiment, a cell model expressing an abnormally low level of the protein complex of the present invention is provided. Typically, the cell model is established by genetically manipulating cells that express normal and detectable levels of the protein complex identified in accordance with the present invention. Generally the expression level of one or more of the interacting protein members of the protein complex is reduced by recombinant methods. In a specific embodiment, the expression of both interacting protein members of the protein complex is reduced. The reduced expression may be achieved by "knocking out" the genes encoding one or both interacting protein members. Alternatively, mutations that can cause reduced expression level (e.g., reduced transcription and/or translation efficiency, and decreased mRNA stability) may also be introduced into the gene by homologous recombination. A gene encoding a ribozyme or antisense compound specific to the mRNA encoding an interacting protein member may also be introduced into the host cells, preferably stably integrated into the genome of the host cells. In addition, a gene encoding an antibody or fragment thereof specific to an interacting protein member may also be introduced into the host cells. The recombinant expression methods described in Sections 2.2, 6.1 and 6.2 can all be used for purposes of manipulating the host cells.

The present invention also contemplates a cell model provided by recombinant DNA techniques that exhibits aberrant interactions between the interacting protein members of the protein complex identified in the present invention. For example, variants of the interacting protein members of a particular protein complex exhibiting altered protein—protein interaction properties and the nucleic acid variants encoding such variant proteins may be obtained by random or site-directed mutagenesis in combination with a protein—protein interaction assay system, particularly the yeast two-hybrid system described in Section 5.3.1. Essentially, the genes encoding one or more interacting protein members of a particular protein complex may be subject to random or site-specific mutagenesis and the mutated gene sequences are used in yeast two-hybrid system to test the protein—protein interaction characteristics of the protein variants encoded by the gene variants. In this manner, variants of the interacting protein members of the protein complex may be identified that exhibit altered protein—protein interaction properties in forming the protein complex, e.g., increased or decreased binding affinity, and the like. The nucleic acid variants encoding such protein variants may be introduced into host cells by the methods described above, preferably into host cells that normally do not express the interacting proteins.

7.2. Cell-Based Assays

The cell models of the present invention containing an aberrant form of a protein complex comprising MAP17 and SCAMP2 of the present invention are useful in screening assays for compounds useful in treating diseases and disorders involving regulating cell proliferation and membrane trafficking such as kidney, colon, breast, and lung cancers. In addition, they may also be used in in vitro pre-clinical assays for testing compounds, such as those identified in the screening assays of the present invention.

For example, cells may be treated with compounds to be tested and assayed for the compound's activity. A variety of parameters relevant to particularly physiological disorders or diseases may be analyzed.

7.3. Transgenic Animals

In another aspect of the present invention, transgenic non-human animals are created expressing an aberrant form of one or both of MAP17 and SCAMP2, the constituents of the protein complexes identified in the present invention. Animals of any species may be used to generate the transgenic animal models, including but not limited to, mice, rats, hamsters, sheep, pigs, rabbits, guinea pigs, preferably non-human primates such as monkeys, chimpanzees, baboons, and the like.

In one embodiment, transgenic animals are made to over-express one or more protein complexes formed from MAP17 or a derivative or homologue thereof (including the animal counterpart of MAP17, i.e., orthologues) and SCAMP2, or a derivative or homologue thereof (including an animal counterpart thereof, i.e., orthologues). Over-expression may be directed in a tissue or cell type that normally expresses the animal counterparts (orthologues) of such protein complexes. Consequently, the concentration of the protein complex(es) will be elevated to higher levels than normal. Alternatively, the expression of MAP17, or a derivative, homologue, or orthologue thereof, and SCAMP2, or a derivative or homologue, or orthologue thereof, may be directed in tissues or cells that do not normally express such proteins and hence do not normally contain the protein complex(es) of the present invention. In a specific embodiment, human MAP17 and human SCAMP2 are expressed in the transgenic animals, in the presence or absence of expression of animal orthologues.

To achieve over-expression in transgenic animals, the transgenic animals are made such that they contain and express exogenous, orthologous genes encoding MAP17 or a homologue, derivative or mutant form thereof and SCAMP2 or a homologue, derivative or mutant form thereof. Preferably, both exogenous genes are human genes. Such exogenous genes may be operably linked to a native or non-native promoter, preferably a non-native promoter. For example, an exogenous MAP17 gene may be operably linked to a promoter that is not the native MAP17 promoter. If the expression of the exogenous gene is desired to be limited to a particular tissue, an appropriate tissue-specific promoter may be used.

Over-expression may also be achieved by manipulating the native promoter to create mutations that lead to gene over-expression, or by a gene activation method such as that disclosed in U.S. Pat. No. 5,641,670 as described above.

In another embodiment, the transgenic animal expresses an abnormally low concentration of the complex comprising MAP17 and SCAMP2. In a specific embodiment, the transgenic animal is a "knockout" animal wherein the endogenous gene encoding the animal orthologue of MAP17 and/or an endogenous gene encoding an animal orthologue of SCAMP2 are knocked out. In a specific embodiment, the expression of the animal orthologues of both MAP17 and SCAMP2 are reduced or knocked out. The reduced expression may be achieved by knocking out the genes encoding one or both interacting protein members, typically by homologous recombination. Alternatively, mutations that can cause reduced expression (e.g., reduced transcription and/or translation efficiency, or decreased mRNA stability) may also be introduced into the endogenous genes by homologous recombination. Genes encoding ribozymes or antisense compounds specific to the mRNAs encoding the interacting protein members may also be introduced into the transgenic animal. In addition, genes encoding antibodies or fragments thereof specific to the, interacting protein members may also be introduced into the transgenic animal.

In an alternate embodiment, transgenic animals are made in which the endogenous genes encoding the animal orthologues of MAP17 and SCAMP2 are replaced with the human versions of genes (i.e., orthologous genes) encoding MAP17 and SCAMP2.

In yet another embodiment, the transgenic animal of this invention expresses specific mutant forms of MAP17 and SCAMP2 (or their orthologues) that exhibit aberrant interactions. For this purpose, variants of MAP17 and SCAMP2 exhibiting altered protein—protein interaction properties and the nucleic acid variants encoding such variant proteins may be obtained by random or site-specific mutagenesis in combination with a protein—protein interaction assay system, particularly the yeast two-hybrid system described in Section 5.3.1. For example, variants of MAP17 and SCAMP2 exhibiting increased, decreased or abolished binding affinity to each other may be identified and isolated. The transgenic animal of the present invention may be made to express such protein variants by modifying the endogenous genes. Alternatively, the nucleic acid variants may be introduced exogenously into the transgenic animal genome to express the protein variants therein. In a specific embodiment, the exogenous nucleic acid variants are derived from orthologous human genes and the corresponding endogenous genes are knocked out.

Any techniques known in the art for making transgenic animals maybe used for purposes of the present invention. For example, the transgenic animals of the present invention may be provided by methods described in, e.g., Jaenisch, *Science*, 240:1468–1474 (1988); Capecchi, et al., *Science*, 244:1288–1291 (1989); Hasty et al., *Nature*, 350:243 (1991); Shinkai et al., *Cell*, 68:855 (1992); Mombaerts et al., *Cell*, 68:869 (1992); Philpott et al., *Science*, 256:1448 (1992); Snouwaert et al., *Science*, 257:1083 (1992); Donehower et al., *Nature*, 356:215 (1992); Hogan et al., *Manipulating the Mouse Embryo; A Laboratory Manual*, $2^{nd}$ edition, Cold Spring Harbor Laboratory Press, 1994; and U.S. Pat. Nos. 4,873,191; 5,800,998; 5,891,628, all of which are incorporated herein by reference.

Generally, the founder lines may be established by introducing appropriate exogenous nucleic acids into, or modifying an endogenous gene in, germ lines, embryonic stem cells, embryos, or sperm which are then used in producing a transgenic animal. The gene introduction may be conducted by various methods including those described in Sections 2.2, 6.1 and 6.2. See also, Van der Putten et al., *Proc. Natl. Acad. Sci. USA*, 82:6148–6152 (1985); Thompson et al., *Cell*, 56:313–321 (1989); Lo, *Mol. Cell. Biol.*, 3:1803–1814 (1983); Gordon, *Trangenic Animals, Intl. Rev. Cytol.* 115:171–229 (1989); and Lavitrano et al., *Cell*, 57:717–723 (1989). In a specific embodiment, the exogenous gene is incorporated into an appropriate vector, such as those described in Sections 2.2 and 6.2, and is transformed into embryonic stem (ES) cells. The transformed ES cells are then injected into a blastocyst. The blastocyst with the transformed ES cells is then implanted into a surrogate mother animal. In this manner, a chimeric founder line animal containing the exogenous nucleic acid (transgene) may be produced.

Preferably, site-specific recombination is employed to integrate the exogenous gene into a specific predetermined site in the animal genome, or to replace an endogenous gene or a portion thereof with the exogenous sequence. Various site-specific recombination systems may be used including those disclosed in Sauer, *Curr. Opin. Biotechnol.*, 5:521–527 (1994); Capecchi, et al., *Science,* 244:1288–1291 (1989); and Gu et al., *Science,* 265:103–106 (1994). Specifically, the Cre/lox site-specific recombination system known in the art may be conveniently used which employs the bacteriophage P1 protein Cre recombinase and its recognition sequence loxP. See Rajewsky et al., *J. Clin. Invest.*, 98:600–603 (1996); Sauer, *Methods,* 14:381–392 (1998); Gu et al., *Cell,* 73:1155–1164 (1993); Araki et al., *Proc. Natl. Acad. Sci. USA,* 92:160–164 (1995); Lakso et al., *Proc. Natl. Acad. Sci. USA,* 89:6232–6236 (1992); and Orban et al., *Proc. Natl. Acad. Sci. USA,* 89:6861–6865 (1992).

The transgenic animals of the present invention may be transgenic animals that carry a transgene in all cells or mosaic transgenic animals carrying a transgene only in certain cells, e.g., somatic cells. The transgenic animals may have a single copy or multiple copies of a particular transgene.

The founder transgenic animals thus produced may be bred to produce various offsprings. For example, they can be inbred, outbred, and crossbred to establish homozygous lines, heterozygous lines, and compound homozygous or heterozygous lines.

8. Pharmaceutical Compositions and Formulations

In another aspect of the present invention, pharmaceutical compositions are also provided containing one or more of the therapeutic agents provided in the present invention as described in Section 6. The compositions are prepared as a pharmaceutical formulation suitable for administration into a patient. Accordingly, the present invention also extends to pharmaceutical compositions, medicaments, drugs or other compositions containing one or more of the therapeutic agent in accordance with the present invention.

For example, such therapeutic agents include, but are not limited to, (1) small organic compounds selected based on the screening methods of the present invention capable of interfering with the interaction between MAP17 and an interactor thereof, (2) antisense compounds specifically hybridizable to MAP17 nucleic acids (gene or mRNA) (3) antisense compounds specific to the gene or mRNA of a MAP17 interactor, (4) ribozyme compounds specific to MAP17 nucleic acids (gene or mRNA), (5) ribozyme compounds specific to the gene or mRNA of SCAMP2, (6) antibodies immunoreactive with MAP17 or SCAMP2, (7) antibodies selectively immunoreactive with a protein complex of the present invention, (8) small organic compounds capable of binding a protein complex of the present invention, (9) small peptide compounds as described above (optionally linked to a transporter) capable of interacting with MAP17 or SCAMP2, (10) nucleic acids encoding the antibodies or peptides, etc.

The compositions are prepared as a pharmaceutical formulation suitable for administration into a patient. Accordingly, the present invention also extends to pharmaceutical compositions, medicaments, drugs or other compositions containing one or more of the therapeutic agent in accordance with the present invention.

In the pharmaceutical composition, an active compound identified in accordance with the present invention can be in any pharmaceutically acceptable salt form. As used herein, the term "pharmaceutically acceptable salts" refers to the relatively non-toxic, organic or inorganic salts of the compounds of the present invention, including inorganic or organic acid addition salts of the compound. Examples of such salts include, but are not limited to, hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naththylate salts, mesylate salts, tosylate salts, citrate salts, lactate salts, maleate salts, succinate salts, tartrate salts, fumarate salts, and the like. See, e.g. Berge, et al., *J. Pharm. Sci.,* 66:1–19 (1977).

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacterial agents, surfactants, and antioxidants can all be included. For example, useful components include sodium chloride, acetate, citrate or phosphate buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine,* 39:221–229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych.* 45:242–247 (1984). Hydrogels can be used as a carrier for the sustained release of the active compounds. Hydrogels are generally known in the art. They are typically made by crosslinking high molecular weight biocompatible polymers into a network that swells in water to form a gel like material. Preferably, hydrogels is biodegradable or biosorbable. For purposes of this invention, hydrogels made of polyethylene glycols, collagen, or poly(glycolic-co-L-actic acid) may be useful. See, e.g., Phillips et al., *J. Pharmaceut. Sci.* 73:1718–1720 (1984).

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, *Am. J. Hosp. Pharm.,* 15:210–218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology,* Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, Antiviral agents, antibiotics, antifungal agents, antithrombotic agents, cardiovascular drugs, cholesterol lowering agents, anticancer drugs, hypertension drugs, and the like.

Generally, the toxicity profile and therapeutic efficacy of the therapeutic agents can be determined by standard pharmaceutical procedures in cell models or animal models, e.g., those provided in Section 7. As is known in the art, the $LD_{50}$ represents the dose lethal to about 50% of a tested population. The $ED_{50}$ is a parameter indicating the dose therapeutically effective in about 50% of a tested population. Both $LD_{50}$ and $ED_{50}$ can be determined in cell models and animal models. In addition, the $IC_{50}$ may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the $ED_{50}$ and/or $IC_{50}$, but significantly below the $LD_{50}$ obtained from cell or animal models.

It will be apparent to skilled artisans that therapeutically effective amount for each active compound to be included in a pharmaceutical composition of the present invention can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like. The amount of administration can also be adjusted as the various factors change over time.

EXAMPLES

1. Yeast Two-Hybrid System

The principles and methods of the yeast two-hybrid system have been described in detail in *The Yeast Two-Hybrid System,* Bartel and Fields, eds., pages 183–196, Oxford University Press, New York, N.Y., 1997. The following is thus a description of the particular procedure that we used, which was applied to all proteins.

The cDNA encoding the bait protein was generated by PCR from cDNA prepared from a desired tissue. The cDNA product was then introduced by recombination into the yeast expression vector pGBT.Q, which is a close derivative of pGBT.C (See Bartel et al., *Nat Genet.,* 12:72–77 (1996)) in which the polylinker site has been modified to include M13 sequencing sites. The new construct was selected directly in the yeast strain PNY200 for its ability to drive tryptophane synthesis (genotype of this strain: MATα trp1-901 leu2-3, 112 ura3-52 his3-200 ade2 gal4Δ gal80). In these yeast cells, the bait was produced as a C-terminal fusion protein with the DNA binding domain of the transcription factor Gal4 (amino acids 1 to 147). Prey libraries were transformed into the yeast strain BK100 (genotype of this strain: MATα trp1-901 leu2-3,112 ura3-52 his3-200 gal4Δ gal80 LYS2::GAL-HIS3 GAL2-ADE2 met2::GAL7-lacZ), and selected for the ability to drive leucine synthesis. In these yeast cells, each cDNA was expressed as a fusion protein with the transcription activation domain of the transcription factor Gal4 (amino acids 768 to 881) and a 9 amino acid hemagglutinin epitope tag. PNY200 cells (MATα mating type), expressing the bait, were then mated with BK100 cells (MATa mating type), expressing prey proteins from a prey library. The resulting diploid yeast cells expressing proteins interacting with the bait protein were selected for the ability to synthesize tryptophan, leucine, histidine, and adenine. DNA was prepared from each clone, transformed by electroporation into *E. coli* strain KC8 (Clontech KC8 electrocompetent cells, Catalog No. C2023-1), and the cells were selected on ampicillin-containing plates in the absence of either tryptophane (selection for the bait plasmid) or leucine (selection for the library plasmid). DNA for both plasmids was prepared and sequenced by the dideoxynucleotide chain termination method. The identity of the bait cDNA insert was confirmed and the cDNA insert from the prey library plasmid was identified using the BLAST program to search against public nucleotide and protein databases. Plasmids from the prey library were then individually transformed into yeast cells together with a plasmid driving the synthesis of lamin and 5 other test proteins, respectively, fused to the Gal4 DNA binding domain. Clones that gave a positive signal in the β-galactosidase assay were considered false-positives and discarded. Plasmids for the remaining clones were transformed into yeast cells together with the original bait plasmid. Clones that gave a positive signal in the β-galactosidase assay were considered true positives.

Bait sequences indicated in Table 1 were used in the yeast two-hybrid system described above. The isolated prey sequences are summarized in Table 1. The GenBank Accession Nos. for the bait and prey proteins are also provided in Table 1, upon which the bait and prey sequences are aligned.

2. Production of Antibodies Selectively Immunoreactive with Protein Complex

The MAP17-interacting region of SCAMP2 and the SCAMP2-interacting region of MAP17 are indicated in Table 1 in Section 2. Both regions, or fragments thereof, are recombinantly expressed in $E.$ $coli.$ and isolated and purified. Mixing the two purified interacting domains forms a protein complex. A protein complex is also formed by mixing recombinantly expressed intact complete MAP17 and SCAMP2. The two protein complexes are used as antigens in immunizing a mouse. mRNA is isolated from the immunized mouse spleen cells, and first-strand cDNA is synthesized using the mRNA as a template. The $V_H$ and $V_K$ genes are amplified from the thus synthesized cDNAs by PCR using appropriate primers.

The amplified $V_H$ and $V_K$ genes are ligated together and subcloned into a phagemid vector for the construction of a phage display library. $E.$ $coli.$ cells are transformed with the ligation mixtures, and thus a phage display library is established. Alternatively, the ligated $V_H$ and $V_k$ genes are subcloned into a vector suitable for ribosome display in which the $V_H$–$V_K$ sequence is under the control of a T7 promoter. See Schaffitzel et al., *J. Immun. Meth,* 231:119–135 (1999).

The libraries are screened for their ability to bind the complex comprising MAP17 and SCAMP2, and MAP17 or SCAMP2, alone. Several rounds of screening are generally performed. Clones corresponding to scFv fragments that bind the the complex comprising MAP17 and SCAMP2, but not isolated MAP17 or SCAMP2 are selected and purified. A single purified clone is used to prepare an antibody selectively immunoreactive with the complex comprising MAP17 and SCAMP2. The antibody is then verified by an immunochemistry method such as RIA and ELISA.

In addition, the clones corresponding to scFv fragments that bind the the complex comprising MAP17 and SCAMP2 and also bind isolated MAP17 and/or SCAMP2 may be selected. The scFv genes in the clones are diversified by mutagenesis methods such as oligonucleotide-directed mutagenesis, error-prone PCR (See Lin-Goerke et al, *Biotechniques,* 23:409 (1997)), dNTP analogues (See Zaccolo et al., *J. Mol. Biol.,* 255:589 (1996)), and other methods. The diversified clones are further screened in phage display or ribosome display libraries. In this manner, scFv fragments selectively immunoreactive with the complex comprising MAP17 and SCAMP2 may be obtained.

3. Yeast Screen to Identify Small Molecule Inhibitors of the Interaction Between MAP17 and SCAMP2

Beta-galactosidase is used as a reporter enzyme to signal the interaction between yeast two-hybrid protein pairs expressed from plasmids in *Saccharomyces cerevisiae.* Yeast strain MY209 (ade2 his3 leu2 trp1 cyh2 ura3::GAL1p-lacZ gal$^4$ gal80 lys2::GAL1p-HIS3) bearing one plasmid with the genotype of LEU2 CEN4 ARS1 ADH1p-SV40NLS-GAL4 (768-881)-SCAMP2-PGK1t AmpR ColE1_ori, and another plasmid having a genotype of TRP1 CEN4 ARS ADH1p-GAL4(1-147)-MAP17-ADH1t AmpR ColE1_ori is cultured in synthetic complete media lacking leucine and tryptophan (SC-Leu-Trp) overnight at 30° C. The MAP17 and SCAMP2 nucleic acids in the plasmids can code for the full-length MAP17 and SCAMP2 proteins, respectively, or fragments thereof. This culture is diluted to 0.01 $OD_{630}$ units/ml using SC-Leu-Trp media. The diluted MY209 culture is dispensed into 96-well microplates. Compounds from a library of small molecules are added to the microplates; the final concentration of test compounds is approximately 60 µM. The assay plates are incubated at 30° C. overnight.

The following day an aliquot of concentrated substrate/lysis buffer is added to each well and the plates incubated at 37° C. for 1–2 hours. At an appropriate time an aliquot of stop solution is added to each well to halt the beta-galactosidase reaction. For all microplates an absorbance reading is obtained to assay the generation of product from the enzyme substrate. The presence of putative inhibitors of the interaction between MAP17 and SCAMP2 results in inhibition of the beta-galactosidase signal generated by MY209. Additional testing eliminates compounds that decreased expression of beta-galactosidase by affecting yeast cell growth and non-specific inhibitors that affected the beta-galactosidase signal generated by the interaction of an unrelated protein pair.

Once a hit, i.e., a compound which inhibits the interaction between the interacting proteins, is obtained, the compound is identified and subjected to further testing wherein the compounds are assayed at several concentrations to determine an $IC_{50}$ value, this being the concentration of the compound at which the signal seen in the two-hybrid assay described in this Example is 50% of the signal seen in the absence of the inhibitor.

4. Enzyme-Linked Immunosorbent Assay (ELISA)

pGEX5X-2 (Amersham Biosciences; Uppsala, Sweden) is used for the expression of a GST-SCAMP2 fusion protein. The pGEX5X-2-SCAMP2 construct is transfected into *Escherichia coli* strain DH5α (Invitrogen; Carlsbad, Calif.) and fusion protein is prepared by inducing log phase cells (O.D. 595=0.4) with 0.2 mM isopropyl-β-D-thiogalactopyranoside (IPTG). Cultures are harvested after approximately 4 hours of induction, and cells pelleted by centrifugation. Cell pellets are resuspended in lysis buffer (1% nonidet P-40 [NP-40], 150 mM NaCl, 10 mM Tris pH 7.4, 1 mM ABESF [4-(2-aminoethyl) benzenesulfonyl fluoride]), lysed by sonication and the lysate cleared of insoluble materials by centrifugation. Cleared lysate is incubated with Glutathione Sepharose beads (Amersham Biosciences; Uppsala, Sweden) followed by thorough washing with lysis buffer. The GST-SCAMP2 fusion protein is then eluted from the beads with 5 mM reduced glutathione. Eluted protein is dialyzed against phosphate buffer saline (PBS) to remove the reduced glutathione.

A stable *Drosophila* Schneider 2 (S2) myc-MAP17 expression cell line is generated by transfecting S2 cells with the hygromycin B resistance vector PCOHYGRO™

(Invitrogen; Carlsbad, Calif.) and an expression vector that directs the expression of the myc-MAP17 fusion protein. Briefly, S2 cells are washed and resuspended in serum free Express Five media (Invitrogen; Carlsbad, Calif.). Plasmid/liposome complexes are then added NOVAFECTOR™, Venn Nova; Pompano reach, FL) and allowed to incubate with cells for 12 hours under standard growth conditions (room temperature, no $CO_2$ buffering). Following this incubation period fetal bovine serum is added to a final concentration of 20% and cells are allowed to recover for 24 hours. The media is replaced and cells are grown for an additional 24 hours. Transfected cells are then selected in 350 µg/ml hygromycin for three weeks. Expression of myc-MAP17 is confirmed by Western blotting. This cell line is referred to as S2-myc-MAP17.

GST-SCAMP2 fusion protein is immobilized to wells of an ELISA plate as follows: high absorption microtiter (NUNC MAXISORB™ 96 well) ELISA plates (Nalge Nunc International; Rochester, N.Y.) are incubated with 100 µl of 10 µg/ml of GST-SCAMP2 in 50 mM carbonate buffer (pH 9.6) and stored overnight at 4° Celsius. This plate is referred to as the ELISA plate.

A compound dilution plate is generated in the following manner. In a 96 well polypropylene plate (Greiner, Germany) 50 µl of DMSO is pipetted into columns 2–12. In the same polypropylene plate pipette, 10 µl of each compound being tested for its ability to modulate protein—protein interactions is plated in the wells of column 1 followed by 90 µl of DMSO (final volume of 100 µl). Compounds selected from primary screens or from virtual screening, or designed based on the primary screen hits are then serially diluted by removing 50 µl from column 1 and transferring it to column 2 (50:50 dilution). Serial dilutions are continued until column 10. This plate is termed the compound dilution plate.

Next, 12 µl from each well of the compound dilution plate is transferred into its corresponding well in a new polypropylene plate. 108 µl of S2-myc-MAP17-containing lysate ($1\times10^6$ cell equivalents/ml) in phosphate buffered saline is added to all wells of columns 1–11. 108 µl of phosphate buffered saline without lysate is added into all wells of column 12. The plate is then mixed on a shaker for 15 minutes. This plate is referred to as the compound preincubation plate.

The ELISA plate is emptied of its contents and 400 µl of Superblock (Pierce Endogen; Rockford, Ill.) is added to all the wells and allowed to sit for 1 hour at room temperature. 100 µl from all columns of the compound preincubation plate are transferred into the corresponding wells of the ELISA binding plate. The plate is then covered and allowed to incubate for 1.5 hours room temperature.

The interaction of the myc-tagged MAP17 with the immobilized GST-SCAMP2 is detected by washing the ELISA plate followed by an incubation with 100 µl/well of 1 µg/ml of mouse anti-myc IgG (clone 9E10; Roche Applied Science; Indianapolis, Ind.) in phosphate buffered saline. After 1 hour at room temperature, the plates are washed with phosphate buffered saline and incubated with 100 µl/well of 250 ng/ml of goat anti-mouse IgG conjugated to horseradish peroxidase in phosphate buffer saline. Plates are then washed again with phosphate buffered saline and incubated with the fluorescent substrate solution Quantiblu (Pierce Endogen; Rockford, Ill.). Horseradish peroxidase activity is then measured by reading the plates in a fluorescent plate reader (325 nm excitation, 420 nm emission).

Although the foregoing invention has been described in some detail by way of illustration and example for purposes of clarity of understanding, it will be obvious that certain changes and modifications may be practiced within the scope of the appended claims.

In various parts of this disclosure, certain publications or patents are discussed or cited. The mere discussion of, or reference to, such publications or patents is not intended as admission that they are prior art to the present invention.

What is claimed is:

1. A method for selecting modulators of an interaction between a first protein and a second protein,
   (a) said first protein being selected from the group consisting of
      (i) MAP17 (SEQ ID NO:1),
      (ii) a MAP17 homologue having an amino acid sequence at least 90% identity to that of MAP17 (SEQ ID NO:1) and capable of interacting with SCAMP2 (SEQ ID NO:2),
      (iii) a MAP17 fragment of MAP17 (SEQ ID NO:1) capable of interacting with SCAMP2 (SEQ ID NO:2), and
      (iv) a fusion protein containing MAP17 (SEQ ID NO:1), said MAP17 homologue or said MAP17 fragment; and
   (b) said second protein being selected from the group consisting of
      (1) SCAMP2 (SEQ ID NO:2),
      (2) a SCAMP2 homologue having an amino acid sequence at least 90% identity to that of SCAMP2 (SEQ ID NO:2) and capable of interacting with MAP17 (SEQ ID NO:1),
      (3) a SCAMP2 fragment of SCAMP2 (SEQ ID NO:2) capable of interacting with MAP17 (SEQ ID NO:1), and
      (4) a fusion protein containing SCAMP2 (SEQ ID NO:2), said SCAMP2 homologue or said SCAMP2 fragment, said method comprising:
   contacting said first protein with said second protein in the presence of a test compound; and
   detecting the interaction between said first protein and said second protein; and
   selecting a test compound that modulates the interaction between a first protein and a second protein.

2. The method of claim 1, wherein at least one of said first and second proteins is a fusion protein having a detectable tag.

3. The method of claim 1, wherein said contacting step is conducted in vitro.

4. The method of claim 1, wherein the interaction between said first protein and said second protein is determined in a host cell.

5. The method of claim 4, wherein said host cell is a yeast cell.

6. The method of claim 1, wherein said detecting step comprises measuring the amount of the protein complex formed by said first and second proteins.

7. The method of claim 1, further comprising a step of generating a data set defining one or more selected test compounds, said data set being embodied in a transmittable form.

8. A method for selecting compounds capable of interfering with the interaction between a first protein and a second protein, wherein
   (a) said first protein is selected from the group consisting of
      (i) MAP17 (SEQ ID NO:1),
      (ii) a MAP17 homologue having an amino acid sequence at least 90% identity to that of MAP17 (SEQ ID NO:1 and capable of interacting with SCAMP2 (SEQ ID NO:2),
      (iii) a MAP17 fragment of MAP17 (SEQ ID NO:1) capable of interacting with SCAMP2 (SEQ ID NO:2), and
      (iv) a fusion protein containing MAP17 (SEQ ID NO:1), said MAP17 homologue or said MAP17 fragment; and
   (b) said second protein is selected from the group consisting of
      (1) SCAMP2 (SEQ ID NO:2),
      (2) a SCAMP2 homologue having an amino acid sequence at least 90% identity to that of SCAMP2 (SEQ ID NO:2) and capable of interacting with MAP17 (SEQ ID NO:1),
      (3) a SCAMP2 fragment of SCAMP2 (SEQ ID NO:2) capable of interacting with MAP17 (SEQ ID NO:1), and
      (4) a fusion protein containing SCAMP2 (SEQ ID NO:2), said SCAMP2 homologue or said SCAMP2 fragment, said method comprising:
   contacting said first protein with said second protein in the presence of a test compound and detecting the interaction between said first protein and said second protein; and
   contacting said first protein with said second protein in the absence of said test compound and detecting the interaction between said first protein and said second protein; and
   selecting a compound that interferes the interaction between a first protein and a second protein.

9. The method of claim 8, wherein said contacting steps are conducted in vitro.

10. The method of claim 8, wherein said contacting steps are conducted in a host cell.

11. The method of claim 8, wherein the first protein is a fusion protein containing MAP17 (SEQ ID NO:1), said MAP17 homologue or said MAP17 fragment of MAP17 (SEQ ID NO:1), and said second protein is a fusion protein containing SCAMP2 (SEQ ID NO:2), said SCAMP2 homologue or said SCAMP2 fragment of SCAMP2 (SEQ ID NO:2).

12. The method of claim 8, further comprising a step of generating a data set defining one or more selected test compounds, said data set being embodied in a transmittable form.

* * * * *

SEQUENCE LISTING

<160> NUMBER OF SEQ ID NOS: 2

<210> SEQ ID NO 1
<211> LENGTH: 114
<212> TYPE: PRT
<213> ORGANISM: Homo sapiens

<400> SEQUENCE: 1

Met Ser Ala Leu Ser Leu Leu Ile Leu Gly Leu Leu Thr Ala Val Pro
1               5                   10                  15

Pro Ala Ser Cys Gln Gln Gly Leu Gly Asn Leu Gln Pro Trp Met Gln
            20                  25                  30

Gly Leu Ile Ala Val Ala Val Phe Leu Val Leu Val Ala Ile Ala Phe
        35                  40                  45

Ala Val Asn His Phe Trp Cys Gln Glu Glu Pro Glu Pro Ala His Met
    50                  55                  60

Ile Leu Thr Val Gly Asn Lys Ala Asp Gly Val Leu Val Gly Thr Asp
65                  70                  75                  80

Gly Arg Tyr Ser Ser Met Ala Ala Ser Phe Arg Ser Ser Glu His Glu
                85                  90                  95

Asn Ala Tyr Glu Asn Val Pro Glu Glu Gly Lys Val Arg Ser Thr
            100                 105                 110

Pro Met

<210> SEQ ID NO 2
<211> LENGTH: 329
<212> TYPE: PRT
<213> ORGANISM: Homo sapiens

<400> SEQUENCE: 2

```
Met Ser Ala Phe Asp Thr Asn Pro Phe Ala Asp Pro Val Asp Val Asn
1               5                   10                  15

Pro Phe Gln Asp Pro Ser Val Thr Gln Leu Thr Asn Ala Pro Gln Gly
            20                  25                  30

Gly Leu Ala Glu Phe Asn Pro Phe Ser Glu Thr Asn Ala Ala Thr Thr
        35                  40                  45

Val Pro Val Thr Gln Leu Pro Gly Ser Ser Gln Pro Ala Val Leu Gln
    50                  55                  60

Pro Ser Val Glu Pro Thr Gln Pro Thr Pro Gln Ala Val Val Ser Ala
65                  70                  75                  80

Ala Gln Ala Gly Leu Leu Arg Gln Gln Glu Glu Leu Asp Arg Lys Ala
                85                  90                  95

Ala Glu Leu Glu Arg Lys Glu Arg Glu Leu Gln Asn Thr Val Ala Asn
            100                 105                 110

Leu His Val Arg Gln Asn Asn Trp Pro Pro Leu Pro Ser Trp Cys Pro
        115                 120                 125

Val Lys Pro Cys Phe Tyr Gln Asp Phe Ser Thr Glu Ile Pro Ala Asp
    130                 135                 140

Tyr Gln Arg Ile Cys Lys Met Leu Tyr Leu Trp Met Leu His Ser
145                 150                 155                 160

Val Thr Leu Phe Leu Asn Leu Leu Ala Cys Leu Ala Trp Phe Ser Gly
                165                 170                 175

Asn Ser Ser Lys Gly Val Asp Phe Gly Leu Ser Ile Leu Trp Phe Leu
            180                 185                 190

Ile Phe Thr Pro Cys Ala Phe Leu Cys Trp Tyr Arg Pro Ile Tyr Lys
        195                 200                 205

Ala Phe Arg Ser Asp Asn Ser Phe Ser Phe Val Phe Phe Val
    210                 215                 220

Phe Phe Cys Gln Ile Gly Ile Tyr Ile Ile Gln Leu Val Gly Ile Pro
225                 230                 235                 240

Gly Leu Gly Asp Ser Gly Trp Ile Ala Ala Leu Ser Thr Leu Asp Asn
                245                 250                 255

His Ser Leu Ala Ile Ser Val Ile Met Met Val Val Ala Gly Phe Phe
            260                 265                 270

Thr Leu Cys Ala Val Leu Ser Val Phe Leu Leu Gln Arg Val His Ser
        275                 280                 285

Leu Tyr Arg Arg Thr Gly Ala Ser Phe Gln Gln Ala Gln Glu Glu Phe
    290                 295                 300

Ser Gln Gly Ile Phe Ser Ser Arg Thr Phe His Arg Ala Ala Ser Ser
305                 310                 315                 320

Ala Ala Gln Gly Ala Phe Gln Gly Asn
                325
```